(12) United States Patent
DiPietro et al.

(10) Patent No.: US 9,499,522 B2
(45) Date of Patent: Nov. 22, 2016

(54) COMPOSITIONS USEFUL FOR TREATING DISORDERS RELATED TO KIT

(71) Applicants: Lucian V. DiPietro, Gloucester, MA (US); Brian L. Hodous, Cambridge, MA (US); Joseph L. Kim, Wayland, MA (US); Chandrasekhar V. Miduturu, Cambridge, MA (US); Steven Mark Wenglowsky, Cambridge, MA (US); Douglas Wilson, Ayer, MA (US); Yulian Zhang, Acton, MA (US)

(72) Inventors: Lucian V. DiPietro, Gloucester, MA (US); Brian L. Hodous, Cambridge, MA (US); Joseph L. Kim, Wayland, MA (US); Chandrasekhar V. Miduturu, Cambridge, MA (US); Steven Mark Wenglowsky, Cambridge, MA (US); Douglas Wilson, Ayer, MA (US); Yulian Zhang, Acton, MA (US)

(73) Assignee: BLUEPRINT MEDICINES CORPORATION, Cambridge, MA (US)

( * ) Notice: Subject to any disclaimer, the term of this patent is extended or adjusted under 35 U.S.C. 154(b) by 0 days.

(21) Appl. No.: 14/210,526

(22) Filed: Mar. 14, 2014

(65) Prior Publication Data

US 2014/0296206 A1 Oct. 2, 2014

Related U.S. Application Data

(60) Provisional application No. 61/788,857, filed on Mar. 15, 2013.

(51) Int. Cl.

| | | |
|---|---|---|
| *C07D 403/12* | (2006.01) |
| *C07D 401/14* | (2006.01) |
| *C07D 405/14* | (2006.01) |
| *C07D 409/14* | (2006.01) |
| *C07D 413/14* | (2006.01) |
| *C07D 487/04* | (2006.01) |
| *C07D 487/08* | (2006.01) |
| *C07D 401/12* | (2006.01) |
| *C07D 403/04* | (2006.01) |
| *C07D 403/14* | (2006.01) |
| *C07D 239/94* | (2006.01) |
| *C07D 487/22* | (2006.01) |

(52) U.S. Cl.
CPC ........... *C07D 403/12* (2013.01); *C07D 239/94* (2013.01); *C07D 401/12* (2013.01); *C07D 401/14* (2013.01); *C07D 403/04* (2013.01); *C07D 403/14* (2013.01); *C07D 405/14* (2013.01); *C07D 409/14* (2013.01); *C07D 413/14* (2013.01); *C07D 487/04* (2013.01); *C07D 487/08* (2013.01); *C07D 487/22* (2013.01)

(58) Field of Classification Search
CPC .......................... C07D 403/12; C07D 487/04
USPC ....................................... 514/266.2; 544/284
See application file for complete search history.

(56) References Cited

U.S. PATENT DOCUMENTS

| | | | |
|---|---|---|---|
| 6,982,265 B1 | 1/2006 | Hunt et al. | |
| 8,609,672 B2 * | 12/2013 | Russu | C07D 239/42 514/266.1 |

FOREIGN PATENT DOCUMENTS

| | | |
|---|---|---|
| WO | 0071129 A1 | 11/2000 |
| WO | 01/25220 A1 | 4/2001 |
| WO | 2005117909 A2 | 12/2005 |
| WO | 2007085188 A1 | 8/2007 |
| WO | 2008005956 A2 | 1/2008 |
| WO | 2009015254 A1 | 1/2009 |
| WO | 2009117157 A1 | 9/2009 |
| WO | 2010022055 A2 | 2/2010 |
| WO | 2010144345 A1 | 12/2010 |
| WO | 2011005119 A1 | 1/2011 |
| WO | 2011103196 A1 | 8/2011 |
| WO | 2012027495 A1 | 3/2012 |
| WO | 2014160521 A1 | 10/2014 |
| WO | 2015057873 A1 | 4/2015 |
| WO | 2015058129 A1 | 4/2015 |

OTHER PUBLICATIONS

Antonescu, "What lessons can be learned from the GIST paradigm that can be applied to other kinase-driven cancers" J. Pathol. (2011) vol. 223, No. 2, pp. 251-261.
Cecil Textbook of Medicine, Edited by Bennet and Plum (1996) 20th edition, vol. 1, pp. 1004-1010.
Cohen et al., "The development and therapeutic potential of protein kinase inhibitors" Current Opinion in Chemical Biology (1999) vol. 3, pp. 459-465.
Fresheny et al., "Culture of Animal Cells, a Manual of Basic Technique" Alan R. Liss, Inc. (1983) pp. 1-6.
International Search Report and Written Opinion for International Application No. PCT/US2014/027008 dated Jul. 17, 2014.
International Search Report and Written Opinion for International Application No. PCT/US2014/060746 dated Dec. 17, 2014.
International Search Report and Written Opinion for International Application No. PCT/US2014/061211 dated Oct. 12, 2014.
Lee et al. "Correlation of Imatinib Resistance with the Mutational Status of KIT and ODGFRA Genes in Gastrointestinal Stromal Tumors: a Meta-analysis" J. Gastrointestin Liver Dis. (2013) vol. 22, No. 4, pp. 413-418.
Quintela et al, "A Ready One-pot Preparation for Pyrrolo[2,1-f]-[1,2,4]triazine and Pyrazolo[5,1-c]pyrimido[4,5-e]-[1,2,4]triazine Derivatives" Tetrahedron (1996) vol. 52, No. 8, pp. 3037-3048.

(Continued)

*Primary Examiner* — Paul V Ward
(74) *Attorney, Agent, or Firm* — Lando & Anastasi, LLP

(57) ABSTRACT

Compounds and compositions useful for treating disorders related to Kit are described herein.

27 Claims, No Drawings

(56) References Cited

OTHER PUBLICATIONS

Cairoli et al. "Prognostic impact of c-KIT mutations in core binding factor leukemias: an Italian retrospective study" Blood (2006) vol. 107, pp. 3463-3468.
Dermer "Another Anniversary for the War on Cancer" Bio/Technology (1994) vol. 12, pp. 320.
International Search Report for International Application No. PCT/US2015/043624 dated Oct. 6, 2015.
Paschka et al. "Adverse Prognostic Significance of KIT Mutations in Adult Acute Myeloid Leukemia with inv(16) and t(8;21):A Cancer and Leukemia Group Study" Journal of Clinical Oncology (2006) vol. 24, No. 24, pp. 3904-3911.
Schnittger et al. "KIT-D816 mutations in AML1-ETO-positive AML are associated with impaired event-free and overal survival" Blood (2006) vol. 107, pp. 1791-1799.

\* cited by examiner

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-FAM-Gly
<220> FEATURE:
<221> NAME/KEY: MOD_RES
<222> LOCATION: (14)..(14)
<223> OTHER INFORMATION: Lys-NH2

<400> SEQUENCE: 1

Gly Glu Glu Pro Leu Tyr Trp Ser Phe Pro Ala Lys Lys Lys
1               5                   10
```

COMPOSITIONS USEFUL FOR TREATING DISORDERS RELATED TO KIT

CLAIM OF PRIORITY

This application claims priority to U.S. Ser. No. 61/788,857 filed Mar. 15, 2013, the contents of which is incorporated herein by reference in its entirety.

SEQUENCE LISTING

The instant application contains a Sequence Listing which has been submitted electronically In ASCII format and is hereby incorporated by reference in its entirety. Said ASCII copy, created on May 27, 2014, is named B2094-700310—SL.txt and is 830 bytes in size

BACKGROUND

The invention relates to compounds and compositions useful for treating disorders related to Kit.

The enzyme Kit (also called CD117) is a receptor tyrosine kinase (RTK) expressed on a wide variety of cell types. The Kit molecule contains a long extracellular domain, a transmembrane segment, and an intracellular portion. The ligand for Kit is stem cell factor (SCF), whose binding to the extracellular domain of Kit induces receptor dimerization and activation of downstream signaling pathways. Kit mutations generally occur in the DNA encoding the juxtumembrane domain (exon 11). They also occur, with less frequency, in exons 7, 8, 9, 13, 14, 17, and 18. Mutations make Kit function independent of activation by SCF, leading to a high cell division rate and possibly genomic instability. Mutant Kit has been implicated in the pathogenesis of several disorders and conditions including including systemic mastocytosis, GIST (gastrointestinal stromal tumors), AML (acute myeloid leukemia), melanoma, and seminoma. As such, there is a need for therapeutic agents that inhibit Kit, and especially agents that inhibit mutant Kit.

SUMMARY OF THE INVENTION

The present invention provides compounds and compositions for treating or preventing conditions such as mastocytosis by modulating the activity of Kit, such compounds having the structural formula I:

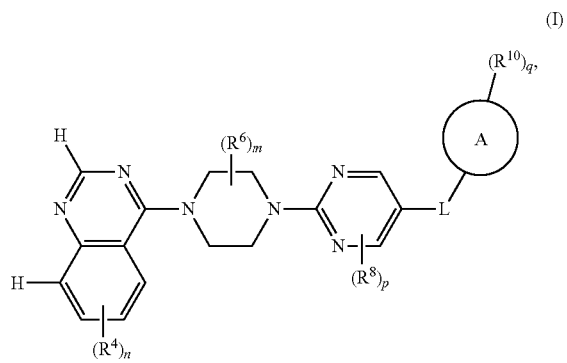

(I)

or a pharmaceutically acceptable salt or a tautomer thereof, wherein each of the variables are described herein.

Any of the compounds disclosed herein may be used to treat any of the diseases disclosed herein.

DETAILED DESCRIPTION OF THE INVENTION

"Aliphatic group" means a straight-chain, branched-chain, or cyclic hydrocarbon group and includes saturated and unsaturated groups, such as an alkyl group, an alkenyl group, and an alkynyl group.

"Alkenyl" means an aliphatic group containing at least one double bond.

"Alkoxyl" or "alkoxy" means an alkyl group having an oxygen radical attached thereto. Representative alkoxyl groups include methoxy, ethoxy, propyloxy, tert-butoxy and the like.

"Alkyl" refers to a monovalent radical of a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

"Alkylene" refers to a divalent radical of an alkyl group.

"$C_0$ alkylene" refers to a bond. Thus, a moiety defined herein as "—($C_0$-$C_6$ alkylene)-aryl" includes both -aryl (i.e., $C_0$ alkylene-aryl) and —($C_1$-$C_6$ alkylene)-aryl.

"Halo" refers to a radical of any halogen, e.g., —F, —Cl, —Br, or —I.

"Haloalkyl" refers to an alkyl group that is substituted with at least one halogen. For example, —$CH_2F$, —$CHF_2$, —$CF_3$, —$CH_2CF_3$, —$CF_2CF_3$, and the like.

"Carbocyclic ring system" refers to a monocyclic, bicyclic or polycyclic hydrocarbon ring system, wherein each ring is either completely saturated or contains one or more units of unsaturation, but where no ring is aromatic.

"Carbocyclyl" refers to a monovalent radical of a carbocyclic ring system. Representative carbocyclyl groups include cycloalkyl groups (e.g., cyclopentyl, cyclobutyl, cyclopentyl, cyclohexyl and the like), and cycloalkenyl groups (e.g., cyclopentenyl, cyclohexenyl, cyclopentadienyl, and the like).

"Aromatic ring system" is art-recognized and refers to a monocyclic, bicyclic or polycyclic hydrocarbon ring system, wherein at least one ring is aromatic.

"Aryl" refers to a monovalent radical of an aromatic ring system. Representative aryl groups include fully aromatic ring systems, such as phenyl, naphthyl, and anthracenyl, and ring systems where an aromatic carbon ring is fused to one or more non-aromatic carbon rings, such as indanyl, phthalimidyl, naphthimidyl, or tetrahydronaphthyl, and the like.

"Heteroaromatic ring system" is art-recognized and refers to monocyclic, bicyclic or polycyclic ring system wherein at least one ring is both aromatic and comprises at least one heteroatom (e.g., N, O or S); and wherein no other rings are heterocyclyl (as defined below). In certain instances, a ring which is aromatic and comprises a heteroatom contains 1, 2, 3, or 4 ring heteroatoms in such ring.

"Heteroaryl" refers to a monovalent radical of a heteroaromatic ring system. Representative heteroaryl groups include ring systems where (i) each ring comprises a heteroatom and is aromatic, e.g., imidazolyl, oxazolyl, thiazolyl, triazolyl, pyrrolyl, furanyl, thiophenyl pyrazolyl, pyridinyl, pyrazinyl, pyridazinyl, pyrimidinyl, indolizinyl, purinyl, naphthyridinyl, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1,4-oxazin-3(4H)-one, 5,6,7,8-tetrahydroquinolinyl and 5,6,7,8-tetrahydroisoquinolinyl; and (iii) each ring is aromatic or carbocyclyl, and at least on aromatic ring shares a bridgehead heteroatom with another aromatic ring, e.g., 4H-quinolizinyl.

"Heterocyclic ring system" refers to monocyclic, bicyclic and polycyclic ring systems where at least one ring is saturated or partially unsaturated (but not aromatic) and comprises at least one heteroatom. A heterocyclic ring system can be attached to its pendant group at any heteroatom or carbon atom that results in a stable structure and any of the ring atoms can be optionally substituted.

"Heterocyclyl" refers to a monovalent radical of a heterocyclic ring system. Representative heterocyclyls include ring systems in which (i) every ring is non-aromatic and at least one ring comprises a heteroatom, e.g., tetrahydrofuranyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl, 1,2,3,4-tetrahydroisoquinolinyl; and (iii) at least one ring is non-aromatic and comprises a heteroatom and at least one other ring is aromatic and comprises a heteroatom, e.g., 3,4-dihydro-1H-pyrano[4,3-c]pyridine, and 1,2,3,4-tetrahydro-2,6-naphthyridine.

"Saturated heterocyclyl" refers to a radical of heterocyclic ring system wherein every ring is saturated, e.g, tetrahydrofuran, tetrahydro-2H-pyran, pyrrolidine, piperidine and piperazine.

"Methylene" refers to the divalent radical —$CH_2$—.

"Ethane-1,2-diyl" refers to the divalent radical —$CH_2CH_2$—.

"Propane-1,3-diyl" refers to the divalent radical —$CH_2CH_2CH_2$—.

"Methylenedioxy" refers to the divalent radical —O—$CH_2$—O—.

"Substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group (such as an alkyl, alkenyl, alkynyl, alkylene, alkenylene, alkynylene or the carbon atom of a carbocyclyl, aryl, heterocyclyl or heteroaryl) are independently halogen; —$(CH_2)_{0-4}R°$; —$(CH_2)_{0-4}OR°$; —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-1}Ph$ which may be substituted with $R°$; —CH=CHPh, which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR°$—, $SC(S)SR°$; —$(CH_2)_{0-4}SC(O)R°$; —$(CH_2)_{0-4}C(O)NR°_2$; —$C(S)NR°_2$; —$C(S)SR°$; —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —C(O)—$N(R°)$—$S(O)_2$—$R°$; —$N(OR°)R°$; —$C(NH)NR°_2$; —$P(O)_2R°$; —$P(O)R°_2$; —$OP(O)R°_2$; —$OP(O)(OR°)_2$; —$SiR°_3$; —$(C_{1-4}$ straight or branched) alkylene)O—$N(R°)_2$; or —$(C_{1-4}$ straight or branched)alkylene)C(O)O—$N(R°)_2$, wherein each $R°$ may be substituted as defined below and is independently hydrogen, $C_{1-6}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R°$ (or the ring formed by taking two independent occurrences of $R°$ together with their intervening atoms), are independently halogen, —$(CH_2)_{0-2}R^•$, -(halo$R^•$), —$(CH_2)_{0-2}OH$, —$(CH_2)_{0-2}OR^•$, —$(CH_2)_{0-2}CH(OR^•)_2$; —O(halo$R^•$), —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$OSiR^•_3$, —$C(O)SR^•$, —$(C_{1-4}$ straight or branched alkylene)C(O)O$R^•$, or —$SSR^•$ wherein each $R^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R°$ include =O and =S.

Suitable divalent substituents on a saturated carbon atom of an "optionally substituted" group include the following: =O ("oxo"), =S, =$NNR^*_2$, =$NNHC(O)R^*$, =$NNHC(O)OR^*$, =$NNHS(O)_2R^*$, =$NR^*$, =$NOR^*$, —O(C($R^*_2$))$_{2-3}$O—, or —S(C($R^*_2$))$_{2-3}$S—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(C$R^*_2$)$_{2-3}$O—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R●-(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R†, -(haloR†), —OH, —OR*, —O(haloR†), —CN, —C(O)OH, —C(O)OR†, —NH$_2$, —NHR†, —NR†$_2$, or —NO$_2$, wherein each R† is unsubstituted or where preceded by "halo" is substituted only with one or more halogens, and is independently C$_{1-4}$aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the definition of each expression, e.g., alkyl, m, n, etc., when it occurs more than once in any structure, is intended to be independent of its definition elsewhere in the same structure.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Unless otherwise indicated, when a disclosed compound is named or depicted by a structure without specifying the stereochemistry and has one or more chiral centers, it is understood to represent all possible stereoisomers of the compound, as well as enantiomeric mixtures thereof.

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

$$ee=(90-10)/100=80\%.$$

Thus, a composition containing 90% of one enantiomer and 10% of the other enantiomer is said to have an enantiomeric excess of 80%.

The compounds or compositions described herein may contain an enantiomeric excess of at least 50%, 75%, 90%, 95%, or 99% of one form of the compound, e.g., the S-enantiomer. In other words such compounds or compositions contain an enantiomeric excess of the S enantiomer over the R enantiomer.

The compounds described herein may also contain unnatural proportions of atomic isotopes at one or more of the atoms that constitute such compounds. For example, the compounds may be radiolabeled with radioactive isotopes, such as for example deuterium ($^2$H), tritium ($^3$H), carbon-13 ($^{13}$C), or carbon-14 ($^{14}$C). All isotopic variations of the compounds disclosed herein, whether radioactive or not, are intended to be encompassed within the scope of the present invention. In addition, all tautomeric forms of the compounds described herein are intended to be within the scope of the invention.

The compound can be useful as the free base or as a salt. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19.)

Certain compounds disclosed herein can exist in unsolvated forms as well as solvated forms, including hydrated forms. In general, the solvated forms are equivalent to unsolvated forms and are encompassed within the scope of the present invention. Certain compounds disclosed herein may exist in multiple crystalline or amorphous forms. In general, all physical forms are equivalent for the uses contemplated by the present invention and are intended to be within the scope of the present invention.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably includes humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route.

As used herein, the term "treating" includes any effect, e.g., lessening, reducing, modulating, ameliorating or eliminating, that results in the improvement of the condition, disease, disorder, and the like, or ameliorating a symptom thereof.

Compounds

In one embodiment, the invention provides a compound having structural formula I:

(I)

or a pharmaceutically acceptable salt or a tautomer thereof, wherein:
each $R^4$ is independently selected from —C(O)N($R^2$)($R^2$), —$C_1$-$C_4$ alkyl, —CN, —($C_0$-$C_4$ alkylene)-N($R^2$)($R^2$), —O—($C_1$-$C_4$ alkylene)-O—($C_1$-$C_3$ alkyl), —($C_1$-$C_4$ alkylene)-O—($C_1$-$C_3$ alkyl), or —O—($C_0$-$C_4$ alkylene)-($R^1$), wherein $R^1$ is selected from —$C_1$-$C_4$ alkyl and heterocyclyl;
each $R^2$ is independently selected from hydrogen and unsubstituted $C_1$-$C_4$ alkyl
each $R^6$ is independently selected from —$C_1$-$C_4$ alkyl or two $R^6$ bound to the same carbon atom are taken together to form oxo, or two $R^6$ bound to different carbon atoms are taken together to form methylene, ethane-1,2-diyl, or propane-1,2-diyl forming a ring that is bridged to the piperazine-1,4-diyl portion of the compound;
each $R^8$ is independently selected from halo, —OH, —N($R^2$)($R^2$), $C_1$-$C_4$ alkyl, and —O—($C_1$-$C_4$ alkyl);
L is selected from a bond, —($C_1$-$C_4$ alkylene)-, —O—, —S—, —$SO_2$—, —N($R^2$)—, —O—($C_1$-$C_4$ alkylene)-, —($C_1$-$C_4$ alkylene)-O—, —($C_1$-$C_4$ alkylene)-N($R^2$)—, —N($R^2$)—($C_1$-$C_4$ alkylene)-, —N($R^2$)—CO—($C_1$-$C_4$ alkylene)-, —CO—N($R^2$)—($C_1$-$C_4$ alkylene)-;
n is 0, 1, 2, or 3;
m is 0, 1, 2, 3, or 4;
p is 0, 1, or 2;
q is 0, 1, 2, or 3;
ring A is monocyclic or bicyclic aryl, heteroaryl, carbocyclyl or heterocyclyl;
each $R^{10}$ is independently selected from halo; —OH, —CN, —C(O)N($R^2$)($R^2$), $C_1$-$C_4$ alkyl, —O—($C_1$-$C_4$ alkyl), or heterocyclyl, or two $R^{1o}$ bound to adjacent ring carbon atoms are taken together to form methylenedioxy;
wherein unless otherwise specified any alkyl, or alkylene portion of the compound is optionally substituted.

In some embodiments, the compound of Formula I is not

In certain embodiments of the compound of Formula I, any alkyl, or alkylene portion of the compound is optionally and independently substituted with one or more substituents independently selected from halo, —OH, $C_1$-$C_4$ alkyl, $C_1$-$C_4$ haloalkyl, —O—($C_1$-$C_4$ alkyl), or =O; and any heterocyclyl portion of the compound is optionally and independently substituted with one or more substituents independently selected from halo, —OH, $C_1$-$C_4$ alkyl, $C_1$-$C_4$ haloalkyl, —O—($C_1$-$C_4$ alkyl), or =O.

In certain embodiments of the compound of Formula I, each $R^4$ is independently selected from —C(O)N($R^2$)($R^2$), —O—($C_1$-$C_4$ alkylene)-O—($C_1$-$C_3$ alkyl), and —O—($C_0$-$C_4$ alkylene)-($R^1$), wherein:
$R^1$ is selected from —$C_1$-$C_4$ alkyl, and a saturated heterocyclyl;
each $R^2$ is independently selected from hydrogen and methyl;
each alkyl or alkylene is optionally substituted with one or more substituents independently selected from halo, —OH and —O($C_1$-$C_3$ alkyl);
the saturated heterocyclyl is optionally substituted on a substitutable ring nitrogen with methyl; and
the saturated heterocyclyl is optionally substituted on a substitutable ring carbon with with one or more substituents independently selected from methyl, halo, —OH.

In one aspect of the above embodiments, each $R^4$ is independently selected from C(O)NH$_2$, —OCF$_2$, —OCH$_2$CH$_3$, —OCH$_3$, 1-methyl-4-fluoropiperidin-4-ylmethoxy, 1-(2-hydroxyethyl)-piperidin-4-ylmethoxy, 1-(2-hydroxyethyl)-piperidin-4-yloxy, 1-(2-hydroxyethyl)-pyrrolidin-3-yloxy, 1-methylazetidin-3-ylmethoxy, 1-methylpiperidin-3-ylethoxy, 1-methylpiperidin-3-ylmethoxy, 1-methylpiperidin-4-ylmethoxy, 1-methylpiperidin-4-yloxy, 1-methylpyrrolidin-3-ylmethoxy, 1-methylpyrrolidin-3-yloxy, 2,3-dihydroxypropoxy, 2-oxopiperidin-4-ylmethoxy, 2-oxopyrrolidin-1-ylethoxy, 3-methyloxetan-3-ylmethoxy, 4-methylmorpholin-2-ylmethoxy, 4-methylpiperazin-1-ylethoxy, 4-methylpiperazin-1-ylpropoxy, azetidin-3-ylmethoxy, methoxyethoxy, morpholin-2-ylmethoxy, piperidin-1-ylpropoxy, piperidin-3-ylmethoxy, piperidin-4-ylmethoxy, piperidin-4-yloxy, pyrrolidin-1-ylpropoxy, pyrrolidin-3-ylmethoxy, and pyrrolidin-3-yloxy.

In a more specific aspect of these embodiments, each $R^4$ is independently selected from OCH$_2$CH$_3$, OCH$_3$, 1-(2-hydroxyethyl)-piperidin-4-ylmethoxy, 1-(2-hydroxyethyl)-piperidin-4-yloxy, 1-(2-hydroxyethyl)-pyrrolidin-3-yloxy, 1-methyl-4-fluoropiperidin-4-ylmethoxy, 1-methylazetidin-3-ylmethoxy, 1-methylpiperidin-3-ylethoxy, 1-methylpiperidin-3-ylmethoxy, 1-methylpiperidin-4-ylmethoxy, 1-methylpiperidin-4-yloxy, 1-methylpyrrolidin-3-ylmethoxy, 1-methylpyrrolidin-3-yloxy, 2,3-dihydroxypropoxy, 2-oxopiperidin-4-ylmethoxy, 2-oxopyrrolidin-1-yleithoxy, 3-methyloxetan-3-ylmethoxy, 4-methylmorpholin-2-ylmethoxy, 4-methylpiperazin-1-ylethoxy, 4-methylpiperazin-1-ylpropoxy, azetidin-3-ylmethoxy, methoxyethoxy, morpholin-2-ylmethoxy, piperidin-1-ylpropoxy, piperidin-3-ylmethoxy, piperidin-4-ylmethoxy, piperidin-4-yloxy, pyrrolidin-3-ylmethoxy, and pyrrolidin-3-yloxy.

In some embodiments of the compound of Formula I, each $R^6$ is independently selected from $C_1$-$C_4$ alkyl, =O, or two $R^6$ on non-adjacent carbon ring atoms are taken together to form methylene, ethane-1,2-diyl, or propane-1,3-diyl thereby forming a ring that is bridged to the piperazine-1,4-diyl portion of the compound. In the interest of clarity, examples of the bridged rings so formed are depicted below:

Two $R^6$ form methylene:

Two R⁶ form ethane-1,2-diyl:

Two R⁶ form propane-1,3-diyl:

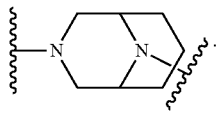 [SMILES: *N1CC2CCCC(C1)N2*]

In a more specific aspect of the above embodiments, each R⁶ is independently methyl or =O, or two R⁶ non-adjacent carbon ring atoms are taken together to form an ethane-1, 2-diyl thereby forming a ring that is bridged to the piperazine-1,4-diyl portion of the compound.

In certain embodiments of the compound of Formula I each R⁸ is independently selected from =O and —NH₂.

In certain embodiments of the compound of Formula I each R¹⁰ is independently selected from OH, —OCH₃, —F, —CH₃, —CN, —C(O)NH₂, —OCF₂, and —Cl.

In certain embodiments of the compound of Formula I, L is selected from a bond, —CH₂—, —CH₂CH₂, NH, O, S, CH₂O—*, —OCH₂—*, —OCH(CH₃)—*, —N(CH₃) CH₂—*, —NHCH₂—*, —NHC(O)CH₂—*, —C(O) NH—*, —NHCH(CH₃)—*, and —SO₂—, wherein "*" represents a portion of L bound to ring A. In one aspect of these embodiments, L is selected from —CH₂—, —CH₂CH₂—, —NH—, —O—, —S—, —CH₂O—*, —N(CH₃)CH₂—*, —OCH(CH₃)—*, and —OCH (CH₃)—*. In a more specific aspect of these embodiments, L is —CH₂—.

In certain embodiments of the compound of Formula I, ring A is selected from phenyl, thiophenyl, indolinyl, 1,2,3, 4-tetrahydroquinoline, pyridinyl, thiophenyl, and C₃-C₆ cycloalkyl. In one aspect of these embodiments, ring A is selected from phenyl, and thiophen-2-yl. In a more specific aspect, ring A is phenyl.

In certain embodiment, the compound of the invention has structural formula II:

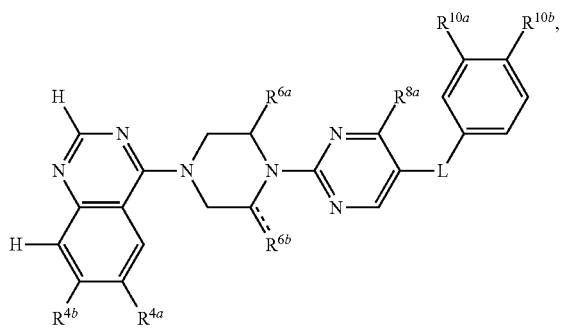

or a pharmaceutically acceptable salt or tautomer thereof, wherein:
one of R⁴ᵃ or R⁴ᵇ is selected from hydrogen, —O—CH₃, —O—CH₂CH₃ and —O—CH₂CH₂—O—CH₃;
the other of R⁴ᵃ or R⁴ᵇ is selected from —O—CH₃, —O—CH₂CH₃, —O—CH₂CH₂—O—CH₃ and —(C₀-C₄ alkylene)-(saturated heterocyclyl), wherein:

the saturated heterocyclyl is optionally substituted on a substitutable ring nitrogen with methyl; and
the saturated heterocyclyl is optionally substituted on a substitutable ring carbon with one or more substituents independently selected from methyl, halo, and —OH;
R⁶ᵃ is hydrogen;
R⁶ᵇ is selected from hydrogen, =O, and —CH₃; or
R⁶ᵃ and R⁶ᵇ are taken together with the carbon atoms to which they are bound to form a cyclobutyl fused to the piperazine-1,4-diyl ring;
R⁸ᵃ is selected from hydrogen, —NH₂ and —OH;
L is selected from —CH₂—, —CH₂CH₂—, —NH—, —O—, —S—, —CH₂O—*, —N(CH₃)CH₂—*, —OCH (CH₃)—*, and —OCH(CH₃)—*;
R¹⁰ᵃ is selected from hydrogen, —OCH₃, —C(O)NH₂ and halo; and
R¹⁰ᵇ is selected from hydrogen, —OCH₃, —OCF₂, halo, —CH₃, CN, and OH.

In some embodiments of Formula II:
one of R⁴ᵃ or R⁴ᵇ is selected from hydrogen, —O—CH₃, —O—CH₂CH₃ and —O—CH₂CH₂—O—CH₃;
the other of R⁴ᵃ or R⁴ᵇ is selected from —O—CH₃, —O—CH₂CH₃, —O—CH₂CH₂—O—CH₃, 1-(2-hydroxyethyl)-piperidin-4-ylmethoxy, 1-(2-hydroxyethyl)-piperidin-4-yloxy, 1-(2-hydroxyethyl)-pyrrolidin-3-yloxy, 1-methyl-4-fluoropiperidin-4-ylmethoxy, 1-methylazetidin-3-ylmethoxy, 1-methylpiperidin-3-ylethoxy, 1-methylpiperidin-3-ylmethoxy, 1-methylpiperidin-4-ylmethoxy, 1-methylpiperidin-4-yloxy, 1-methylpyrrolidin-3-ylmethoxy, 1-methylpyrrolidin-3-yloxy, 2,3-dihydroxypropoxy, 2-oxopiperidin-4-ylmethoxy, 2-oxopyrrolidin-1-yleithoxy, 3-methyloxetan-3-ylmethoxy, 4-methylmorpholin-2-ylmethoxy, 4-methylpiperazin-1-ylethoxy, 4-methylpiperazin-1-ylpropoxy, azetidin-3-ylmethoxy, morpholin-2-ylmethoxy, piperidin-1-ylpropoxy, piperidin-3-ylmethoxy, piperidin-4-ylmethoxy, piperidin-4-yloxy, pyrrolidin-3-ylmethoxy, and pyrrolidin-3-yloxy;
R¹⁰ᵃ is selected from hydrogen, —OCH₃, and fluoro; and
R¹⁰ᵇ is selected from hydrogen, —OCH₃, —OCF₂, fluoro, chloro, —CH₃, CN, OH, and —C(O)NH₂.

In still another embodiment, the invention provides a compound having structural formula III:

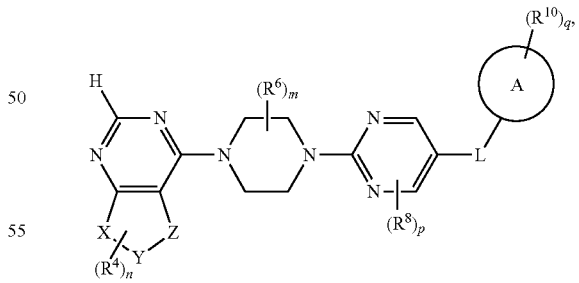

or a pharmaceutically acceptable salt or tautomer thereof, wherein
each of X, Y, and Z is independently, C or N, each of which may be attached to one or more R⁴;
each R⁴ is independently selected from —C(O)N(R²) (R²), —C₁-C₄ alkyl, —CN, —(C₀-C₄ alkylene)-N(R²)(R²), —O—(C₁-C₄ alkylene)-O—(C₁-C₃ alkyl), —(C₁-C₄ alkylene)-O—(C₁-C₃ alkyl), or —O—(C₀-C₄ alkylene)-(R¹), wherein R¹ is selected from —C₁-C₄ alkyl and heterocyclyl;

each $R^2$ is independently selected from hydrogen and unsubstituted $C_1$-$C_4$ alkyl;

each $R^6$ is independently selected from —$C_1$-$C_4$ alkyl or two $R^6$ bound to the same carbon atom are taken together to form oxo, or two $R^6$ bound to different carbon atoms are taken together to form methylene, ethane-1,2-diyl or propane-1,3-diyl thereby forming a ring that is bridged to the piperazine-1,4-diyl portion of the compound;

each $R^8$ is independently selected from halo, —OH, —N($R^2$)($R^2$), $C_1$-$C_4$ alkyl, and —O—($C_1$-$C_4$ alkyl);

L is selected from a bond, —($C_1$-$C_4$ alkylene)-, —O—, —S—, —$SO_2$—, —N($R^2$)—, —O—($C_1$-$C_4$ alkylene)-, —($C_1$-$C_4$ alkylene)-O—, —($C_1$-$C_4$ alkylene)-N($R^2$)—, —N($R^2$)—($C_1$-$C_4$ alkylene)-, —N($R^2$)—CO—($C_1$-$C_4$ alkylene)-, —CO—N($R^2$)— ($C_1$-$C_4$ alkylene)-;

n is 0, 1, 2, or 3;

m is 0, 1, 2, 3, or 4;

p is 0, 1, or 2;

q is 0, 1, 2, or 3;

ring A is monocyclic or bicyclic aryl, heteroaryl, carbocyclyl or heterocyclyl;

each $R^{10}$ is independently selected from halo; —OH, —CN, —C(O)N($R^2$)($R^2$), $C_1$-$C_4$ alkyl, —O—($C_1$-$C_4$ alkyl), or heterocyclyl, or two $R^{1o}$ bound to adjacent ring carbon atoms are taken together to form methylenedioxy; and wherein unless otherwise specified any alkyl, or alkylene portion of the compound is optionally substituted.

Indications

The compounds described herein can be useful for treating conditions associated with aberrant Kit activity. Activating mutations in Kit are found in multiple indications, including systemic mastocytosis, GIST (gastrointestinal stromal tumors), AML (acute myeloid leukemia), melanoma, and seminoma.

Mastocytosis refers to a group of disorders characterized by excessive mast cell accumulation in one tissue, or in multiple tissues. Mastocytosis is subdivided into two groups of disorders: (1) cutaneous mastocytosis (CM) describes forms that are limited to the skin; and (2) systemic mastocytosis (SM) describes forms in which mast cells infiltrate extracutaneous organs, with or without skin involvement. SM is further subdivided into four forms: indolent (ISM), smoldering (SSM), aggressive (ASM), SM with associated hemotologic non-mast cell lineage disease (SM-AHNMD), and mast cell leukemia (MCL).

Diagnosis of systemic mastocytosis is based on histological and cytological study of bone marrow showing infiltration by mast cells of frequently atypical morphology, which frequently abnormally express non-mast cell markers (CD25 and/or CD2). An elevated level of serum tryptase above 20 ng/mL or the presence of an activating mutation of Kit can confirm the diagnosis. The extent of the proliferation of mast cells can be analyzed using medical imaging (radiography, ultrasound, CT scanning).

Activating mutations at the D816 position are found in the vast majority of mastocytosis cases, with the most common mutations being D816V and D816H, and D816Y. The D816V mutation is found in the activation loop of the kinase domain, and leads to constitutive activation.

The compounds described herein may also be useful to treat GIST. Complete surgical resection remains the principal treatment of choice for patients with a primary GIST. Surgery is effective in approximately 50% of patients with GIST. Of the remaining patients, tumor recurrence is frequent. Primary treatment with a Kit inhibitor such as imatinib has also been shown to be sufficient for initial treatment. However, resistance to imatinib occurs within months through somatic mutation. These secondary imatinib resistant mutations are most frequently located on exon 11, 13, 14, 17 or 18. Sunitinib is the standard of care second line treatment for most imatinib resistant tumors and is effective for those containing mutations in exons 11, 13 and 14. However, secondary kit mutations in exons 17 and 18 are resistant to sunitinib treatment and furthermore, tumors containing tertiary resistance mutations in exon 17 and 18 emerge several months after sunitinib treatment. Regorafenib has shown promising results in a phase 3 clinical trial of imatinib, sunitinib resistant GISTs with activity against several exon 17 and 18 mutations, with the exception of the D816 mutant which remains refractory to all treatments. Regorafenib has been approved for 3rd line GIST treatment.

The compounds described herein may also be useful in treating AML. Some AML patients harbor Kit mutations as well, with the majority of these mutations at the D816 position.

In addition, mutations in Kit have been linked to Ewing's sarcoma, DLBCL (diffuse large B cell lymphoma), dysgerminoma, MDS (myelodysplastic syndrome), NKTCL (nasal NK/T-cell lymphoma), and CMML (chronic myelomonocytic leukemia).

Pharmaceutical Compositions

While it is possible for a compound disclosed herein to be administered alone, it is preferable to administer the compound as a pharmaceutical formulation, where the compound is combined with one or more pharmaceutically acceptable excipients or carriers. The compounds disclosed herein may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21)

cyclodextrins such as Captisol®; and (22) other non-toxic compatible substances employed in pharmaceutical formulations.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Solid dosage forms (e.g., capsules, tablets, pills, dragees, powders, granules and the like) can include one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

Liquid dosage forms can include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

When the compounds disclosed herein are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The formulations can be administered topically, orally, transdermally, rectally, vaginally, parentally, intranasally, intrapulmonary, intraocularly, intravenously, intramuscularly, intraarterially, intrathecally, intracapsularly, intradermally, intraperitoneally, subcutaneously, subcuticularly, or by inhalation.

Dosages

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound disclosed herein employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day. If desired, the effective daily dose of the active compound may be administered as two, three, four, five, six or more sub-doses administered separately at appropriate intervals throughout the day, optionally, in unit dosage forms. In some embodiments, the dose will be 1-20, or 5-10 mg per kilogram of body weight, administered twice daily.

EXAMPLES

The following examples are intended to be illustrative, and are not meant in any way to be limiting.

Example 1

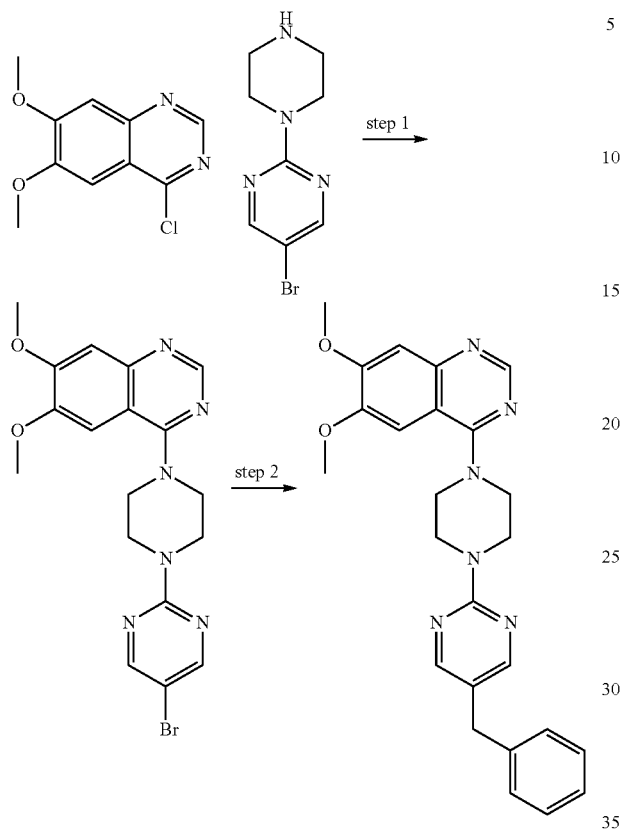

Step 1: In a 75 mL sealed vessel, 4-chloro-6,7-dimethoxyquinazoline (1 g, 4.45 mmol) and 5-bromo-2-(piperazin-1-yl)pyrimidine (1.19 g, 4.89 mmol) were dissolved in isopropanol (30 mL) and triethylamine (0.745 mL, 5.34 mmol). The reaction mixture was stirred at 90 degrees Celsius for 15 hours. The mixture was then diluted with water and the resulting solids were filtered, washed with water and dried to give the desired product 4-(4-(5-bromopyrimidin-2-yl)piperazin-1-yl)-6,7-dimethoxyquinazoline as a white solid (1.85 g). This material was used in Step 2 without further purification.

Step 2: In a sealable reaction tube, 4-(4-(5-bromopyrimidin-2-yl)piperazin-1-yl)-6,7-dimethoxyquinazoline (50 mg, 0.116 mmol), 2-benzyl-4,4,5,5-tetramethyl-1,3,2-dioxaborolane (0.031 mL, 0.14 mmol), potassium carbonate (48 mg, 0.35 mmol) and Pd(PPh$_3$)$_4$ (13.5 mg, 0.0116 mmol), were combined with 1/1 THF and water (1.3 mL) in a N$_2$ atmosphere and heated to 100 degrees Celsius for 15 hours. The cooled reaction mixture was diluted with ethyl acetate and filtered through a celite plug. The residue was purified by silica gel chromatography (0-10% methanol/methylene chloride) followed by preparative thin layer chromatography eluting with 1/1 acetone in dichloromethane. The desired product was excised and extracted with 10% methanol in dichloromethane. After drying on high vacuum, the product 4-(4-(5-benzylpyrimidin-2-yl)piperazin-1-yl)-6,7-dimethoxyquinazoline was obtained as an off-white solid (25 mg, 49% yield).

Example 2

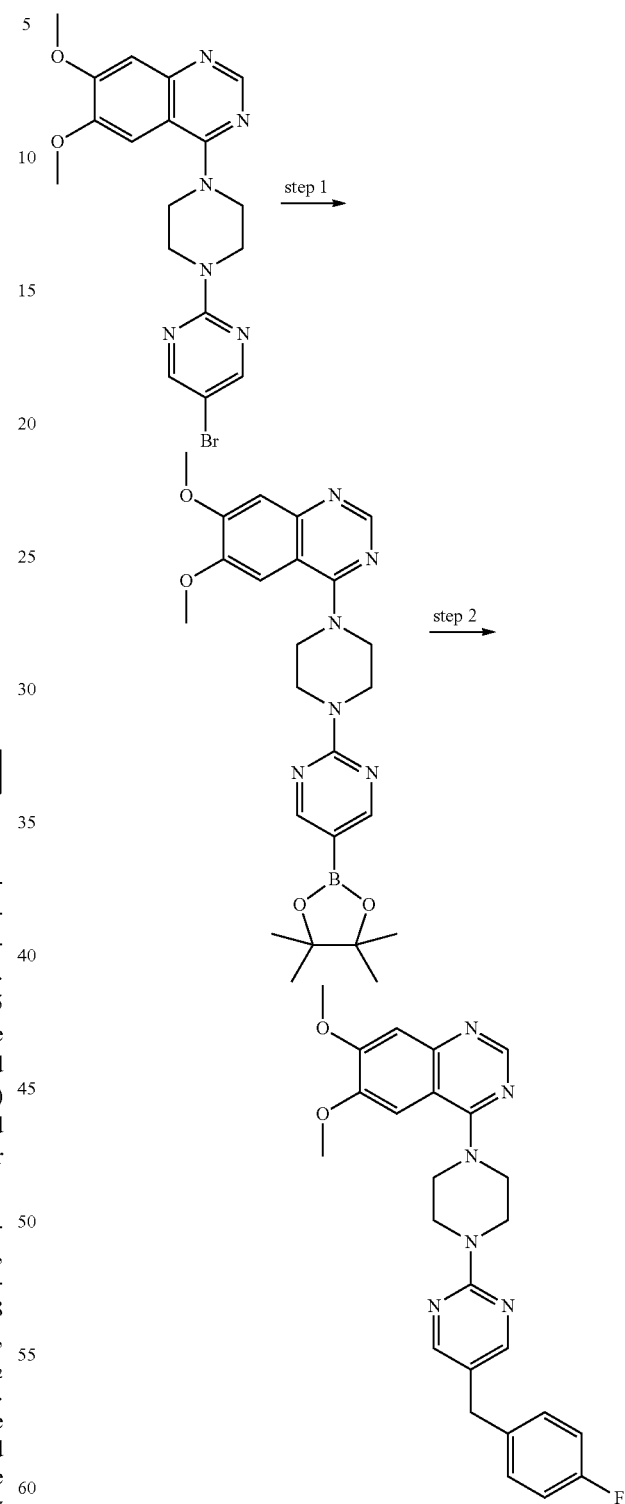

Step 1: In a sealable reaction tube, 4-(4-(5-bromopyrimidin-2-yl)piperazin-1-yl)-6,7-dimethoxyquinazoline (0.4 g, 0.93 mmol), 4,4,4',4',5,5,5',5'-octamethyl-2,2'-bi(1,3,2-dioxaborolane) (0.425 g, 1.8 mmol), potassium acetate (0.46 g, 4.65 mmol) and [1,1'-Bis(diphenylphosphino)ferrocene]

dichloropalladium(II), complex with dichloromethane (38 mg, 0.0465 mmol), were combined in anhydrous DMSO (4.65 mL) in a N₂ atmosphere and heated to 80 degrees Celsius for 15 hours. The mixture was then diluted with water and the resulting solids were filtered, washed with water and dried to give the desired product 6,7-dimethoxy-4-(4-(5-(4,4,5,5-tetramethyl-1,3,2-dioxaborolan-2-yl)pyrimidin-2-yl)piperazin-1-yl)quinazoline as a pale brown solid (0.417 g).

Step 2: In a sealable reaction tube, 6,7-dimethoxy-4-(4-(5-(4,4,5,5-tetramethyl-1,3,2-dioxaborolan-2-yl)pyrimidin-2-yl)piperazin-1-yl)quinazoline (35 mg, 0.073 mmol), 1-(bromomethyl)-4-fluorobenzene (0.011 mL, 0.088 mmol), cesium carbonate (71 mg, 0.219 mmol) and Pd(ᵗBu₃)₃ (5 mg, 0.009 mmol), were combined in 2/1 THF and water (1.2 mL) in a N₂ atmosphere and heated to 140 degrees Celsius for 15 minutes in a MW reactor. The cooled reaction mixture was diluted with ethyl acetate and filtered through a celite plug. The residue was purified by silica gel chromatography (0-6% methanol/methylene chloride). After drying on high vacuum, the product 4-(4-(5-(4-fluorobenzyl)pyrimidin-2-yl)piperazin-1-yl)-6,7-dimethoxyquinazoline was obtained as an off-white solid (21 mg, 64% yield).

Example 3

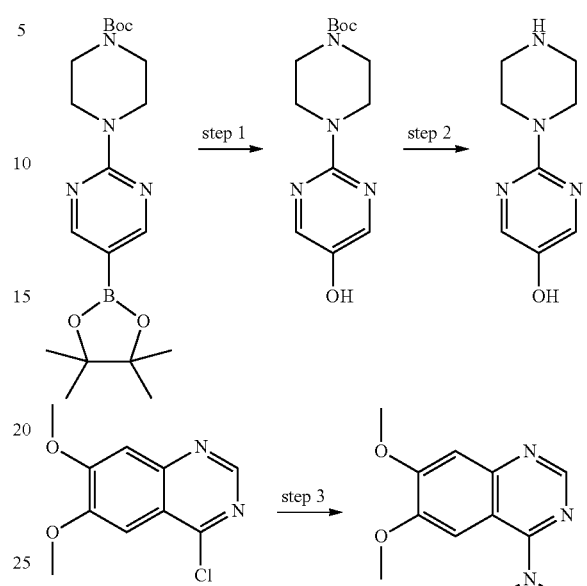

In a sealable reaction tube, 4-(4-(5-bromopyrimidin-2-yl)piperazin-1-yl)-6,7-dimethoxyquinazoline (50 mg, 0.12 mmol), benzyl alcohol (0.12 mL, 1.163 mmol), copper iodide (2.2 mg, 0.012 mmol), 1,10-phenanthroline (4.2 mg, 0.023 mmol), and cesium carbonate (57 mg, 0.174 mmol), were combined in anhydrous toluene (0.5 mL) in a N₂ atmosphere and heated to 110 degrees Celsius for 48 hours. The cooled reaction mixture was diluted with ethyl acetate and filtered through a celite plug. The residue was purified by silica gel chromatography (0-6% methanol/methylene chloride). After drying on high vacuum, the product 4-(4-(5-(benzyloxy)pyrimidin-2-yl)piperazin-1-yl)-6,7-dimethoxyquinazoline was obtained as an off-white solid (37 mg, 67% yield).

Example 4

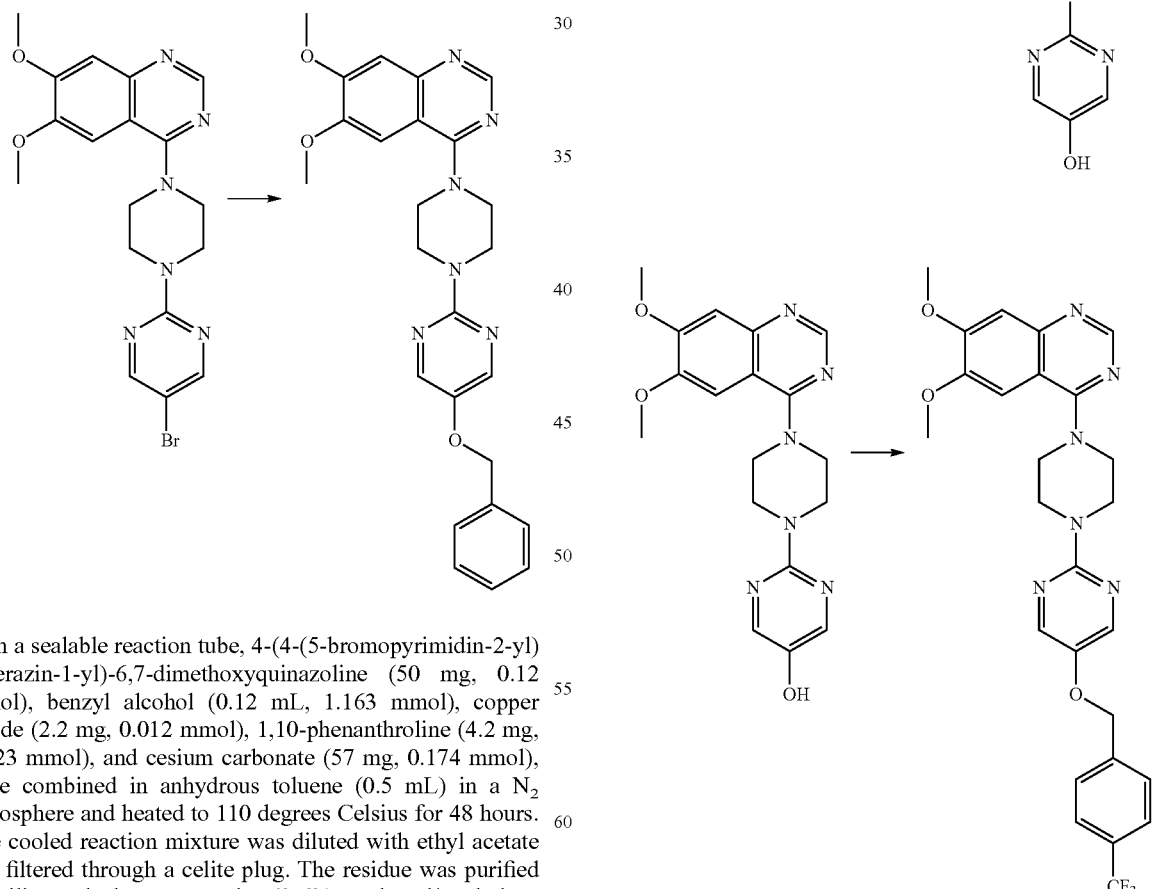

Step 1: In a vessel, tert-butyl 4-(5-(4,4,5,5-tetramethyl-1,3,2-dioxaborolan-2-yl)pyrimidin-2-yl)piperazine-1-carboxylate (0.5 g, 1.28 mmol) and 35% aqueous hydrogen peroxide (1.2 mL, 12.8 mmol) were dissolved in tetrahydrofuran (10 mL). The reaction mixture was stirred at room temperature for 1.5 hours. The mixture diluted to 40 mL with aqueous saturated sodium thiosulfate solution and then extracted with ethylacetate to give the desired product tert-butyl 4-(5-hydroxypyrimidin-2-yl)piperazine-1-carboxylate as a brown oil. This material was used in Step 2 without further purification.

Step 2: In a vessel, tert-butyl 4-(5-hydroxypyrimidin-2-yl)piperazine-1-carboxylate from the previous step (1.28 mmol) and 4M hydrogen chloric acid in dioxane (4 mL, 12.8 mmol) were dissolved in 2/1 mixture of methanol and dichloromethane (10 mL). The reaction mixture was stirred at room temperature for 1.5 hours. The mixture was then concentrated to dryness to give the desired product 2-(piperazin-1-yl)pyrimidin-5-ol as a brown solid. This material was used in Step 3 without further purification.

Step 3: In a microwave vessel, 2-(piperazin-1-yl)pyrimidin-5-ol from the previous step (1.28 mmol) and 4-chloro-6,7-dimethoxyquinazoline (0.29 g, 1.28 mmol) were dissolved in isopropanol (6 mL) and diisopropylethyl amine (0.23 mL, 1.41 mmol). The reaction mixture was heated at 140 degrees Celsius in a microwave reactor for 30 minutes. The mixture was then diluted with hexanes and the resulting solids were filtered, washed with hexanes and dried to give the desired product 2-(4-(6,7-dimethoxyquinazolin-4-yl)piperazin-1-yl)pyrimidin-5-ol as a brown solid (0.42 g). This material was used in the next step without further purification.

Step 4: In a dry vessel, 2-(4-(6,7-dimethoxyquinazolin-4-yl)piperazin-1-yl)pyrimidin-5-ol (35 mg, 0.095 mmol) (see method F), 1-(bromomethyl)-4-(trifluoromethyl)benzene (25 mg, 0.105 mmol), and potassium carbonate (20 mg, 0.142 mmol) were dissolved in dimethylformamide (1 mL). The reaction mixture was stirred at room temperature for 15 hours. The mixture was then diluted with water and the resulting solids were filtered, washed with water and dried. The residue was purified by silica gel chromatography (0-6% methanol/methylene chloride. After drying on high vacuum, the product 6,7-dimethoxy-4-(4-(5-((4-(trifluoromethyl)benzyl)oxy)pyrimidin-2-yl)piperazin-1-yl)quinazoline was obtained as a white solid (18 mg, 36% yield).

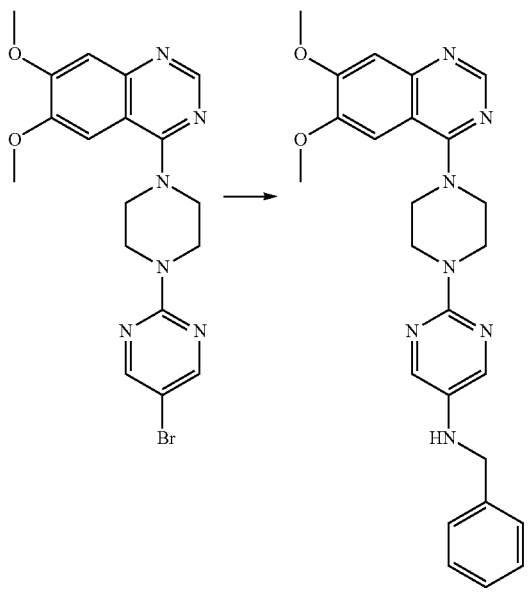 [SMILES: COc1cc2ncnc(N3CCN(c4ncc(Br)cn4)CC3)c2cc1OC ; COc1cc2ncnc(N3CCN(c4ncc(NCc5ccccc5)cn4)CC3)c2cc1OC]

Example 5

In a sealable reaction tube, 4-(4-(5-bromopyrimidin-2-yl)piperazin-1-yl)-6,7-dimethoxyquinazoline (75 mg, 0.174 mmol), benzyl amine (0.19 mL, 1.74 mmol), copper iodide (3.5 mg, 0.017 mmol), L-proline (4.0 mg, 0.035 mmol), and potassium phosphate (74 mg, 0.35 mmol), were combined in anhydrous dimethylsulfoxide (0.87 mL) in a $N_2$ atmosphere and heated to 80 degrees Celsius for 15 hours. The cooled reaction mixture was diluted with ethyl acetate and filtered through a celite plug. The residue dissolved in ethylacetate was washed multiple times with water. The residue was purified by silica gel chromatography (0-6% methanol/methylene chloride. After drying on high vacuum, the product N-benzyl-2-(4-(6,7-dimethoxyquinazolin-4-yl)piperazin-1-yl)pyrimidin-5-amine was obtained as an off-white solid (38 mg, 48% yield).

Example 6

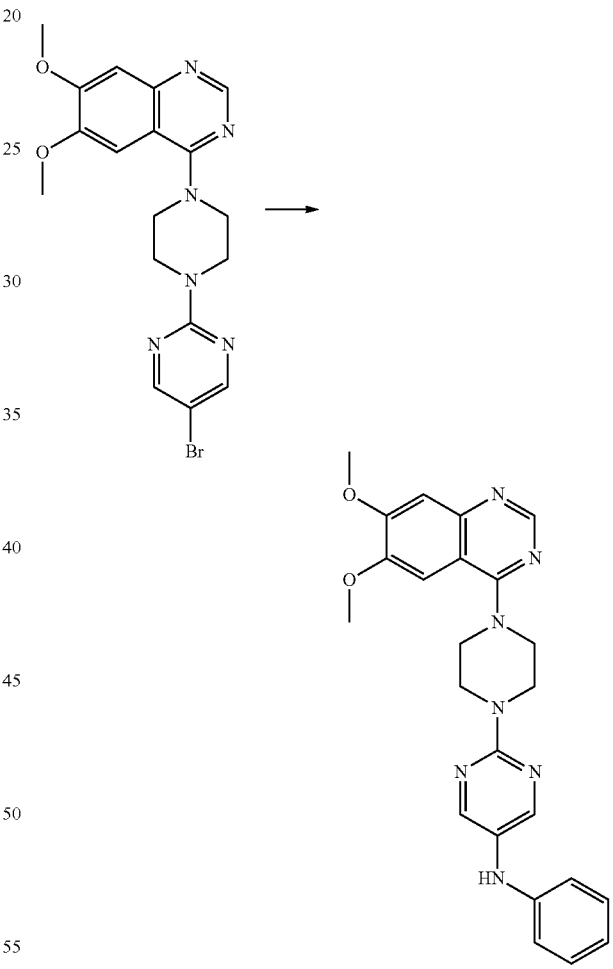

In a sealable reaction tube, 4-(4-(5-bromopyrimidin-2-yl)piperazin-1-yl)-6,7-dimethoxyquinazoline (50 mg, 0.116 mmol), aniline (0.016 mL, 0.174 mmol), potassium carbonate (25 mg, 0.174 mmol), chloro{[BrettPhos][2-(2-aminoethylphenyl]palladium(II)]}/[BrettPhos]admixture (molar PdP/P=1:1) (3.5 mg, 0.002 mmol), were combined in tert-butanol (0.8 mL) in a $N_2$ atmosphere and heated to 100 degrees Celsius for 15 hours. The cooled reaction mixture was diluted with ethyl acetate and filtered through a celite plug. The residue was purified by silica gel chromatography (0-6% methanol/methylene chloride. After drying on high vacuum, the product 2-(4-(6,7-dimethoxyquinazolin-4-yl)piperazin-1-yl)-N-phenylpyrimidin-5-amine was obtained as an off-white solid (45 mg, 88% yield).

Example 7

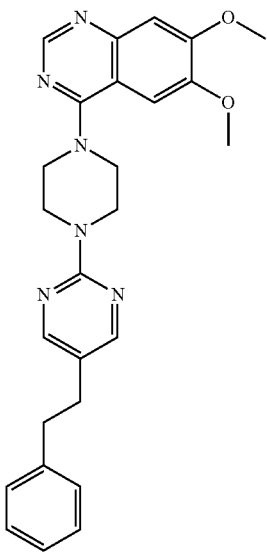 [SMILES: COc1cc2ncnc(N3CCN(c4ncc(CCc5ccccc5)cn4)CC3)c2cc1OC]

To a sealable vessel was added 4-(4-(5-bromopyrimidin-2-yl)piperazin-1-yl)-6,7-dimethoxyquinazoline (43 mg, 0.1 mmol), Potassium (2-phenylethyl)trifluoroborate (25 mg, 0.12 mmol), RuPhos (4.7 mg, 10 mol %), Pd(OAc)$_2$ (1.1 mg, 5 mol %), and potassium carbonate (41 mg, 0.3 mmol). The reaction vessel was sealed and purged with nitrogen. 0.9 mL of toluene was added followed by 0.1 mL water and the reaction vessel heated in an oilbath at 80° C. for 4 hours. The reaction mixture was cooled and diluted with EtOAc and the organic layer filtered through a plug of sodium sulfate. Evaporation gave the crude product which was subjected to flash chromatography using a gradient of 40 to 100% EtOAc/Hex. Clean fractions were combined and evaporated to give 37.5 mg (82%) of the referenced compound as a white solid.

Example 8

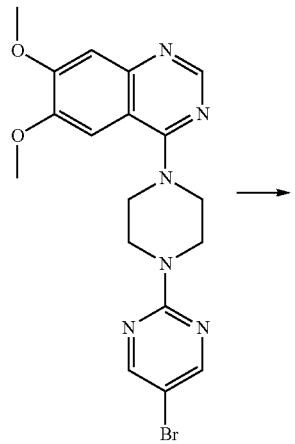

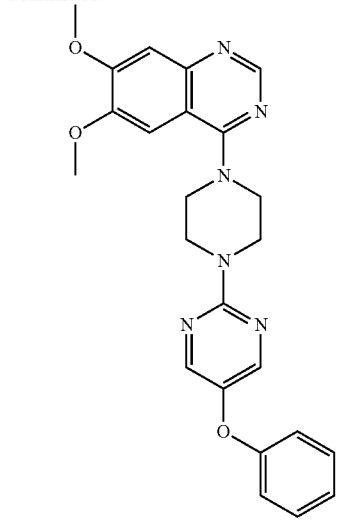

In a microwave vessel, 4-(4-(5-bromopyrimidin-2-yl)piperazin-1-yl)-6,7-dimethoxyquinazoline (50 mg, 0.116 mmol), phenol (22 mg, 0.233 mmol), copper iodide (7.0 mg, 0.035 mmol), 1,10-phenanthroline (11 mg, 0.06 mmol), and cesium carbonate (80 mg, 0.253 mmol), were combined in anhydrous dioxane (0.5 mL) in a N$_2$ atmosphere and heated to 200 degrees Celsius for 1 hour in a microwave reactor. The cooled reaction mixture was diluted with ethyl acetate and filtered through a celite plug. The residue was purified by silica gel chromatography (0-7% methanol/methylene chloride. After drying on high vacuum, the product 6,7-dimethoxy-4-(4-(5-phenoxypyrimidin-2-yl)piperazin-1-yl)quinazoline was obtained as an off-white solid (13.5 mg, 26% yield).

Example 9

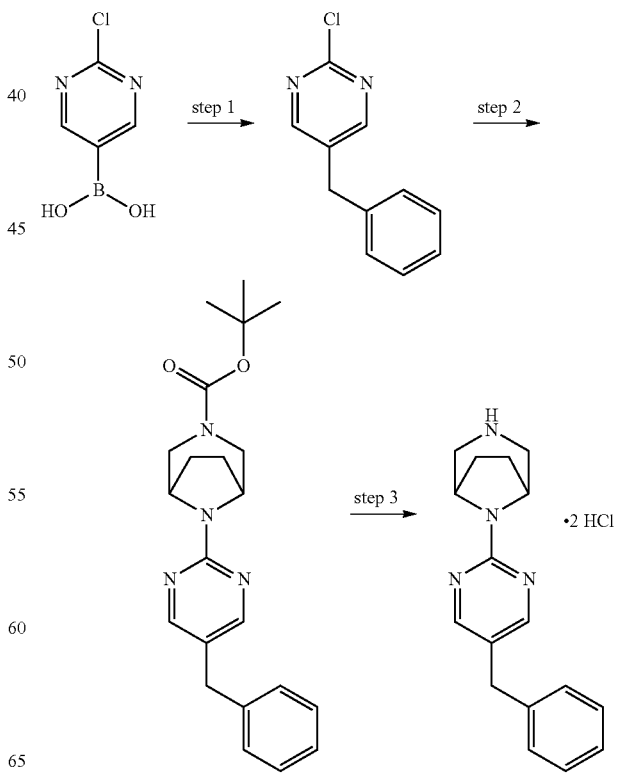

Step 1: To a nitrogen-degassed mixture of (2-chloropyrimidin-5-yl)boronic acid (1.61 g, 10.2 mmol), bis(triphenylphosphine)palladium(II)dichloride (0.36 g, 0.51 mmol), sodium carbonate (3.24 g, 30.6 mmol), water (6.5 mL), and dioxane (16 mL) was added benzyl bromide (1.92 g, 11.2 mmol). The mixture was stirred about 22 hours at 100° C. The reaction mixture was cooled to room temperature, diluted with ethyl acetate (80 mL), and washed with water (60 mL) and then brine (50 mL), then dried over sodium sulfate, filtered, and evaporated under reduced pressure. The crude amber oil was purified by silica gel chromatography with hexanes to 30% ethyl acetate/hexanes gradient to yield the product 5-benzyl-2-chloropyrimidine as an orange oil which solidified upon standing (1.21 g, 58% yield).

Step 2: A mixture of 5-benzyl-2-chloropyrimidine (76 mg, 0.37 mmol), (1R,5S)-tert-butyl 3,8-diazabicyclo[3.2.1]octane-3-carboxylate (94 mg, 0.44 mmol), and triethylamine (149 mg, 1.48 mmol) in 2-propanol (1 mL) was stirred in a sealed tube at 120° for 16 hours. The reaction mixture was cooled to room temperature and the solvents were removed under reduced pressure. The crude residue was treated with water (6 mL), then sonicated and stirred. A light beige solid was isolated by filtration to yield the desired product (1R,5S)-tert-butyl 8-(5-benzylpyrimidin-2-yl)-3,8-diazabicyclo[3.2.1]octane-3-carboxylate (111 mg, 79% yield).

Step 3: A mixture of (1R,5S)-tert-butyl 8-(5-benzylpyrimidin-2-yl)-3,8-diazabicyclo[3.2.1]octane-3-carboxylate (111 mg, 0.291 mmol) in 4N hydrochloric acid/dioxane (1.3 mL) was stirred 2 hours at room temperature. The solvent was removed under reduced pressure. The amber solid was dried under high vacuum to yield the desired product (1R,5S)-8-(5-benzylpyrimidin-2-yl)-3,8-diazabicyclo[3.2.1]octane, assumed to be the di-HCl salt. Since the tare on the vial was lost, the yield was assumed to be quantitative (103 mg).

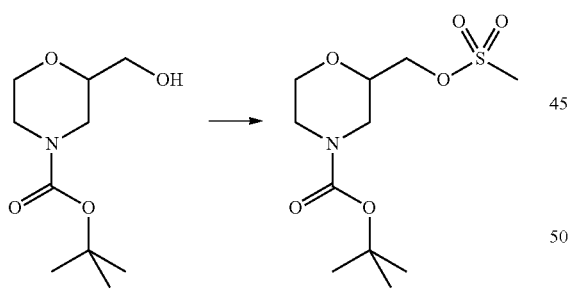

To a stirred 0° C. solution of tert-butyl 2-(hydroxymethyl)morpholine-4-carboxylate (54 mg, 0.25 mmol) and triethylamine (33 mg, 0.33 mmol) in dichloromethane (2 mL) was added methanesulfonyl chloride (29 mg, 0.25 mmol). The reaction mixture was allowed to warm to room temperature and was stirred overnight for a total of 22 hours. The mixture was diluted with dichloromethane (3 mL) and washed with aqueous 2N sodium hydroxide solution (3 mL). The organic layers was dried over sodium sulfate, filtered, concentrated down, and dried under vacuum to yield the desired product tert-butyl 2-(((methylsulfonyl)oxy)methyl)morpholine-4-carboxylate in excess yield. The yield was assumed to be quantitative (74 mg) and was used as is in the next Example.

Example 10

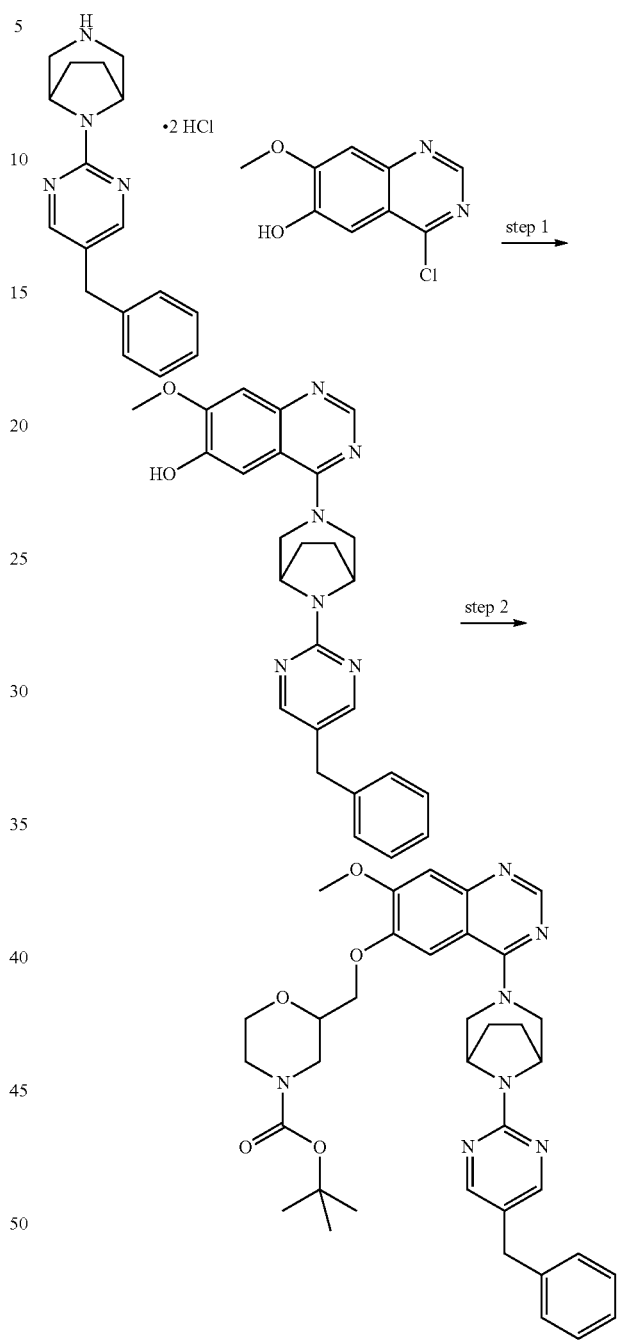

Step 1: A mixture of (1R,5S)-8-(5-benzylpyrimidin-2-yl)-3,8-diazabicyclo[3.2.1]octane di-HCl salt (70 mg, 0.2 mmol), commercially available 4-chloro-6-hydroxy-7-methoxyquinazoline (38 mg, 0.18 mmol) and triethylamine (109 mg, 1.08 mmol) in 2-propanol (1.5 mL) was stirred in a sealed tube at 120° C. for 1.5 hours. The reaction mixture was then cooled to room temperature. An off-white solid was isolated by filtration and dried to yield desired product 4-((1R,5S)-8-(5-benzylpyrimidin-2-yl)-3,8-diazabicyclo[3.2.1]octan-3-yl)-7-methoxyquinazolin-6-ol in slight excess yield (theoretical yield: 82 mg). The crude product probably contained some triethylamine hydrochloride salt and was used as is for the next step. LCMS (M+1)=455.2.

Step 2: A mixture of 4-((1R,5S)-8-(5-benzylpyrimidin-2-yl)-3,8-diazabicyclo[3.2.1]octan-3-yl)-7-methoxyquinazolin-6-ol (46 mg, <0.10 mmol), tert-butyl 2-(((methylsulfonyl)oxy)methyl)morpholine-4-carboxylate (~30 mg, 0.10 mmol), and cesium carbonate (131 mg, 0.40 mmol) in N,N-dimethylformamide (0.3 mL), was stirred in a sealed tube at 85° C. for 4 hours. The reaction mixture was treated with water (~7 mL). A beige solid was isolated by filtration, dried, and purified by silica gel preparative TLC (elution with 10% methanol/dichloromethane) to yield the desired product tert-butyl 2-(((4-((1R,5S)-8-(5-benzylpyrimidin-2-yl)-3,8-diazabicyclo[3.2.1]octan-3-yl)-7-methoxyquinazolin-6-yl)oxy)methyl)morpholine-4-carboxylate as a clear film (44.2 mg, 67%).

Example 11

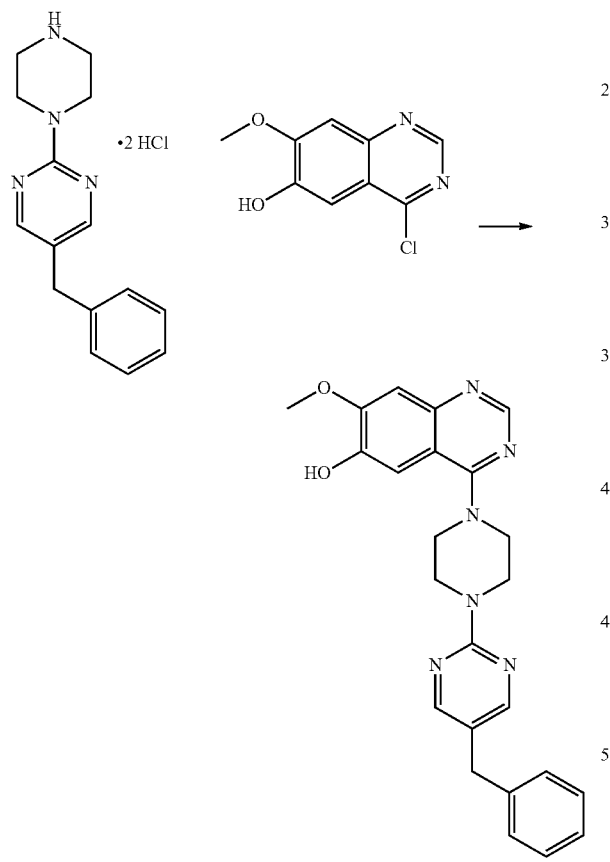

A mixture of 5-benzyl-2-(piperazin-1-yl)pyrimidine di-HCl salt (45 mg, 1.39 mmol), commercially available 4-chloro-6-hydroxy-7-methoxyquinazoline (266 mg, 1.26 mmol) and triethylamine (511 mg, 5.05 mmol) in 2-propanol (4 mL) was stirred in a sealed tube at 120° C. for 6 hours. The reaction mixture was then cooled to room temperature. A beige solid was isolated by filtration and dried to yield desired product 4-(4-(5-benzylpyrimidin-2-yl)piperazin-1-yl)-7-methoxyquinazolin-6-ol in excess yield (683 mg versus theoretical yield of 541 mg). The crude product probably contained some triethylamine hydrochloride salt and was used as is for the next step.

Example 12

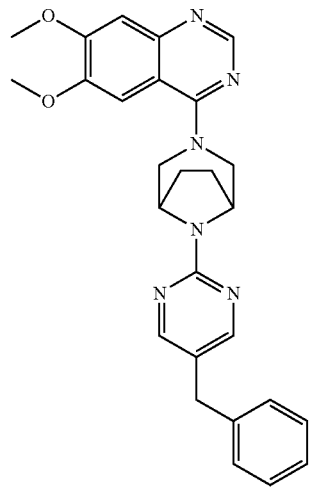 [SMILES: COc1cc2ncnc(N3CC4CCC(C3)N4c3ncc(Cc4ccccc4)cn3)c2cc1OC]

A mixture of (1R,5S)-8-(5-benzylpyrimidin-2-yl)-3,8-diazabicyclo[3.2.1]octane di-HCl salt (31 mg, 0.09 mmol), commercially available 4-chloro-6,7-dimethoxyquinazoline (18 mg, 0.08 mmol) and triethylamine (49 mg, 0.48 mmol) in 2-propanol (0.7 mL) was stirred in a sealed tube at 120° C. for 16 hours. The reaction mixture was then cooled to room temperature. A light-beige solid was isolated by filtration, washed with a small amount of water, and dried to yield 4-((1R,5S)-8-(5-Benzylpyrimidin-2-yl)-3,8-diazabicyclo[3.2.1]octan-3-yl)-6,7-dimethoxyquinazoline (26 mg, 69% yield).

Example 13

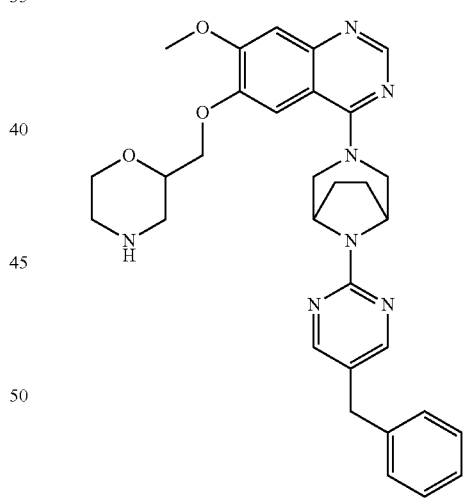

A solution of tert-butyl 2-((((4-((1R,5S)-8-(5-benzylpyrimidin-2-yl)-3,8-diazabicyclo[3.2.1]octan-3-yl)-7-methoxyquinazolin-6-yl)oxy)methyl)morpholine-4-carboxylate (44.2 mg, 0.068 mmol) in trifluoroacetic acid (1 mL) and dichloromethane (2 mL) was stirred 40 hours at room temperature. The excess solvents were evaporated. The residue was dissolved into dichloromethane (3 mL) and washed with aqueous 2N sodium hydroxide (3 mL). The aqueous layer was extracted with fresh dichloromethane (4×3 mL). The combined organic layers were dried over sodium sulfate, filtered, concentrated down, and dried to yield 2-(((4-((1R,5S)-8-(5-Benzylpyrimidin-2-yl)-3,8-diazabicyclo[3.2.1]octan-3-yl)-7-methoxyquinazolin-6-yl)oxy)methyl)morpholine as a cloudy film (33.6 mg, 90% yield).

Example 14

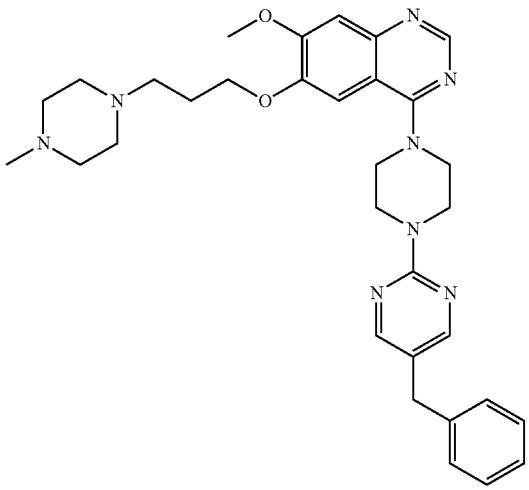 [SMILES: COc1cc2ncnc(N3CCN(c4ncc(Cc5ccccc5)cn4)CC3)c2cc1OCCCN1CCN(C)CC1]

A mixture of 4-(4-(5-benzylpyrimidin-2-yl)piperazin-1-yl)-7-methoxyquinazolin-6-ol (47 mg, 0.11 mmol), 3-(4-methylpiperazin-1-yl)propyl methanesulfonate (35 mg, 0.147 mmol), and cesium carbonate (48 mg, 0.15 mmol) in N,N-dimethylformamide (0.2 mL) was stirred in a sealed tube at 85° C. for 18 hours. The reaction mixture was cooled to room temperature, treated with water (5 mL), sonicated, and stirred. The supernatant was removed, and the sticky residue was dissolved into dichloromethane, dried over sodium sulfate, filtered, and concentrated down. The crude residue was purified by silica gel preparative TLC (elution system was 88:12:1 dichloromethane/methanol/ammonium hydroxide) to yield 4-(4-(5-Benzylpyrimidin-2-yl)piperazin-1-yl)-7-methoxy-6-(3-(4-methylpiperazin-1-yl)propoxy)quinazoline as a beige foamy solid (15.4 mg, 25% yield).

NMR and LC MS data for compounds disclosed herein are shown below.

| Compound Number | 1H NMR | LC MS (M + 1) |
|---|---|---|
| 1 | 1H NMR (400 MHz, DMSO-d6) δ 8.31 (s, 2H), 8.23 (s, 1H), 8.13 (s, 1H), 7.34-7.13 (m, 5H), 4.44-4.10 (m, 4H), 3.90-3.73 (m, 6H). | 372.4 |
| 2 | $^1$H NMR (400 MHz, DMSO-$d_6$) δ 8.31 (s, 1H), 8.30 (s, 1H), 7.40-7.09 (m, 5H), 4.03-3.97 (m, 2H), 3.89 (b.s., 1H), 3.88-3.82 (m, 2H), 3.81-3.72 (m, 6H), 3.72-3.65 (m, 4H). | 373.5 |
| 3 | Reference compound; not encompassed within the current invention. | 382.5 |
| 4 | 1H NMR (400 MHz, DMSO-d6) δ 8.66 (s, 1H), 8.32 (s, 2H), 8.11-7.99 (m, 1H), 7.35-7.12 (m, 7H), 3.92 (broad singlet, 8H), 3.80 (s, 2H). | 412.5 |
| 5 | 1H NMR (400 MHz, DMSO-d6) δ 8.78 (s, 1H), 8.34 (s, 2H), 7.85 (d, J = 9.2 Hz, 1H), 7.67 (dd, J = 9.2, 2.6 Hz, 1H), 7.47 (d, J = 2.7 Hz, 1H), 7.38-7.04 (m, 5H), 4.19 (m, 4H), 4.03-3.86 (m, 7H), 3.81 (s, 2H). | 412.5 |
| 6 | $^1$H NMR (400 MHz, DMSO-$d_6$) δ 8.55 (s, 1H), 8.23 (s, 2H), 7.21 (d, J = 13.1 Hz, 2H), 3.92 (s, 6H), 3.84 (m, 6H), 3.72-3.65 (m, 4H), 1.24-1.14 (m, 1H), 0.59-0.51 (m, 2H), 0.33-0.26 (m, 2H). | 422.5 |
| 7 | 1H NMR (400 MHz, DMSO-d6) δ 8.59 (s, 1H), 8.32 (s, 2H), 7.79 (d, J = 9.1 Hz, 1H), 7.50 (dd, J = 9.1, 2.7 Hz, 1H), 7.34-7.15 (m, 6H), 4.89 (m 1H), 4.48 (m, 1H), 4.26-4.09 (m, 2H), 3.92 (s, 3H), 3.79 (s, 2H), 3.46 (m, 1H), 3.37 (dd, J = 13.1, 3.8 Hz, 1H), 3.26-3.13 (m, 1H), 1.29 (d, J = 6.6 Hz, 3H). | 426.5 |
| 8 | 1H NMR (400 MHz, DMSO-d6) δ 8.57 (s, 1H), 8.29 (s, 2H), 7.97 (d, J = 9.2 Hz, 1H), 7.47-7.29 (m, 5H), 7.20 (d, J = 2.7 Hz, 1H), 7.15 (dd, J = 9.2, 2.7 Hz, 1H), 5.11 (s, 2H), 3.91 (s, 3H), 3.86-3.80 (m, 5H), 3.75 (m, 4H). | 428.5 |
| 9 | $^1$H NMR (400 MHz, Chloroform-d) δ 8.71 (s, 1H), 8.61 (s, 2H), 7.53-7.43 (m, 4H), 7.39-7.29 (m, 2H), 7.18 (s, 1H), 4.15-4.09 (m, 4H), 4.05 (s, 3H), 4.01 (s, 3H), 3.81 (m, 4H). | 428.5 |
| 10 | $^1$H NMR (400 MHz, DMSO-d6) δ 8.59 (s, 1H), 8.29 (s, 2H), 7.78 (d, J = 9.1 Hz, 1H), 7.50 (dd, J = 9.1, 2.8 Hz, 1H), 7.47-7.30 (m, 5H), 7.26 (d, J = 2.8 Hz, 1H), 5.12 (s, 2H), 3.91 (s, 3H), 3.89-3.82 (m, 4H), 3.78-3.71 (m, 4H). | 428.5 |
| 11 | $^1$H NMR (400 MHz, Chloroform-d) δ 8.70 (s, 1H), 8.23 (s, 2H), 7.32-7.27 (m, 3H), 7.23-7.16 (m, 4H), 4.08-3.97 (m, 10H), 3.82 (s, 2H), 3.74 (m, 4H). | 442.5 |
| 12 | 1H NMR (400 MHz, DMSO-d6) δ 8.56 (s, 1H), 8.27 (d, J = 4.9 Hz, 1H), 7.30 (m, 4H), 7.27-7.16 (m, 3H), 6.51 (d, J = 4.9 Hz, 1H), 4.02-3.84 (m, 12H), 3.74-3.63 (m, 4H). | 442.5 |
| 13 | $^1$H NMR (400 MHz, DMSO-$d_6$) δ 8.56 (s, 1H), 8.31 (s, 2H), 7.72 (s, 1H), 7.22 (m, 2H), 7.17-7.11 (m, 2H), 6.81-6.76 (m, 2H), 6.72-6.66 (m, 1H), 3.97-3.89 (m, 10H), 3.75-3.69 (m, 4H). | 443.5 |
| 14 | $^1$H NMR (400 MHz, DMSO-$d_6$) δ 8.57 (s, 1H), 8.35 (s, 2H), 7.38-7.31 (m, 2H), 7.23 (m, 2H), 7.08 (m, 1H), 7.01-6.94 (m, 2H), 4.00-3.89 (m, 10H), 3.79-3.69 (m, 4H). | 444.5 |
| 15 | 1H NMR (400 MHz, DMSO-d6) δ 8.77 (s, 1H), 8.67 (s, 2H), 8.56 (s, 1H), 8.15 (s, 1H), 8.05 (dd, J = 5.3, 1.9 Hz, 1H), 7.52 (ddd, J = 8.7, 7.1, 2.0 Hz, 1H), 7.22 (d, J = 9.0 Hz, 2H), 6.74-6.65 (m, 2H), 4.00-3.83 (m, 10H), 3.71 (t, J = 5.2 Hz, 4H). | 444.5 |
| 16 | 1H NMR (400 MHz, DMSO-d6) δ 8.57 (s, 1H), 8.35 (s, 2H), 8.14 (t, J = 1.8 Hz, 1H), 7.97-7.83 (m, 2H), 7.22 (d, J = 9.0 Hz, 2H), 7.13 (m, 2H), 3.93 (br.s, 10H), 3.79-3.64 (m, 4H). | 444.5 |
| 17 | | 444.5 |

| Compound Number | 1H NMR | LC MS (M + 1) |
|---|---|---|
| 18 | ¹H NMR (400 MHz, DMSO-d₆) δ 8.56 (s, 1H), 8.24 (s, 2H), 7.21 (d, J = 13.0 Hz, 2H), 3.93 (s, 6H), 3.85 (m, 6H), 3.72-3.64 (m, 4H), 2.27 (m, 1H), 1.80-1.69 (m, 2H), 1.55 (m, 4H), 1.37-1.24 (m, 2H). | 450.5 |
| 19 | ¹H NMR (400 MHz, Chloroform-d) δ 8.70 (s, 1H), 8.62 (s, 2H), 7.77-7.72 (m, 2H), 7.63-7.58 (m, 3H), 7.17 (s, 1H), 4.17-4.11 (m, 4H), 4.06 (s, 3H), 4.01 (s, 3H), 3.87 (m, 4H). | 453.5 |
| 20 |  | 455.5 |
| 21 | ¹H NMR (400 MHz, DMSO-d₆) δ 8.73 (s, 2H), 8.57 (s, 1H), 7.38-7.17 (m, 7H), 4.42 (s, 2H), 4.13-4.03 (m, 4H), 3.99 (s, 2H), 3.93 (s, 3H), 3.92 (s, 3H). | 456.5 |
| 22 | ¹H NMR (400 MHz, DMSO-d₆) δ 8.56 (s, 1H), 8.29 (s, 2H), 7.21 (m, 2H), 7.10 (m, 4H), 3.93 (s, 3H), 3.92 (s, 3H), 3.90 (m, 4H), 3.74 (s, 2H), 3.72-3.67 (m, 4H), 2.24 (s, 3H). | 456.5 |
| 23 | 1H NMR (400 MHz, DMSO-d6) δ 8.56 (s, 1H), 8.31 (s, 2H), 7.33-7.14 (m, 7H), 4.88 (m, 1H), 4.49 (m, 1H), 4.19-4.03 (m, 2H), 3.93, (s, 6H), 3.79 (s, 2H), 3.43 (td, J = 13.8, 12.7, 3.3 Hz, 1H), 3.14 (td, J = 12.4, 3.5 Hz, 1H), 1.31 (d, J = 6.6 Hz, 3H). | 456.5 |
| 24 | ¹H NMR (400 MHz, DMSO-d₆) δ 8.55 (s, 1H), 8.22 (s, 2H), 7.32-7.11 (m, 7H), 3.97-3.84 (m, 10H), 3.74-3.63 (m, 4H), 2.87-2.79 (m, 2H), 2.77-2.69 (m, 2H). | 456.5 |
| 25 | ¹H NMR (400 MHz, DMSO-d₆) δ 8.56 (s, 1H), 8.23 (s, 2H), 7.21 (m, 2H), 7.18-7.08 (m, 4H), 3.93 (s, 3H), 3.92 (s, 3H), 3.90 (m, 4H), 3.79 (s, 2H), 3.73-3.67 (m, 4H), 2.24 (s, 3H). | 456.5 |
| 26 | 1H NMR (400 MHz, DMSO-d6) δ 8.56 (s, 1H), 8.31 (s, 2H), 7.34-7.14 (m, 7H), 4.88 (m, 1H), 4.49 (m, 1H), 4.20-4.02 (m, 2H), 3.93 (s, 6H), 3.79 (s, 2H), 3.43 (m, 1H), 3.20-3.08 (m, 1H), 1.31 (d, J = 6.6 Hz, 3H). | 456.5 |
| 27 | ¹H NMR (400 MHz, DMSO-d6) δ 8.54 (s, 1H), 8.29 (s, 2H), 7.35-7.10 (m, 7H), 4.60-4.47 (m, 2H), 4.40-4.31 (m, 1H), 3.92 (m, 7H), 3.78 (s, 2H), 3.60-3.48 (m, 1H), 3.40 (dd, J = 13.2, 3.5 Hz, 1H), 1.22 (d, J = 6.3 Hz, 3H). 1 proton partially buried under water peak. | 456.5 |
| 28 | ¹H NMR (400 MHz, DMSO-d6) δ 8.54 (s, 1H), 8.29 (s, 2H), 7.33-7.11 (m, 7H), 4.59-4.46 (m, 2H), 4.36 (dt, J = 13.1, 1.9 Hz, 1H), 3.92 (d, J = 2.3 Hz, 7H), 3.78 (s, 2H), 3.53 (ddd, J = 13.7, 11.3, 3.3 Hz, 1H), 3.40 (dd, J = 13.1, 3.6 Hz, 1H), 1.22 (d, J = 6.5 Hz, 3H)—1 proton partially buried under water peak. | 456.5 |
| 29 | ¹H NMR (400 MHz, DMSO-d₆) δ 8.54 (s, 1H), 7.65 (s, 1H), 7.32-7.13 (m, 7H), 6.30 (b.s., 2H), 3.92 (s, 3H), 3.91 (s, 3H), 3.86-3.81 (m, 4H), 3.67 3.60 (m, 6H). | 457.5 |
| 30 | 1H NMR (400 MHz, DMSO-d6) δ 8.57 (s, 1H), 8.31 (s, 2H), 7.69 (s, 1H), 7.25 (d, J = 5.4 Hz, 2H), 7.18-7.09 (m, 2H), 6.81-6.73 (m, 2H), 6.69 (m, 1H), 4.88 (m, 1H), 4.54-4.41 (m, 1H), 4.21-4.06 (m, 3H), 3.94 (2 closely spaced singlets, total of 6H), 3.52-3.39 (m, 1H), 3.18 (td, J = 12.2, 3.5 Hz, 1H), 1.34 (d, J = 6.5 Hz, 3H). | 457.5 |
| 31 | ¹H NMR (400 MHz, DMSO-d₆) δ 8.56 (s, 1H), 8.28 (s, 2H), 7.58 (s, 1H), 7.22 (d, J = 10.1 Hz, 2H), 6.97 (d, J = 8.3 Hz, 2H), 6.77-6.68 (m, 2H), 3.93 (s, 6H), 3.90 (m, 4H), 3.74-3.68 (m, 4H), 2.17 (s, 3H). | 457.5 |
| 32 | ¹H NMR (400 MHz, DMSO-d₆) δ 8.56 (s, 1H), 8.26 (s, 2H), 7.22 (d, J = 8.9 Hz, 2H), 7.08 (d, J = 7.6 Hz, 1H), 7.01-6.95 (m, 1H), 6.92 (s, 1H), 6.74-6.65 (m, 2H), 3.92 (m, 10H), 3.72 (m, 4H), 2.21 (s, 3H). | 457.5 |
| 33 | ¹H NMR (400 MHz, DMSO-d₆) δ 8.56 (s, 1H), 8.30 (s, 2H), 7.64 (s, 1H), 7.22 (d, J = 9.1 Hz, 2H), 7.02 (t, J = 7.6 Hz, 1H), 6.58 (d, J = 8.7 Hz, 2H), 6.52 (d, J = 7.4 Hz, 1H), 3.99-3.87 (m, 10H), 3.77-3.67 (m, 4H), 2.19 (s, 3H). | 457.5 |
| 34 | ¹H NMR (400 MHz, DMSO-d6) δ 8.54 (s, 1H), 7.93 (s, 2H), 7.39-7.28 (m, 4H), 7.26-7.15 (m, 3H), 5.86 (t, J = 6.2 Hz, 1H), 4.23 (d, J = 6.3 Hz, 2H), 3.92 (s, 3H), 3.91 (s, 3H), 3.73 (m, 4H), 3.64 (m, 4H). | 457.5 |
| 35 | 1H NMR (400 MHz, DMSO-d6) δ 8.55 (s, 1H), 7.63 (s, 1H), 7.32-7.07 (m, 7H), 3.92 (2 closely spaced singlets, 6H), 3.78 (br.s, 4H), 3.69 (m, 4H), 3.57 (s, 2H). | 458.5 |
| 36 | 1H NMR (400 MHz, DMSO-d₆) δ 8.51 (s, 2H), 7.29 (dd, J = 8.7, 7.2 Hz, 2H), 7.22 (d, J = 8.8 Hz, 2H), 7.05-6.98 (m, 2H), 6.98-6.89 (m, 1H), 4.95 (s, 2H), 3.98 (m, 4H), 3.93 (s, 6H), 3.72 (m, 4H). | 458.5 |
| 37 | ¹H NMR (400 MHz, Chloroform-d) δ 8.69 (s, 1H), 8.17 (s, 2H), 7.45-7.31 (m, 6H), 7.16 (s, 1H), 5.05 (s, 2H), 4.04 (s, 3H), 3.99 (s, 3H), 4.00-3.92 (m, 4H), 3.76 (m, 4H). | 458.5 |
| 38 | ¹H NMR (400 MHz, DMSO-d₆) δ 8.55 (s, 1H), 8.31 (s, 2H), 7.30-7.24 (m, 2H), 7.21 (m, 2H), 7.14-7.07 (m, 2H), 3.91 (m, 10H), 3.79 (s, 2H), 3.74-3.63 (m, 4H). | 460.5 |
| 39 | ¹H NMR (400 MHz, Chloroform-d) δ 8.66 (s, 1H), 8.22 (s, 2H), 7.25-7.15 (m, 4H), 7.00-6.81 (m, 2H), 4.09-3.93 (s, 14H), 3.82 (s, 2H). | 460.5 |
| 40 | ¹H NMR (400 MHz, DMSO-d₆) δ 8.58 (s, 1H), 8.53 (s, 2H), 7.30 (m, 2H), 7.27-7.11 (m, 5H), 4.02 (m, 4H), 3.93 (s, 6H), 3.75 (m, 4H). | 460.5 |
| 41 | 1H NMR (400 MHz, DMSO-d6) δ 8.56 (s, 1H), 8.28 (s, 1H), 7.22 (d, J = 12.1 Hz, 2H), 3.94 (m, 13H), 3.70 (m, 4H). | 461.3 |
| 42 | ¹H NMR (400 MHz, DMSO-d₆) δ 8.56 (s, 1H), 8.29 (s, 2H), 7.69 (s, 1H), 7.22 (d, J = 10.4 Hz, 2H), 7.03-6.94 (m, 2H), 6.84-6.75 (m, 2H), 3.95-3.88 (m, 10H), 3.74-3.68 (m, 4H). | 461.5 |
| 43 | ¹H NMR (400 MHz, DMSO-d₆) δ 8.56 (s, 1H), 8.28 (s, 2H), 7.56 (dd, J = 5.1, 1.3 Hz, 1H), 7.29-7.14 (m, 2H), 7.02 (dd, J = 5.1, 3.4 Hz, 1H), 5.30 (s, 2H), 3.93 (s, 3H), 3.92 (s, 3H), 3.86 (dd, J = 7.2, 3.4 Hz, 4H), 3.68 (dd, J = 6.2, 4.1 Hz, 4H). | 464.5 |

-continued

| Compound Number | 1H NMR | LC MS (M + 1) |
|---|---|---|
| 44 | ¹H NMR (400 MHz, DMSO-d₆) δ 8.57 (s, 1H), 8.27 (s, 2H), 7.56 (m, 1H), 7.30-7.10 (m, 3H), 5.10 (s, 2H), 3.93 (s, 3H), 3.92 (s, 3H), 3.85 (m, 4H), 3.72-3.65 (m, 4H). | 464.5 |
| 45 | ¹H NMR (400 MHz, DMSO-d₆) δ 8.55 (s, 1H), 8.34 (s, 2H), 7.76 (d, J = 7.9 Hz, 2H), 7.45 (d, J = 7.9 Hz, 2H), 7.21 (d, J = 13.1 Hz, 2H), 4.00-3.84 (m, 12H), 3.69 (dd, J = 6.9, 3.5 Hz, 4H). | 467.5 |
| 46 | ¹H NMR (400 MHz, DMSO-d₆) δ 8.55 (s, 1H), 8.35 (s, 2H), 7.75 (t, J = 1.7 Hz, 1H), 7.67 (dt, J = 7.7, 1.4 Hz, 1H), 7.60 (dt, J = 7.9, 1.5 Hz, 1H), 7.50 (t, J = 7.7 Hz, 1H), 7.21 (d, J = 13.2 Hz, 2H), 3.96-3.88 (m, 10H), 3.86 (s, 2H), 3.72-3.65 (m, 4H). | 467.5 |
| 47 | ¹H NMR (400 MHz, DMSO-d₆) δ 8.57 (s, 1H), 8.51 (s, 1H), 8.35 (s, 2H), 7.52 (d, J = 8.8 Hz, 2H), 7.22 (d, J = 9.1 Hz, 2H), 6.79 (d, J = 8.8 Hz, 2H), 4.00-3.89 (m, 10H), 3.76-3.69 (m, 4H). | 468.5 |
| 48 | ¹H NMR (400 MHz, DMSO-d₆) δ 8.45 (s, 1H), 8.34 (s, 2H), 7.34-7.11 (m, 7H), 4.76 (s, 2H), 4.21 (d, J = 12.5 Hz, 2H), 3.90 (s, 3H), 3.88 (s, 3H), 3.80 (s, 2H), 3.48 (d, J = 12.6 Hz, 2H), 3.18-3.00 (m, 2H), 1.16 (t, J = 7.3 Hz, 2H). | 468.6 |
| 49 | 1H NMR (400 MHz, DMSO-d6) δ 8.57 (s, 1H), 8.47 (s, 2H), 7.23 (d, J = 8.2 Hz, 3H), 7.15 (d, J = 7.4 Hz, 1H), 6.99 (t, J = 7.7 Hz, 1H), 6.74-6.59 (m, 2H), 3.94 (m, 10H), 3.84 (t, J = 8.5 Hz, 2H), 3.72 (m, 4H), 3.07 (t, J = 8.3 Hz, 2H). | 469.5 |
| 50 | | 470.6 |
| 51 | 1H NMR (400 MHz, DMSO-d6) δ 10.10 (s, 1H), 8.94 (s, 2H), 8.57 (s, 1H), 7.77-7.67 (m, 2H), 7.34 (t, J = 7.9 Hz, 2H), 7.23 (d, J = 6.6 Hz, 2H), 7.09 (t, J = 7.4 Hz, 1H), 4.18-4.02 (m, 4H), 3.94 (two closely spaced singlets, 3H each), 3.85-3.65 (m, 4H). | 471.5 |
| 52 | ¹H NMR (400 MHz, DMSO-d₆) δ 8.64 (s, 1H), 8.11 (s, 2H), 7.35-7.28 (m, 3H), 7.27-7.19 (m, 4H), 4.42 (s, 2H), 3.93 (s, 3H), 3.92 (s, 3H), 3.79 (dd, J = 6.8, 3.5 Hz, 4H), 3.69-3.64 (m, 4H), 2.88 (s, 3H). | 471.5 |
| 53 | 1H NMR (400 MHz, DMSO-d6) δ 8.55 (s, 1H), 7.91 (s, 2H), 7.38-7.00 (m, 6H), 5.81 (t, J = 6.4 Hz, 1H), 4.18 (d, J = 6.2 Hz, 2H), 3.92 (s, 3H), 3.91 (s, 3H), 3.78 (m, 4H), 3.65 (m, 4H), 2.26 (s, 3H). | 471.5 |
| 54 | 1H NMR (400 MHz, DMSO-d6) δ 8.55 (s, 1H), 7.95 (s, 2H), 7.31-7.10 (m, 6H), 5.67 (t, J = 5.9 Hz, 1H), 4.18 (d, J = 5.7 Hz, 2H), 3.92 (s, 3H), 3.91 (s, 3H), 3.75 (m, 4H), 3.65 (m, 4H), 2.31 (s, 3H). | 471.6 |
| 55 | ¹H NMR (400 MHz, DMSO-d6) δ 8.56 (s, 1H), 7.92 (s, 2H), 7.36-6.95 (m, 6H), 5.82 (t, J = 6.2 Hz, 1H), 4.19 (d, J = 6.2 Hz, 2H), 3.92 (s, 3H), 3.91 (s, 3H), 3.73 (m, 4H), 3.65 (m, 4H), 2.28 (s, 3H). | 471.6 |
| 56 | ¹H NMR (400 MHz, DMSO-d6) δ 8.58 (s, 1H), 7.82 (s, 2H), 7.46-7.05 (m, 7H), 5.82 (d, J = 7.5 Hz, 1H), 4.43 (p, J = 6.8 Hz, 1H), 3.92 (s, 3H), 3.91 (s, 3H), 3.69 (m, 4H), 3.63 (m, 4H), 1.40 (d, J = 6.6 Hz, 3H). | 471.6 |
| 57 | ¹H NMR (400 MHz, DMSO-d₆) δ 8.55 (s, 1H), 8.32 (s, 2H), 7.25-7.16 (m, 3H), 6.84-6.72 (m, 3H), 3.92 (m, 10H), 3.75 (s, 2H), 3.73-3.64 (m, 7H). | 472.5 |
| 58 | ¹H NMR (400 MHz, DMSO-d₆) δ 8.55 (s, 1H), 8.29 (s, 2H), 7.21 (d, J = 12.7 Hz, 2H), 7.16-7.11 (m, 2H), 6.87-6.82 (m, 2H), 3.97-3.87 (m, 10H), 3.72 (s, 2H), 3.69 (m, 7H). | 472.5 |
| 59 | ¹H NMR (400 MHz, DMSO-d₆) δ 8.54 (s, 1H), 8.15 (s, 2H), 7.42-7.32 (m, 4H), 7.29-7.24 (m, 1H), 7.22-7.17 (m, 2H), 5.42 (q, J = 6.3 Hz, 1H), 3.92 (s, 3H), 3.90 (s, 3H), 3.80 (m, 4H), 3.68-3.61 (m, 4H), 1.55 (d, J = 6.3 Hz, 3H). | 472.5 |
| 60 | 1H NMR (400 MHz, DMSO-d6) δ 8.56 (s, 1H), 8.29 (s, 2H), 7.48-7.28 (m, 5H), 7.24 (br.s, 2H), 5.11 (s, 2H), 4.81 (d, J = 6.1 Hz, 1H), 4.39 (dd, J = 13.2, 3.4 Hz, 1H), 4.18-4.04 (m, 2H), 3.93 (s, 6H), 3.47-3.35 (m, 1H), 3.14 (td, J = 12.1, 3.3 Hz, 1H), 1.29 (d, J = 6.6 Hz, 3H). | 472.5 |
| 61 | ¹H NMR (400 MHz, DMSO-d₆) δ 8.55 (s, 1H), 8.28 (s, 2H), 7.33-7.10 (m, 6H), 5.07 (s, 2H), 3.92 (s, 6H), 3.85 (dd, J = 7.0, 3.6 Hz, 4H), 3.75-3.63 (m, 4H), 2.31 (s, 3H). | 472.5 |
| 62 | ¹H NMR (400 MHz, DMSO-d₆) δ 8.56 (s, 1H), 8.27 (s, 2H), 7.35-7.27 (m, 2H), 7.25-7.14 (m, 4H), 5.06 (s, 2H), 3.92 (s, 6H), 3.88-3.80 (m, 4H), 3.73-3.64 (m, 4H), 2.29 (s, 3H). | 472.5 |
| 63 | ¹H NMR (400 MHz, DMSO-d₆) δ 8.54 (s, 1H), 8.15 (s, 2H), 7.42-7.31 (m, 4H), 7.29-7.15 (m, 3H), 5.42 (q, J = 6.4 Hz, 1H), 3.92 (s, 3H), 3.90 (s, 3H), 3.80 (dd, J = 6.6, 3.7 Hz, 4H), 3.69-3.61 (m, 4H), 1.55 (d, J = 6.4 Hz, 3H). | 472.5 |
| 64 | ¹H NMR (400 MHz, DMSO-d₆) δ 8.54 (s, 1H), 8.15 (s, 2H), 7.41-7.38 (m, 2H), 7.34 (m, 2H), 7.30-7.24 (m, 1H), 7.22-7.17 (m, 2H), 5.42 (q, J = 6.4 Hz, 1H), 3.92 (s, 3H), 3.90 (s, 3H), 3.80 (m, 4H), 3.68-3.62 (m, 4H), 1.55 (d, J = 6.4 Hz, 3H). | 472.5 |
| 65 | ¹H NMR (400 MHz, DMSO-d₆) δ 8.56 (s, 1H), 8.31 (s, 2H), 7.40-7.37 (m, 1H), 7.27-7.16 (m, 5H), 5.75 (s, 1H), 5.11 (s, 2H), 3.93 (s, 6H), 3.89-3.83 (m, 4H), 3.74-3.67 (m, 4H), 2.33 (s, 3H). | 472.5 |
| 66 | 1H NMR (400 MHz, DMSO-d6) δ 8.56 (s, 1H), 8.29 (s, 2H), 7.48-7.28 (m, 5H), 7.24 (br.s, 2H), 5.11 (s, 2H), 4.81 (d, J = 7.6 Hz, 1H), 4.39 (d, J = 13.2 Hz, 1H), 4.10 (dd, J = 15.8, 12.8 Hz, 2H), 3.93 (s, 6H), 3.48-3.35 (m, 1H), 3.14 (td, J = 12.2, 3.6 Hz, 1H), 1.29 (d, J = 6.6 Hz, 3H). | 472.5 |
| 67 | 1H NMR (400 MHz, DMSO-d6) δ 8.55 (s, 1H), 8.26 (s, 1H), 7.39 (m, 5H), 7.22 (s, 1H), 7.15 (s, 1H), 5.10 (s, 2H), 4.53 (d, J = 6.7 Hz, 1H), 4.43 (d, J = 12.9 Hz, 1H), 4.33-4.21 (m, 1H), 3.92 (d, J = 2.1 Hz, 7H), 3.54 (t, J = 11.4 Hz, 1H), 3.38 (dd, J = 13.2, 3.6 Hz, 1H), 3.31-3.19 (m, 1H), 1.23 (d, J = 6.6 Hz, 3H). | 472.5 |

-continued

| Compound Number | 1H NMR | LC MS (M + 1) |
|---|---|---|
| 68 | 1H NMR (400 MHz, DMSO-d6) δ 8.55 (s, 1H), 8.26 (s, 2H), 7.48-7.29 (m, 5H), 7.22 (s, 1H), 7.15 (s, 1H), 5.10 (s, 2H), 4.59-4.48 (m, 1H), 4.43 (d, J = 12.8 Hz, 1H), 4.32-4.20 (m, 1H), 3.92 (s, 6H), 3.54 (td, J = 13.3, 12.5, 3.3 Hz, 1H), 3.38 (dd, J = 13.0, 3.6 Hz, 1H), 3.24 (m, 1H), 1.23 (d, J = 6.6 Hz, 3H). | 472.5 |
| 69 | $^1$H NMR (400 MHz, DMSO-$d_6$) δ 8.55 (s, 1H), 8.29 (s, 2H), 7.52-7.46 (m, 2H), 7.26-7.18 (m, 4H), 5.09 (s, 2H), 3.93 (s, 3H), 3.92 (s, 3H), 3.88-3.83 (m, 4H), 3.71-3.66 (m, 4H). | 476.5 |
| 70 | $^1$H NMR (400 MHz, DMSO-$d_6$) δ 8.56 (s, 1H), 8.31 (s, 2H), 7.87 (s, 1H), 7.22 (d, J = 9.3 Hz, 2H), 7.19-7.12 (m, 2H), 6.82-6.71 (m, 2H), 3.93 (s, 10H), 3.76-3.69 (m, 4H). | 478.0 |
| 71 | 1H NMR (400 MHz, DMSO-d6) δ 8.55 (s, 1H), 8.33 (s, 2H), 7.39-7.29 (m, 2H), 7.21 (d, J = 12.9 Hz, 2H), 7.12-7.04 (m, 1H), 3.92 (m, 10H), 3.79 (s, 2H), 3.69 (m, 4H). | 478.5 |
| 72 | | 478.5 |
| 73 | $^1$H NMR (400 MHz, DMSO-$d_6$) δ 8.55 (s, 1H), 8.31 (s, 2H), 7.87 (d, J = 7.9 Hz, 2H), 7.64 (d, J = 8.0 Hz, 2H), 7.21 (d, J = 14.1 Hz, 2H), 5.23 (s, 2H), 3.93 (s, 6H), 3.85 (m, 4H), 3.68 (t, J = 5.0 Hz, 4H). | 483.5 |
| 74 | $^1$H NMR (400 MHz, DMSO-$d_6$) δ 8.57 (s, 1H), 8.36 (s, 2H), 7.23 (d, J = 7.6 Hz, 2H), 6.97 (d, J = 7.3 Hz, 1H), 6.85 (t, J = 7.9 Hz, 1H), 6.58 (dd, J = 7.8, 6.6 Hz, 1H), 6.26 (d, J = 8.2 Hz, 1H), 4.02-3.87 (m, 10H), 3.73 (m, 4H), 3.53-3.46 (m, 2H), 2.79 (t, J = 6.4 Hz, 2H), 2.02-1.92 (m, 2H). | 483.6 |
| 75 | $^1$H NMR (400 MHz, DMSO-$d_6$) δ 8.55 (s, 1H), 8.34 (s, 2H), 7.94 (s, 1H), 7.72 (m, 1H), 7.69 (dt, J = 7.2, 1.7 Hz, 1H), 7.42-7.37 (m, 1H), 7.37-7.30 (m, 3H), 7.21 (d, J = 12.3 Hz, 2H), 3.92 (m, 10H), 3.84 (s, 2H), 3.72-3.65 (m, 4H). | 485.5 |
| 76 | 1H NMR (400 MHz, DMSO-d6) δ 10.11 (s, 1H), 8.58 (s, 2H), 8.55 (s, 1H), 7.32 (m, 4H), 7.28-7.15 (m, 3H), 4.00-3.85 (m, 10H), 3.74-3.65 (m, 4H), 3.62 (s, 2H). | 485.5 |
| 77 | $^1$H NMR (400 MHz, DMSO-$d_6$) δ 8.56 (s, 1H), 8.26 (s, 2H), 7.40-7.32 (m, 2H), 7.21 (d, J = 13.5 Hz, 2H), 6.97-6.89 (m, 2H), 5.03 (s, 2H), 3.92 (s, 6H), 3.85 (dd, J = 6.5, 3.8 Hz, 4H), 3.74 (s, 3H), 3.69 (dd, J = 6.5, 3.6 Hz, 4H). | 488.5 |
| 78 | | 492.6 |
| 79 | $^1$H NMR (400 MHz, DMSO-$d_6$) δ 8.61-8.51 (m, 1H), 8.33-8.29 (m, 2H), 7.37-7.11 (m, 7H), 4.24 (dd, J = 21.6, 6.7 Hz, 2H), 3.97-3.86 (m, 7H), 3.78 (d, J = 10.2 Hz, 2H), 3.75-3.61 (m, 4H), 3.52-3.46 (m, 1H), 3.17-2.98 (m, 4H), 2.90-2.80 (m, 1H). | 497.6 |
| 80 | $^1$H NMR (400 MHz, DMSO-$d_6$) δ 8.55 (s, 1H), 8.32 (s, 2H), 7.39-7.11 (m, 7H), 5.00 (b.s., 1H), 3.96-3.86 (m, 7H), 3.80 (s, 2H), 3.72-3.60 (m, 4H), 3.18-3.10 (m, 1H), 3.03-2.89 (m, 2H), 2.90-2.75 (m, 1H), 2.15-2.02 (m, 1H), 1.94-1.82 (m, 2H). | 497.6 |
| 81 | $^1$H NMR (400 MHz, DMSO-$d_6$) δ 8.55 (s, 1H), 8.31 (s, 2H), 7.29 (d, J = 8.0 Hz, 2H), 7.21 (d, J = 12.6 Hz, 2H), 7.14 (d, J = 8.0 Hz, 2H), 3.92 (m, 10H), 3.75 (s, 2H), 3.68 (dd, J = 6.7, 3.6 Hz, 4H), 1.23 (s, 9H). | 498.6 |
| 82 | $^1$H NMR (400 MHz, DMSO-$d_6$) δ 8.56 (s, 1H), 8.29 (s, 2H), 7.61 (s, 1H), 7.22 (d, J = 9.5 Hz, 2H), 7.20-7.15 (m, 2H), 6.77-6.72 (m, 2H), 3.95-3.87 (m, 10H), 3.74-3.68 (m, 4H), 1.22 (s, 9H). | 499.6 |
| 83 | $^1$H NMR (400 MHz, DMSO-d6) δ 8.54 (s, 1H), 7.92 (s, 2H), 7.20 (m, 2H), 6.92 (s, 1H), 6.84 (m, 2H), 5.96 (s, 2H), 5.79 (t, J = 6.3 Hz, 1H), 4.14 (d, J = 6.3 Hz, 2H), 3.92 (s, 3H), 3.91 (s, 3H), 3.73 (m, 4H), 3.65 (m, 4H). | 501.5 |
| 84 | $^1$H NMR (400 MHz, DMSO-$d_6$) δ 8.54 (s, 1H), 8.31 (s, 2H), 7.35-7.15 (m, 7H), 5.03 (d, J = 5.1 Hz, 1H), 4.72 (t, J = 5.6 Hz, 1H), 4.17 (dd, J = 10.3, 4.0 Hz, 1H), 4.03 (dd, J = 10.3, 6.1 Hz, 1H), 3.93 (s, 3H), 3.91 (dd, J = 6.6, 3.6 Hz, 4H), 3.86 (q, J = 5.2 Hz, 1H), 3.80 (s, 2H), 3.70-3.63 (m, 4H), 3.46 (t, J = 5.8 Hz, 2H). | 502.6 |
| 85 | $^1$H NMR (400 MHz, DMSO-$d_6$) δ 8.54 (s, 1H), 8.32 (s, 2H), 7.37-7.14 (m, 7H), 5.06 (s, 1H), 4.74 (s, 1H), 4.16 (dd, J = 10.2, 4.1 Hz, 1H), 4.03 (dd, J = 10.2, 6.1 Hz, 1H), 3.94-3.92 (m, 7H), 3.90-3.83 (m, 1H), 3.80 (s, 2H), 3.75-3.66 (m, 4H), 3.49-3.44 (m, 2H). | 502.6 |
| 86 | $^1$H NMR (400 MHz, DMSO-d6) δ 8.55 (s, 1H), 8.32 (s, 2H), 7.35-7.06 (m, 6H), 3.92 (m, 10H), 3.79 (s, 2H), 3.68 (m, 4H). | 508.5 |
| 87 | $^1$H NMR (400 MHz, DMSO-$d_6$) δ 8.57 (s, 1H), 8.32 (s, 2H), 7.77 (d, J = 9.1 Hz, 1H), 7.49 (dd, J = 9.1, 2.7 Hz, 1H), 7.34-7.15 (m, 6H), 3.98 (d, J = 5.8 Hz, 2H), 3.94-3.88 (m, 4H), 3.80 (s, 2H), 3.77-3.70 (m, 4H), 2.82-2.75 (m, 2H), 2.15 (s, 3H), 1.94-1.81 (m, 1H), 1.80-1.67 (m, 4H), 1.41-1.28 (m, 2H). | 509.6 |
| 88 | $^1$H NMR (400 MHz, DMSO-$d_6$) δ 8.55 (s, 1H), 8.35 (s, 2H), 7.65 (d, J = 7.9 Hz, 2H), 7.47 (d, J = 7.9 Hz, 2H), 7.21 (d, J = 12.6 Hz, 2H), 3.97-3.87 (m, 12H), 3.69 (dd, J = 6.4, 3.6 Hz, 4H). | 510.5 |
| 89 | $^1$H NMR (400 MHz, DMSO-$d_6$) δ 8.54 (s, 1H), 8.32 (s, 2H), 7.36-7.12 (m, 7H), 4.05-3.95 (m, 2H), 3.93 (s, 3H), 3.92-3.88 (m, 4H), 3.80 (s, 2H), 3.72-3.62 (m, 4H), 2.94-2.78 (m, 2H), 2.75-2.62 (m, 3H), 1.90-1.78 (m, 1H), 1.52-1.37 (m, 1H). | 511.6 |
| 90 | $^1$H NMR (400 MHz, DMSO-$d_6$) δ 8.54 (s, 1H), 8.32 (s, 2H), 7.33-7.15 (m, 7H), 4.26-4.21 (m, 2H), 3.99-3.88 (m, 7H), 3.80 (s, 2H), 3.74-3.63 (m, 4H), 3.39-3.32 (m, 2H), 3.09-3.02 (m, 2H), 2.87-2.78 (m, 1H), 2.25 (s, 3H). | 511.6 |
| 91 | | 511.6 |

-continued

| Compound Number | 1H NMR | LC MS (M + 1) |
|---|---|---|
| 92 | ¹H NMR (400 MHz, DMSO-d₆) δ 8.55 (s, 1H), 8.32 (s, 1H), 7.38-7.10 (m, 7H), 3.96-3.85 (m, 7H), 3.80 (s, 2H), 3.72-3.63 (m, 4H), 3.45-3.35 (m, 2H), 2.78-2.73 (m, 2H), 2.37-2.32 (m, 1H), 2.27 (s, 3H), 1.94-1.82, (m, 2H). | 511.6 |
| 93 | ¹H NMR (400 MHz, DMSO-d₆) δ 8.55 (s, 1H), 8.31 (s, 2H), 7.36-7.12 (m, 7H), 4.52 (d, J = 5.8 Hz, 2H), 4.33 (d, J = 5.8 Hz, 2H), 4.23 (s, 2H), 3.92 (s, 3H), 3.92-3.87 (m, 4H), 3.79 (s, 2H), 3.74-3.62 (m, 4H), 1.39 (s, 3H). | 512.6 |
| 94 | ¹H NMR (400 MHz, DMSO-d₆) δ 8.55 (s, 1H), 8.28 (s, 2H), 7.43-7.33 (m, 4H), 7.21 (d, J = 14.3 Hz, 2H), 5.07 (s, 3H), 3.92 (s, 6H), 3.85 (dd, J = 6.5, 3.7 Hz, 4H), 3.68 (dd, J = 6.3, 3.9 Hz, 4H), 1.27 (s, 9H). | 514.6 |
| 95 | ¹H NMR (400 MHz, DMSO-d₆) δ 8.57 (s, 1H), 7.76 (d, J = 9.1 Hz, 1H), 7.66 (s, 1H), 7.48 (dd, J = 9.1, 2.7 Hz, 1H), 7.33-7.12 (m, 6H), 6.31 (s, 2H), 3.98 (d, J = 5.7 Hz, 2H), 3.87-3.80 (m, 4H), 3.73-3.66 (m, 4H), 3.65 (s, 2H), 2.85-2.75 (m, 2H), 2.16 (s, 3H), 1.95-1.82 (m, 2H), 1.81-1.69 (m, 3H), 1.43-1.27 (m, 2H). | 524.7 |
| 96 |  | 525.6 |
| 97 | ¹H NMR (400 MHz, DMSO-d₆) δ 8.54 (s, 1H), 8.32 (s, 2H), 7.35-7.14 (m, 7H), 3.97 (d, J = 6.6 Hz, 2H), 3.93 (s, 3H), 3.92-3.87 (m, 4H), 3.80 (s, 2H), 3.73-3.64 (m, 4H), 3.16-3.02 (m, 1H), 2.92-2.84 (m, 1H), 2.47-2.34 (m, 1H), 2.07-1.90 (m, 1H), 1.88-1.78 (m, 1H), 1.66-1.56 (m, 1H), 1.47-1.34 (m, 1H), 1.32-1.16 (m, 2H). | 525.6 |
| 98 | ¹H NMR (400 MHz, DMSO-d₆) δ 8.54 (s, 1H), 8.32 (s, 2H), 7.35-7.14 (m, 7H), 3.99-3.85 (m, 7H), 3.80 (s, 2H), 3.72-3.63 (m, 4H), 2.98-2.89 (m, 2H), 1.95-1.80 (m, 3H), 1.74-1.65 (m, 2H), 1.31-1.12 (m, 4H). | 525.6 |
| 99 |  | 525.6 |
| 100 | ¹H NMR (400 MHz, DMSO-d₆) δ 11.35 (b.s., 1H), 8.57 (s, 1H), 7.77 (d, J = 9.1 Hz, 1H), 7.64 (s, 1H), 7.49 (dd, J = 9.1, 2.6 Hz, 1H), 7.30-7.18 (m, 6H), 7.18-7.12 (m, 1H), 3.97 (d, J = 5.7 Hz, 2H), 3.83-3.69 (m, 8H), 3.57 (s, 2H), 2.84-2.75 (m, 2H), 2.16 (s, 3H), 1.97-1.82 (m, 2H), 1.82-1.68 (m, 3H), 1.43-1.26 (m, 2H). | 525.6 |
| 101 | ¹H NMR (400 MHz, DMSO-d₆) δ 8.55 (s, 1H), 8.35 (s, 2H), 7.43 (t, J = 8.1 Hz, 1H), 7.28 (m, 2H), 7.24-7.17 (m, 3H), 3.96-3.89 (m, 10H), 3.86 (s, 2H), 3.73-3.65 (m, 4H). | 526.5 |
| 102 | ¹H NMR (400 MHz, DMSO-d₆) δ 8.55 (s, 1H), 8.31 (s, 2H), 7.76 (d, J = 8.0 Hz, 2H), 7.66 (d, J = 8.0 Hz, 2H), 7.21 (d, J = 13.8 Hz, 2H), 5.24 (s, 2H), 3.92 (s, 6H), 3.86 (dd, J = 6.4, 3.8 Hz, 4H), 3.72-3.66 (m, 4H). | 526.5 |
| 103 | ¹H NMR (400 MHz, Chloroform-d) δ 8.69 (s, 1H), 8.15 (s, 2H), 7.34-7.25 (m, 4H), 7.16 (s, 1H), 4.99 (s, 2H), 4.04 (s, 3H), 3.98 (m, 7H), 3.79 (m, 4H). | 527.4 |
| 104 | ¹H NMR (400 MHz, DMSO-d₆) δ 8.54 (s, 1H), 8.31 (s, 2H), 7.35-7.14 (m, 7H), 4.13-4.04 (m, 2H), 3.93 (s, 3H), 3.92-3.87 (m, 4H), 3.79 (s, 2H), 3.78-3.72 (m, 2H), 3.71-3.63 (m, 4H), 3.56-3.42 (m, 1H), 2.92-2.85 (m, 1H), 2.75-2.61 (m, 2H), 2.60-2.51 (m, 1H). | 527.6 |
| 105 | ¹H NMR (400 MHz, DMSO-d₆) δ 8.54 (s, 1H), 8.32 (s, 2H), 7.35-7.14 (m, 7H), 4.13-4.04 (m, 2H), 3.93 (s, 3H), 3.93-3.87 (m, 4H), 3.80 (s, 2H), 3.78-3.72 (m, 2H), 3.72-3.62 (m, 4H), 3.52-3.44 (m, 1H), 2.92-2.85 (m, 1H), 2.74-2.63 (m, 2H), 2.60-2.51 (m, 1H). | 527.6 |
| 106 | ¹H NMR (400 MHz, DMSO-d₆) δ 8.54 (s, 1H), 8.31 (s, 2H), 7.33-7.13 (m, 7H), 4.19-4.04 (m, 2H), 3.93 (s, 3H), 3.92-3.87 (m, 4H), 3.79 (s, 2H), 3.78-3.74 (m, 2H), 3.71-3.62 (m, 4H), 3.56-3.45 (m, 1H), 2.96-2.88 (m, 1H), 2.78-2.64 (m, 2H), 2.63-2.54 (m, 1H). | 527.6 |
| 107 | 1H NMR (400 MHz, DMSO-d6) δ 8.55 (s, 1H), 8.50 (s, 2H), 7.20 (d, J = 6.3 Hz, 2H), 4.18 (t, J = 6.4 Hz, 2H), 3.93 (d, J = 3.4 Hz, 7H), 3.77-3.65 (m, 4H), 2.54 (t, J = 7.1 Hz, 2H), 2.46-2.40 (m, 4H), 2.01-1.89 (m, 2H), 1.73-1.63 (m, 4H). | 528.4 |
| 108 |  | 530.6 |
| 109 |  | 539.6 |
| 110 | 1H NMR (400 MHz, DMSO-d6) δ 8.50 (s, 1H), 8.32 (s, 2H), 7.35-7.15 (m, 7H), 4.24 (t, J = 5.6 Hz, 2H), 3.93 (s, 3H), 3.92-3.86 (m, 4H), 3.80 (s, 2H), 3.71-3.66 (m, 2H), 3.63-3.55 (m, 4H), 3.51 (t, J = 7.0 Hz, 2H), 2.21 (t, J = 8.1 Hz, 2H), 1.96-1.88 (m, 2H). | 539.6 |
| 111 | ¹H NMR (400 MHz, DMSO-d₆) δ 8.54 (s, 1H), 8.31 (s, 2H), 7.33-7.15 (m, 7H), 4.25 (t, J = 5.6 Hz, 2H), 3.92 (m, 7H), 3.80 (s, 2H), 3.73-3.65 (m, 4H), 3.61 (t, J = 5.5 Hz, 2H), 3.51 (t, J = 7.0 Hz, 2H), 2.21 (t, J = 8.1 Hz, 2H), 1.92 (p, J = 7.6 Hz, 2H). | 539.6 |
| 112 | ¹H NMR (400 MHz, DMSO-d₆) δ 8.54 (s, 1H), 8.31 (s, 2H), 7.33-7.15 (m, 7H), 3.97 (d, J = 5.9 Hz, 2H), 3.93 (s, 3H), 3.92-3.86 (m, 4H), 3.79 (s, 2H), 3.71-3.62 (m, 4H), 2.81 (d, J = 10.9 Hz, 2H), 2.18 (s, 3H), 1.99-1.85 (m, 2H), 1.82-1.68 (m, 3H), 1.43-1.28 (m, 2H). | 539.7 |
| 113 | ¹H NMR (400 MHz, DMSO-d₆) δ 8.54 (s, 1H), 8.31 (s, 2H), 7.34-7.14 (m, 7H), 3.99 (d, J = 6.5 Hz, 2H), 3.93 (s, 3H), 3.92-3.87 (m, 4H), 3.79 (s, 2H), 3.71-3.62 (m, 4H), 2.87-2.78 (m, 1H), 2.68-2.58 (m, 1H), 2.15 (s, 3H), 2.12-1.99 (m, 1H), 1.98-1.70 (m, 3H), 1.71-1.59 (m, 1H), 1.56-1.42 (m, 1H), 1.19-0.99 (m, 1H). | 539.7 |
| 114 |  | 539.7 |
| 115 | ¹H NMR (400 MHz, DMSO-d₆) δ 8.55 (s, 1H), 8.32 (s, 2H), 7.35-7.15 (m, 7H), 4.00 (d, J = 6.4 Hz, 2H), 3.94 (s, 3H), 3.93-3.88 (m, 4H), 3.80 (s, 2H), | 539.7 |

-continued

| Compound Number | 1H NMR | LC MS (M + 1) |
|---|---|---|
| | 3.71-3.65 (m, 4H), 2.89-2.78 (m, 1H), 2.68-2.58 (m, 1H), 2.16 (s, 3H), 2.13-1.98 (m, 1H), 1.96-1.72 (m, 3H), 1.71-1.42 (m, 2H), 1.18-1.00 (m, 1H). | |
| 116 | $^1$H NMR (400 MHz, DMSO-d$_6$) δ 8.54 (s, 1H), 8.32 (s, 2H), 7.34-7.15 (m, 7H), 4.22 (t, J = 5.9 Hz, 2H), 3.92 (s, 3H), 3.92-3.88 (m, 4H), 3.80 (s, 2H), 3.73-3.64 (m, 4H), 2.74-2.64 (m, 6H), 2.45-2.37 (m, 4H). | 540.7 |
| 117 | | 541.6 |
| 118 | | 541.6 |
| 119 | $^1$H NMR (400 MHz, DMSO-d$_6$) δ 8.53 (s, 1H), 7.63 (b.s., 1H), 7.29-7.10 (m, 7H), 4.18-4.05 (m, 2H), 3.93 (s, 3H), 3.84-3.73 (m, 6H), 3.70-3.63 (m, 4H), 3.62-3.45 (m, 3H), 3.01-2.90 (m, 1H), 2.86-2.53 (m, 3H). | 543.6 |
| 120 | $^1$H NMR (400 MHz, DMSO-d$_6$) δ 8.54 (s, 1H), 7.62 (b.s., 1H), 7.30-7.10 (m, 7H), 4.15-4.04 (m, 2H), 3.93 (s, 3H), 3.84-3.74 (m, 6H), 3.70-3.63 (m, 4H), 3.56 (s, 2H), 3.50 (td, J = 11.1, 3.0 Hz, 1H), 2.97-2.90 (m, 1H), 2.80-2.64 (m, 2H), 2.59 (dd, J = 12.3, 10.3 Hz, 1H). | 543.6 |
| 121 | | 553.7 |
| 123 | 1H NMR (400 MHz, DMSO-d6) δ 8.73 (s, 2H), 8.56 (s, 1H), 7.54 (d, J = 7.9 Hz, 1H), 7.47 (s, 1H), 7.44 (d, J = 7.8 Hz, 1H), 7.33 (t, J = 7.6 Hz, 1H), 7.26 (d, J = 7.9 Hz, 1H), 7.22 (s, 2H), 7.15 (d, J = 7.6 Hz, 1H), 4.17 (t, J = 6.5 Hz, 2H), 4.01 (m, 4H), 3.94 (s, 3H), 3.74 (t, J = 5.1 Hz, 4H), 2.43-2.28 (m, 8H), 1.93 (m, 2H), 1.49 (m, 4H), 1.37 (m, 2H). | 553.7 |
| 124 | | 554.7 |
| 125 | $^1$H NMR (400 MHz, DMSO-d$_6$) δ 8.53 (s, 1H), 7.65 (s, 1H), 7.32-7.12 (m, 7H), 6.30 (s, 2H), 3.97 (d, J = 5.8 Hz, 2H), 3.93 (s, 3H), 3.86-3.79 (m, 4H), 3.65 (s, 2H), 3.65-3.58 (m, 4H), 2.84-2.73 (m, 2H), 2.16 (s, 3H), 1.93-1.82 (m, 2H), 1.80-1.70 (m, 3H), 1.42-1.28 (m, 2H). | 554.7 |
| 126 | $^1$H NMR (400 MHz, DMSO-d$_6$) δ 8.54 (s, 1H), 8.32 (s, 2H), 7.37-7.14 (m, 7H), 4.23 (d, J = 6.0 Hz, 3H), 3.95-3.88 (m, 7H), 3.80 (s, 2H), 3.72-3.65 (m, 4H), 2.81-2.73 (m, 2H), 2.65-2.10 (m, 11H, buried under DMSO peak). | 554.7 |
| 127 | $^1$H NMR (400 MHz, DMSO-d$_6$) δ 8.54 (s, 1H), 7.64 (s, 1H), 7.30-7.11 (m, 7H), 3.97 (d, J = 5.9 Hz, 2H), 3.93 (s, 2H), 3.81-3.73 (m, 4H), 3.72-3.64 (m, 4H), 3.57 (s, 2H), 2.91-2.75 (m, 2H), 2.20 (s, 3H), 2.02-1.87 (m, 1H), 1.82-1.70 (m, 4H), 1.43-1.27 (m, 2H). | 555.7 |
| 128 | | 555.7 |
| 129 | | 555.7 |
| 130 | | 557.6 |
| 131 | | 557.7 |
| 132 | $^1$H NMR (400 MHz, DMSO-d$_6$) δ 8.55 (s, 1H), 8.29 (s, 2H), 7.68 (s, 1H), 7.23 (s, 1H), 7.19 (s, 1H), 6.99 (t, J = 8.8 Hz, 2H), 6.87-6.73 (m, 2H), 3.99 (d, J = 5.9 Hz, 2H), 3.93 (s, 2H), 3.92-3.87 (m, 4H), 3.74-3.67 (m, 4H), 2.84-2.75 (m, 2H), 2.16 (s, 3H), 1.95-1.83 (s, 1H), 1.82-1.71 (m, 4H), 1.45-1.28 (m, 2H). | 558.6 |
| 133 | $^1$H NMR (400 MHz, DMSO-d$_6$) δ 8.55 (s, 1H), 8.35 (s, 2H), 7.25-7.15 (m, 4H), 7.07-7.00 (m, 3H), 4.01-3.96 (m, 2H), 3.96-3.91 (m, 7H), 3.76-3.68 (m, 4H), 2.85-2.74 (m, 2H), 2.16 (s, 3H), 1.93-1.82 (m, 2H), 1.81-1.71 (m, 3H), 1.42-1.28 (m, 2H). | 559.6 |
| 134 | $^1$H NMR (400 MHz, DMSO-d$_6$) δ 8.54 (s, 1H), 8.31 (s, 2H), 7.29 (m, 2H), 7.25-7.15 (m, 5H), 4.16 (t, J = 6.4 Hz, 2H), 3.91 (m, 7H), 3.80 (s, 2H), 3.72-3.64 (m, 4H), 2.42 (t, J = 7.1 Hz, 2H), 2.39-2.22 (m, 8H), 2.13 (s, 3H), 1.92 (t, J = 6.8 Hz, 2H). | 568.7 |
| 135 | $^1$H NMR (400 MHz, DMSO-d$_6$) δ 8.52 (s, 1H), 7.65 (s, 1H), 7.34-7.10 (m, 7H), 6.30 (s, 2H), 4.20 (q, J = 7.0 Hz, 2H), 3.97 (d, J = 5.9 Hz, 2H), 3.86-3.79 (m, 4H), 3.65 (s, 2H), 3.64-3.59 (m, 4H), 2.85-2.75 (m, 2H), 2.16 (s, 3H), 1.94-1.81 (m, 2H), 1.80-1.79 (m, 3H), 1.39 (t, J = 7.0 Hz, 3H), 1.39-1.29 (m, 2H). | 568.7 |
| 136 | $^1$H NMR (400 MHz, DMSO-d$_6$) δ 8.54 (s, 1H), 8.32 (s, 2H), 7.37-7.12 (m, 7H), 4.14 (t, J = 6.4 Hz, 2H), 3.95-3.87 (m, 7H), 3.80 (s, 2H), 3.71-3.63 (m, 4H), 2.43 (t, J = 7.2 Hz, 2H), 2.43-2.15 (m, 8H), 2.10 (s, 3H), 1.97-1.85 (m, 2H). | 568.7 |
| 137 | 1H NMR (400 MHz, DMSO-d6) δ 8.55 (s, 1H), 8.28 (s, 2H), 7.59 (s, 2H), 7.21 (d, J = 4.2 Hz, 2H), 6.97 (d, J = 8.1 Hz, 2H), 6.77-6.68 (m, 2H), 4.17 (t, J = 6.4 Hz, 2H), 3.93 (s, 3H), 3.92-3.85 (m, 4H), 3.71 (t, J = 5.2 Hz, 4H), 2.39 (t, J = 7.1 Hz, 2H), 2.33 (br.s, 4H), 2.17 (s, 3H), 1.93 (m, 2H), 1.49 (m, 4H), 1.37 (m, 2H). | 568.7 |
| 138 | $^1$H NMR (400 MHz, DMSO-d$_6$) δ 11.36 (b.s., 1H), 8.53 (s, 1H), 7.64 (s, 1H), 7.30-7.10 (m, 7H), 4.20 (q, J = 7.0 Hz, 2H), 3.96 (d, J = 5.9 Hz, 2H), 3.84-3.61 (m, 8H), 3.57 (s, 2H), 2.84-2.73 (m, 2H), 2.16 (s, 3H), 1.93-1.82 (m, 2H), 1.80-1.69 (m, 3H), 1.39 (t, J = 6.9 Hz, 3H), 1.40-1.27 (m, 2H). | 569.7 |
| 139 | $^1$H NMR (400 MHz, DMSO-d$_6$) δ 8.54 (s, 1H), 8.32 (s, 2H), 7.35-7.12 (m, 7H), 4.05-3.95 (m, 6H), 3.93 (s, 3H), 3.92-3.87 (m, 4H), 3.80 (s, 2H), 3.71-3.64 (m, 4H), 3.56-3.46 (m, 2H), 3.05-2.89 (m, 2H), 2.05-1.90 (m, 2H), 1.87-1.67 (m, 3H), 1.55-1.28 (m, 2H). | 569.7 |
| 140 | $^1$H NMR (400 MHz, DMSO-d$_6$) δ 8.55 (s, 1H), 8.53 (s, 1H), 7.30-7.13 (m, 6H), 4.03-3.95 (m, 6H), 3.93 (s, 3H), 3.78-3.69 (m, 4H), 2.84-2.75 (m, 2H), 2.16 (s, 3H), 1.94-1.83 (m, 2H), 1.80-1.70 (m, 3H), 1.45-1.28 (m, 2H). | 575.7 |

Biochemical Activity of Compounds

In order to assess the activity of chemical compounds against the relevant kinase of interest, the Caliper Life-Sciences electrophoretic mobility shift technology platform is used. Fluorescently labeled substrate peptide is incubated in the presence of kinase and ATP so that a reflective proportion of the peptide is phosphorylated. At the end of the reaction, the mix of phosphorylated (product) and non-phosphorylated (substrate) peptides are passed through the microfluidic system of the Caliper EZ Reader 2, under an applied potential difference. The presence of the phosphate group on the product peptide provides a difference in mass and charge between those of the substrate peptide, resulting in a separation of the substrate and product pools in the sample. As the pools pass a LEDS within the instrument, these pools are detected and resolved as separate peaks. The ratio between these peaks therefore reflects the activity of the chemical matter at that concentration in that well, under those conditions.

Kit wild type assay at Km: In each well of a 384-well plate, 0.2 ng/ul final (2 nM) of wild type Kit (Carna Bioscience 08-156) was incubated in a total of 12.5 ul of buffer (100 mM HEPES pH 7.5, 0.015% Brij 35, 10 mM MgCl2, 1 mM DTT) with 1 uM Srctide (5-FAM-GEEPLY-WSFPAKKK-NH2)(SEQ ID NO: 1)) and 400 uM ATP at 25 C for 90 minutes in the presence or absence of a dosed concentration series of compound (1% DMSO final concentration). The reaction was stopped by the addition of 70 ul of Stop buffer (100 mM HEPES pH 7.5, 0.015% Brij 35, 35 mM EDTA and 0.2% of Coating Reagent 3 (Caliper Life-sciences)). The plate was then read on a Caliper EZReader 2 (protocol settings: −1.9 psi, upstream voltage −700, downstream voltage −3000, post sample sip 35s). Data was normalized to 0% and 100% inhibition controls and the IC50 or EC50 calculated using a 4-parameter fit using GraphPad Prism.

Kit D816V assay at Km: In each well of a 384-well plate, 0.04 ng/ul (0.5 nM) of D816V Kit (Carna Bioscience 08-156) was incubated in a total of 12.5 ul of buffer (100 mM HEPES pH 7.5, 0.015% Brij 35, 10 mM MgCl2, 1 mM DTT) with 1 uM Srctide (5-FAM-GEEPLYWSF-PAKKK-NH2) (SEQ ID NO: 1)) and 15 uM ATP at 25 C for 90 minutes in the presence or absence of a dosed concentration series of compound (1% DMSO final concentration). The reaction was stopped by the addition of 70 ul of Stop buffer (100 mM HEPES pH 7.5, 0.015% Brij 35, 35 mM EDTA and 0.2% of Coating Reagent 3 (Caliper Life-sciences)). The plate was then read on a Caliper EZReader 2 (protocol settings: −1.9 psi, upstream voltage −700, downstream voltage −3000, post sample sip 35s). Data was normalized to 0% and 100% inhibition controls and the IC50 or EC50 calculated using a 4-parameter fit using GraphPad Prism.

The Table below shows the activity of compounds described herein, against wild-type Kit and mutant Kit (the D816V mutant). In the Table below, for D816V activity, the following designations are used: <1.00 nM=A; 1.01-10.0 nM=B; 10.01-100.0 nM=C; and >100 nM=D. For wild-type Kit activity, the following designations are used: <10 nM=A; 11-100 nM=B; 100-1000 nM=C; >1000 nM=D.

| Compound Id | Structure | INH-KITD816V ENZ-KM IC50 (nM) (Num) | INH-KITWT ENZ-KM IC50 (nM) (Num) |
|---|---|---|---|
| 1 | 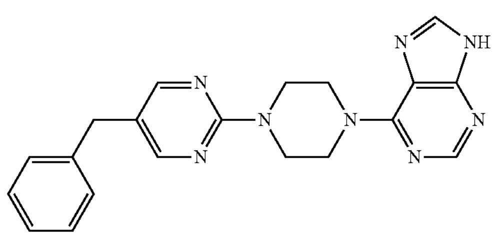 [SMILES: c1ccc(Cc2cnc(N3CCN(c4ncnc5[nH]cnc45)CC3)nc2)cc1] | C | D |
| 2 | 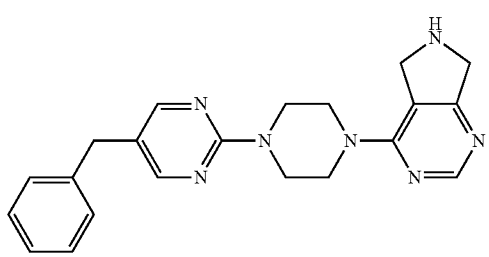 [SMILES: c1ccc(Cc2cnc(N3CCN(c4ncnc5c4CNC5)CC3)nc2)cc1] | D | D |

-continued
| Compound Id | Structure | INH-KITD816V ENZ-KM IC50 (nM) (Num) | INH-KITWT ENZ-KM IC50 (nM) (Num) |
|---|---|---|---|
| 3 | 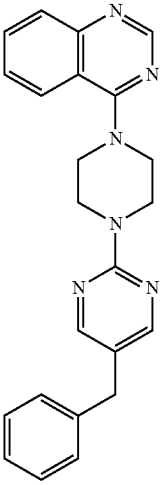 [SMILES: c1ccc(Cc2cnc(N3CCN(c4ncnc5ccccc45)CC3)nc2)cc1] | D | D |
| 4 | 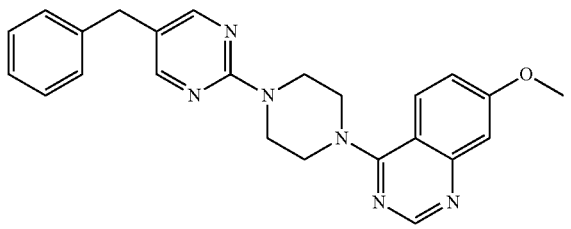 [SMILES: COc1ccc2c(N3CCN(c4ncc(Cc5ccccc5)cn4)CC3)ncnc2c1] | B | C |
| 5 | 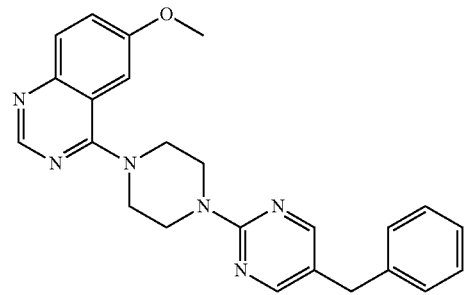 [SMILES: COc1ccc2ncnc(N3CCN(c4ncc(Cc5ccccc5)cn4)CC3)c2c1] | C | C |
| 6 | 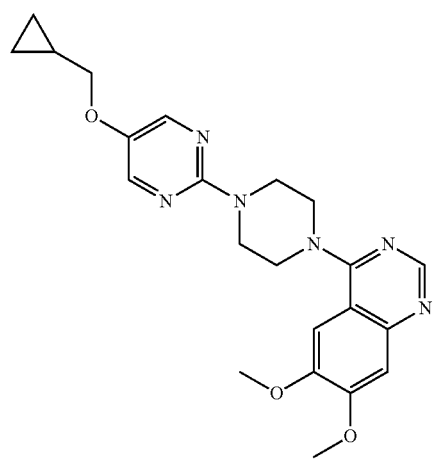 [SMILES: COc1cc2ncnc(N3CCN(c4ncc(OCC5CC5)cn4)CC3)c2cc1OC] | D | D |

-continued

| Compound Id | Structure | INH-KITD816V ENZ-KM IC50 (nM) (Num) | INH-KITWT ENZ-KM IC50 (nM) (Num) |
|---|---|---|---|
| 7 | Chiral | C | C |
| 8 | 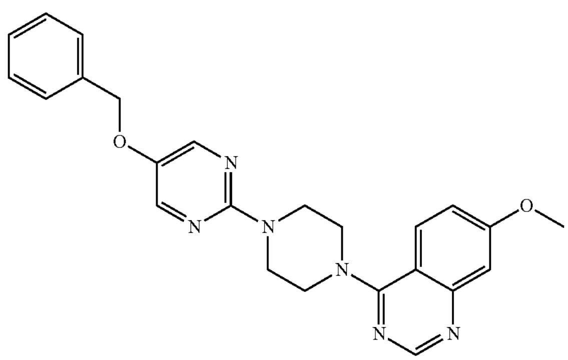 [SMILES: COc1ccc2c(N3CCN(c4ncc(OCc5ccccc5)cn4)CC3)ncnc2c1] | D | D |
| 9 | 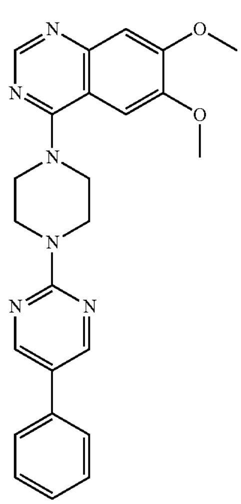 [SMILES: COc1cc2ncnc(N3CCN(c4ncc(-c5ccccc5)cn4)CC3)c2cc1OC] | D | D |

-continued

| Compound Id | Structure | INH-KITD816V ENZ-KM IC50 (nM) (Num) | INH-KITWT ENZ-KM IC50 (nM) (Num) |
|---|---|---|---|
| 10 | 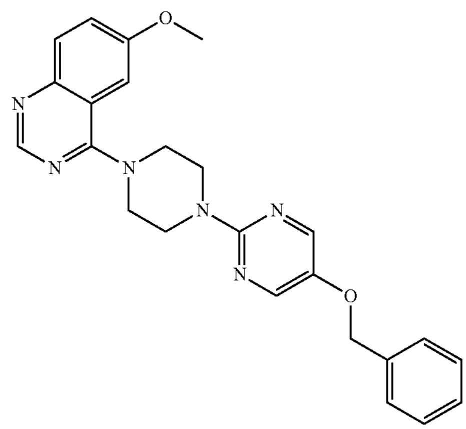 [SMILES: COc1ccc2ncnc(N3CCN(c4ncc(OCc5ccccc5)cn4)CC3)c2c1] | D | D |
| 11 | 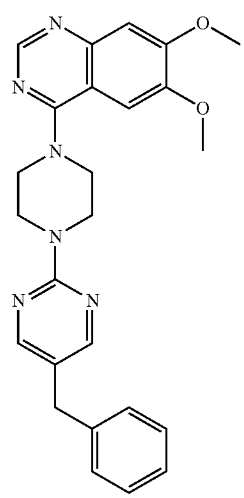 [SMILES: COc1cc2ncnc(N3CCN(c4ncc(Cc5ccccc5)cn4)CC3)c2cc1OC] | B | B |
| 12 | 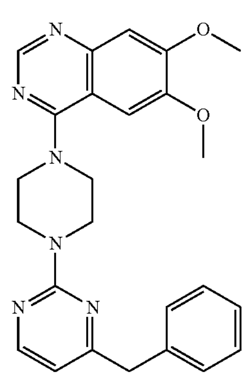 [SMILES: COc1cc2ncnc(N3CCN(c4nccc(Cc5ccccc5)n4)CC3)c2cc1OC] | D | D |

-continued

| Compound Id | Structure | INH-KITD816V ENZ-KM IC50 (nM) (Num) | INH-KITWT ENZ-KM IC50 (nM) (Num) |
|---|---|---|---|
| 13 | 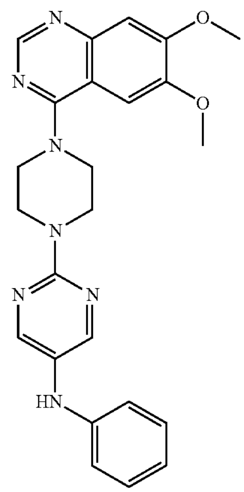 [SMILES: COc1cc2ncnc(N3CCN(c4ncc(Nc5ccccc5)cn4)CC3)c2cc1OC] | B | C |
| 14 | 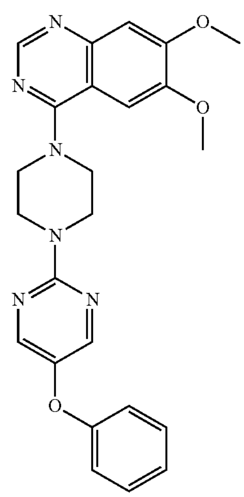 [SMILES: COc1cc2ncnc(N3CCN(c4ncc(Oc5ccccc5)cn4)CC3)c2cc1OC] | B | B |
| 15 | 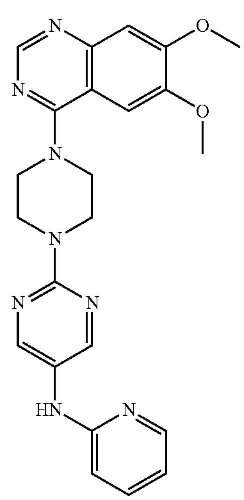 [SMILES: COc1cc2ncnc(N3CCN(c4ncc(Nc5ccccn5)cn4)CC3)c2cc1OC] | C | C |

-continued
| Compound Id | Structure | INH-KITD816V ENZ-KM IC50 (nM) (Num) | INH-KITWT ENZ-KM IC50 (nM) (Num) |
|---|---|---|---|
| 16 | 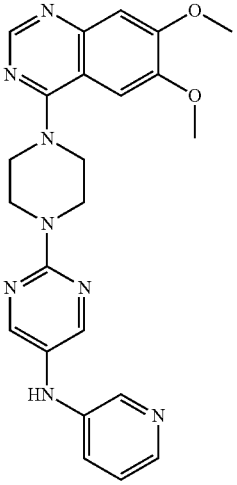 [SMILES: COc1cc2ncnc(N3CCN(c4ncc(Nc5cccnc5)cn4)CC3)c2cc1OC] | C | C |
| 17 | 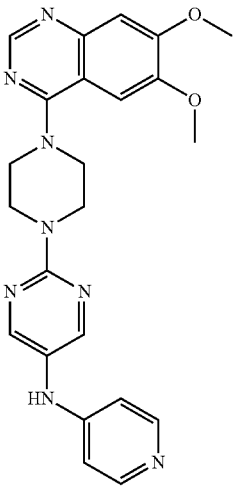 [SMILES: COc1cc2ncnc(N3CCN(c4ncc(Nc5ccncc5)cn4)CC3)c2cc1OC] | D | D |
| 18 | 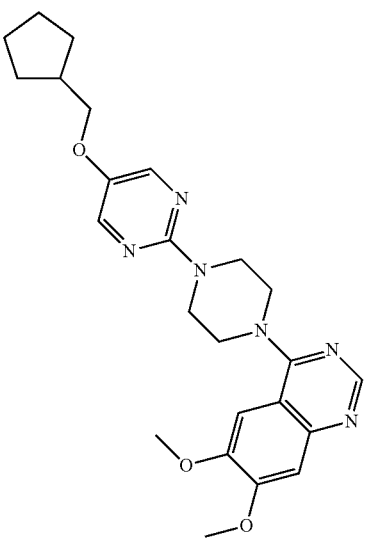 [SMILES: COc1cc2ncnc(N3CCN(c4ncc(OCC5CCCC5)cn4)CC3)c2cc1OC] | D | D |

-continued

| Compound Id | Structure | INH-KITD816V ENZ-KM IC50 (nM) (Num) | INH-KITWT ENZ-KM IC50 (nM) (Num) |
| --- | --- | --- | --- |
| 19 | 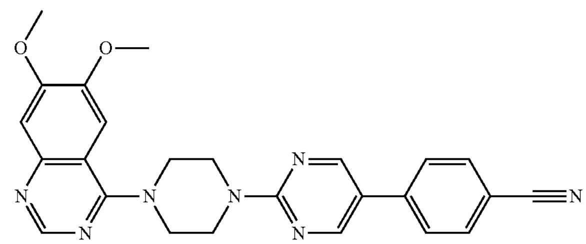 [SMILES: COc1cc2ncnc(N3CCN(c4ncc(-c5ccc(C#N)cc5)cn4)CC3)c2cc1OC] | D | D |
| 20 | 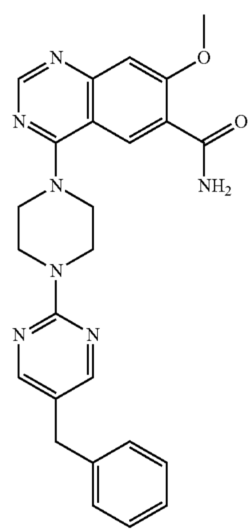 [SMILES: COc1cc2ncnc(N3CCN(c4ncc(Cc5ccccc5)cn4)CC3)c2cc1C(N)=O] | C | D |
| 21 | 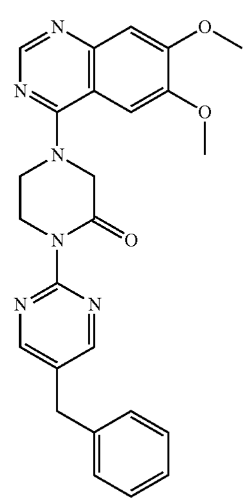 [SMILES: COc1cc2ncnc(N3CCN(c4ncc(Cc5ccccc5)cn4)C(=O)C3)c2cc1OC] | D | D |

-continued
| Compound Id | Structure | INH-KITD816V ENZ-KM IC50 (nM) (Num) | INH-KITWT ENZ-KM IC50 (nM) (Num) |
|---|---|---|---|
| 22 | 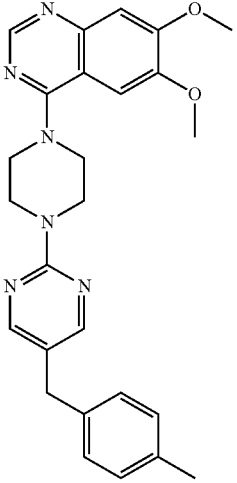 [SMILES: COc1cc2ncnc(N3CCN(c4ncc(Cc5ccc(C)cc5)cn4)CC3)c2cc1OC] | B | B |
| 23 | 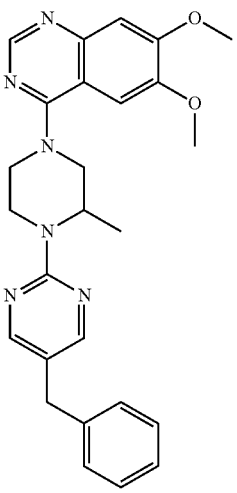 [SMILES: COc1cc2ncnc(N3CCN(c4ncc(Cc5ccccc5)cn4)C(C)C3)c2cc1OC] | B | B |
| 24 | 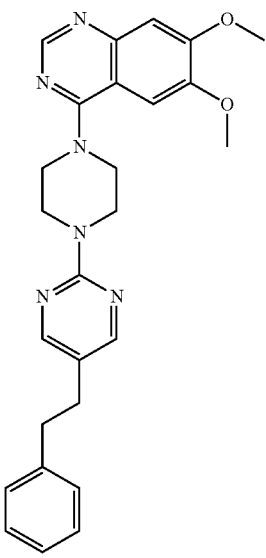 [SMILES: COc1cc2ncnc(N3CCN(c4ncc(CCc5ccccc5)cn4)CC3)c2cc1OC] | B | C |

-continued
| Compound Id | Structure | INH-KITD816V ENZ-KM IC50 (nM) (Num) | INH-KITWT ENZ-KM IC50 (nM) (Num) |
|---|---|---|---|
| 25 | 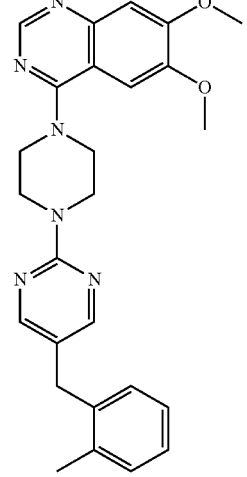 | C | C |
| 26 | 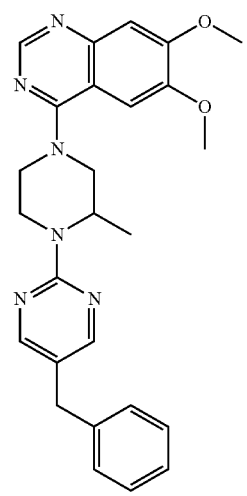 [SMILES: COc1cc2ncnc(N3CCN(c4ncc(Cc5ccccc5)cn4)C(C)C3)c2cc1OC] | C | C |
| 27 | 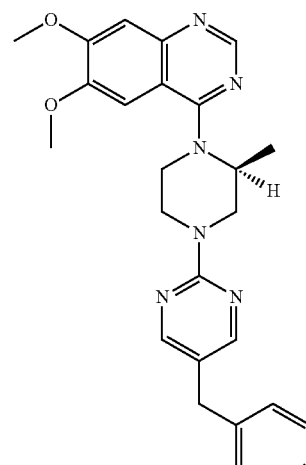 Chiral | D | D |

-continued
| Compound Id | Structure | INH-KITD816V ENZ-KM IC50 (nM) (Num) | INH-KITWT ENZ-KM IC50 (nM) (Num) |
|---|---|---|---|
| 28 | 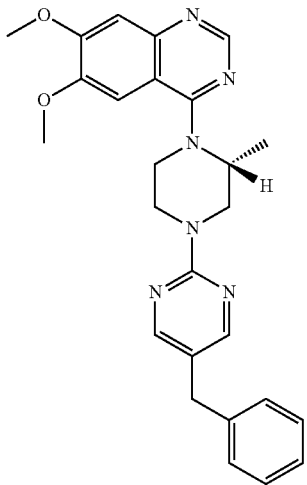 Chiral | D | D |
| 29 | 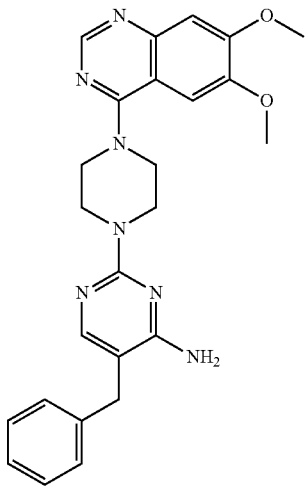 | A | A |
| 30 | 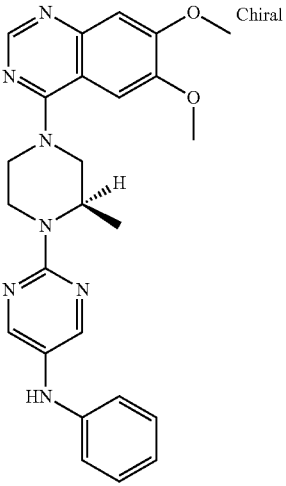 [SMILES: COc1cc2ncnc(N3CCN(c4ncc(Nc5ccccc5)cn4)[C@H](C)C3)c2cc1OC] Chiral | B | C |

-continued
| Compound Id | Structure | INH-KITD816V ENZ-KM IC50 (nM) (Num) | INH-KITWT ENZ-KM IC50 (nM) (Num) |
|---|---|---|---|
| 31 | 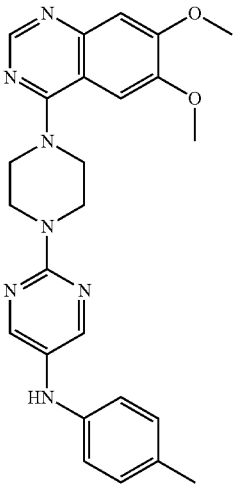 [SMILES: COc1cc2ncnc(N3CCN(c4ncc(Nc5ccc(C)cc5)cn4)CC3)c2cc1OC] | B | C |
| 32 | 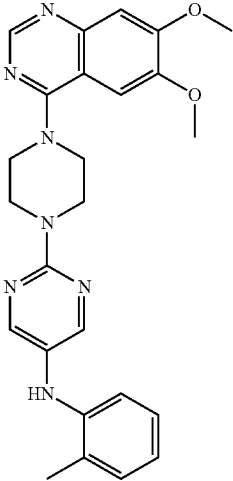 [SMILES: COc1cc2ncnc(N3CCN(c4ncc(Nc5ccccc5C)cn4)CC3)c2cc1OC] | C | C |
| 33 | 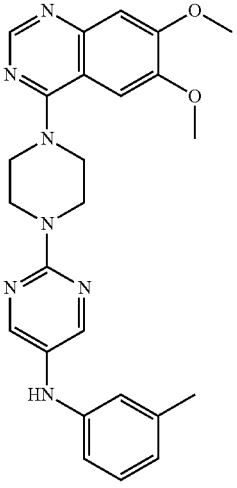 [SMILES: COc1cc2ncnc(N3CCN(c4ncc(Nc5cccc(C)c5)cn4)CC3)c2cc1OC] | C | C |

-continued
| Compound Id | Structure | INH-KITD816V ENZ-KM IC50 (nM) (Num) | INH-KITWT ENZ-KM IC50 (nM) (Num) |
|---|---|---|---|
| 34 | 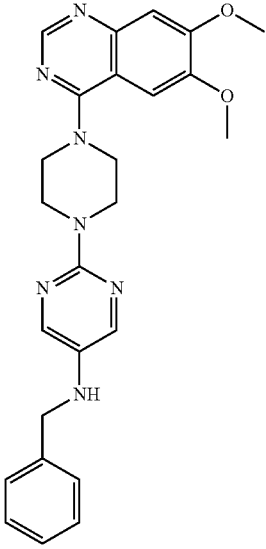 [SMILES: COc1cc2ncnc(N3CCN(c4ncc(NCc5ccccc5)cn4)CC3)c2cc1OC] | C | C |
| 35 | 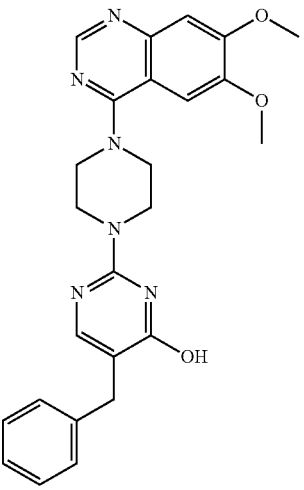 [SMILES: COc1cc2ncnc(N3CCN(c4ncc(Cc5ccccc5)c(O)n4)CC3)c2cc1OC] | A | A |

-continued

| Compound Id | Structure | INH-KITD816V ENZ-KM IC50 (nM) (Num) | INH-KITWT ENZ-KM IC50 (nM) (Num) |
| --- | --- | --- | --- |
| 36 | 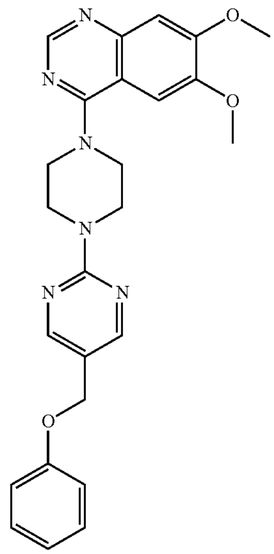 [SMILES: COc1cc2ncnc(N3CCN(c4ncc(COc5ccccc5)cn4)CC3)c2cc1OC] | B | B |
| 37 | 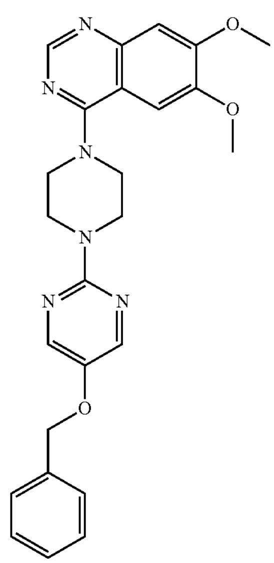 [SMILES: COc1cc2ncnc(N3CCN(c4ncc(OCc5ccccc5)cn4)CC3)c2cc1OC] | B | C |

-continued
| Compound Id | Structure | INH-KITD816V ENZ-KM IC50 (nM) (Num) | INH-KITWT ENZ-KM IC50 (nM) (Num) |
|---|---|---|---|
| 38 | 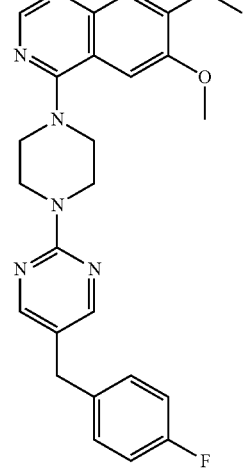 | B | B |
| 39 | 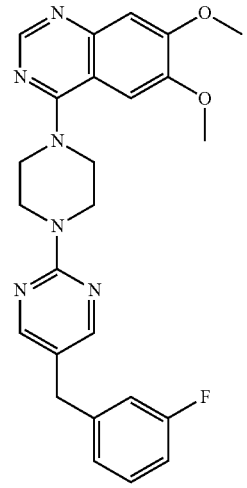 [SMILES: COc1cc2ncnc(N3CCN(c4ncc(Cc5cccc(F)c5)cn4)CC3)c2cc1OC] | B | C |
| 40 | 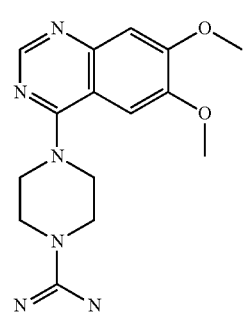 | B | C |

-continued

| Compound Id | Structure | INH-KITD816V ENZ-KM IC50 (nM) (Num) | INH-KITWT ENZ-KM IC50 (nM) (Num) |
| --- | --- | --- | --- |
| 41 | 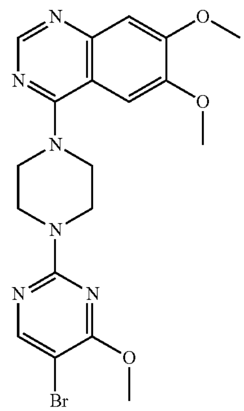 [SMILES: COc1cc2ncnc(N3CCN(c4ncc(Br)c(OC)n4)CC3)c2cc1OC] | D | D |
| 42 | 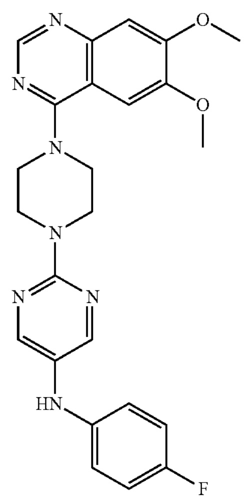 [SMILES: COc1cc2ncnc(N3CCN(c4ncc(Nc5ccc(F)cc5)cn4)CC3)c2cc1OC] | B | C |
| 43 | 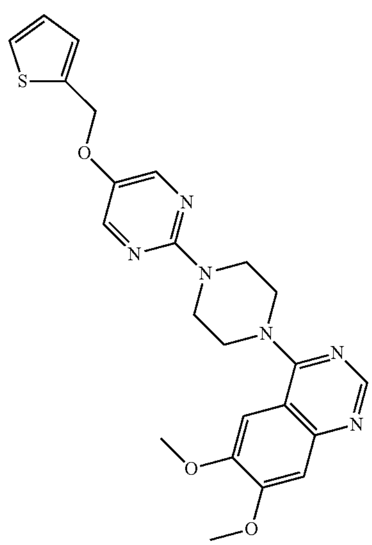 [SMILES: COc1cc2ncnc(N3CCN(c4ncc(OCc5cccs5)cn4)CC3)c2cc1OC] | B | C |

-continued
| Compound Id | Structure | INH-KITD816V ENZ-KM IC50 (nM) (Num) | INH-KITWT ENZ-KM IC50 (nM) (Num) |
|---|---|---|---|
| 44 | 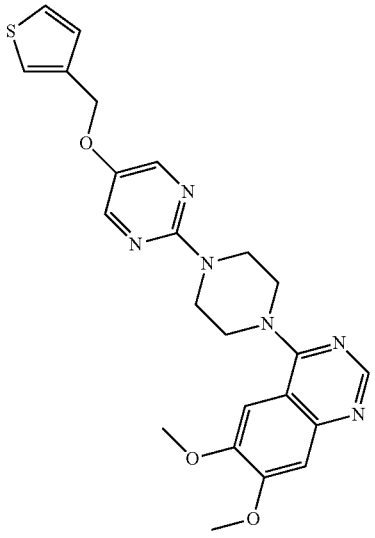 [SMILES: COc1cc2ncnc(N3CCN(c4ncc(OCc5ccsc5)cn4)CC3)c2cc1OC] | C | C |
| 45 | 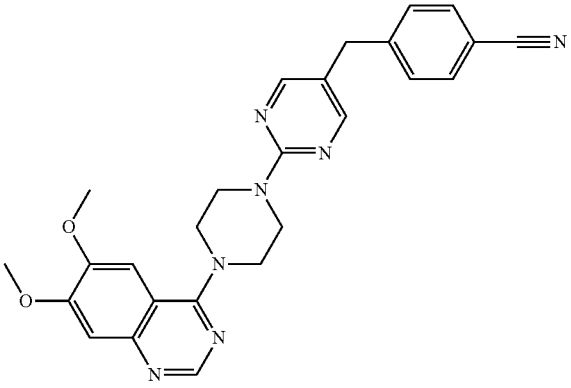 | B | C |
| 46 | 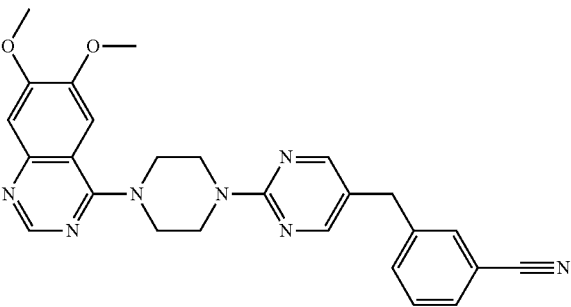 [SMILES: COc1cc2ncnc(N3CCN(c4ncc(Cc5cccc(C#N)c5)cn4)CC3)c2cc1OC] | C | C |

-continued
| Compound Id | Structure | INH-KITD816V ENZ-KM IC50 (nM) (Num) | INH-KITWT ENZ-KM IC50 (nM) (Num) |
|---|---|---|---|
| 47 | 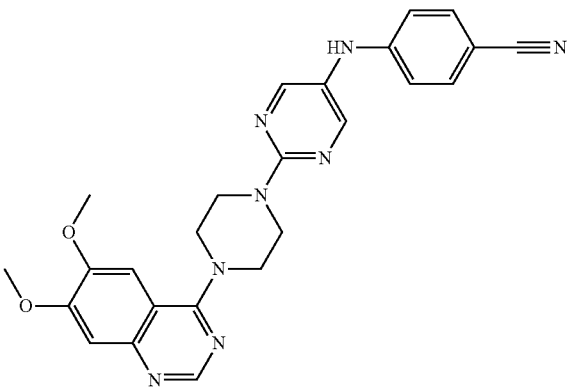 [SMILES: COc1cc2ncnc(N3CCN(c4ncc(Nc5ccc(C#N)cc5)cn4)CC3)c2cc1OC] | C | D |
| 48 | 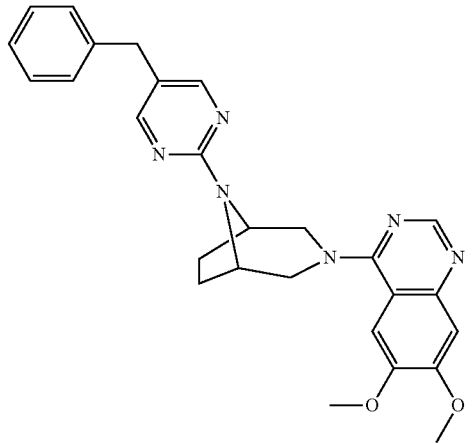 [SMILES: COc1cc2ncnc(N3CC4CCC(C3)N4c3ncc(Cc4ccccc4)cn3)c2cc1OC] | B | B |
| 49 | 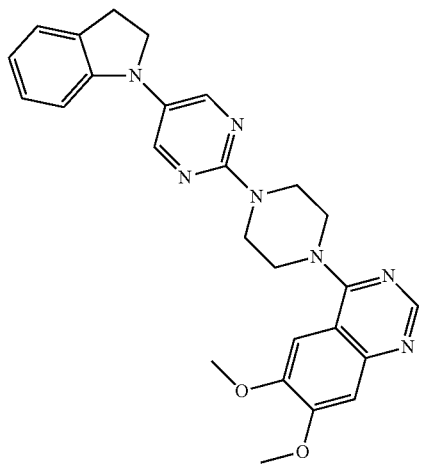 [SMILES: COc1cc2ncnc(N3CCN(c4ncc(N5CCc6ccccc65)cn4)CC3)c2cc1OC] | C | C |

| Compound Id | Structure | INH-KITD816V ENZ-KM IC50 (nM) (Num) | INH-KITWT ENZ-KM IC50 (nM) (Num) |
|---|---|---|---|
| 50 | 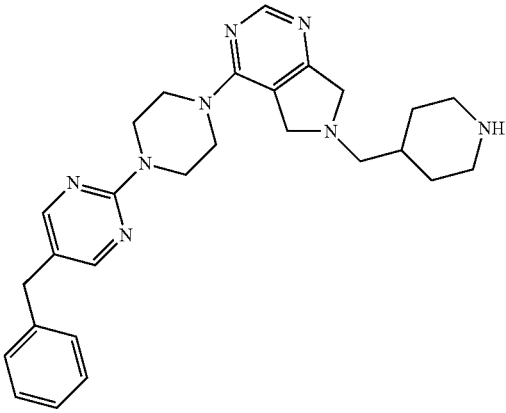 [SMILES: c1ccc(Cc2cnc(N3CCN(c4ncnc5c4CN(CC4CCNCC4)C5)CC3)nc2)cc1] | D | D |
| 51 | 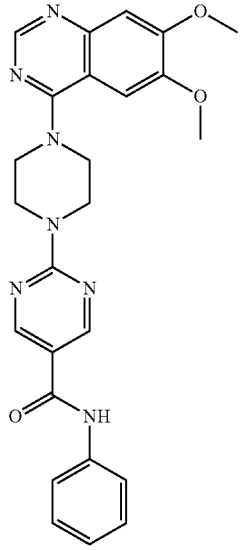 [SMILES: COc1cc2ncnc(N3CCN(c4ncc(C(=O)Nc5ccccc5)cn4)CC3)c2cc1OC] | C | D |
| 52 | 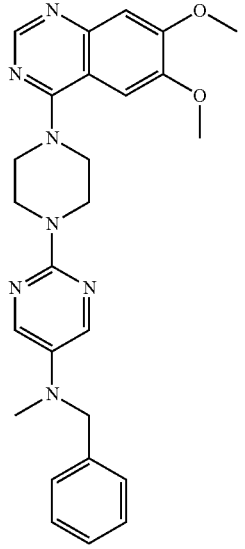 [SMILES: COc1cc2ncnc(N3CCN(c4ncc(N(C)Cc5ccccc5)cn4)CC3)c2cc1OC] | B | B |

| Compound Id | Structure | INH-KITD816V ENZ-KM IC50 (nM) (Num) | INH-KITWT ENZ-KM IC50 (nM) (Num) |
| --- | --- | --- | --- |
| 53 | 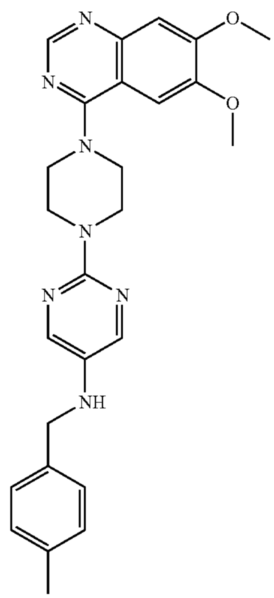 [SMILES: COc1cc2ncnc(N3CCN(c4ncc(NCc5ccc(C)cc5)cn4)CC3)c2cc1OC] | C | C |
| 54 | 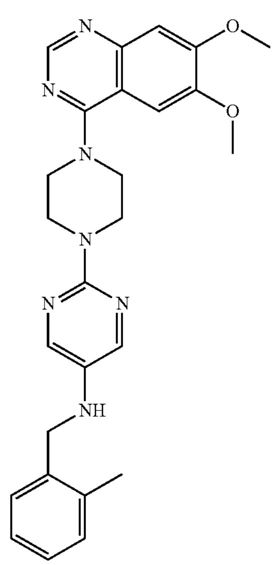 [SMILES: COc1cc2ncnc(N3CCN(c4ncc(NCc5ccccc5C)cn4)CC3)c2cc1OC] | C | C |

-continued

| Compound Id | Structure | INH-KITD816V ENZ-KM IC50 (nM) (Num) | INH-KITWT ENZ-KM IC50 (nM) (Num) |
|---|---|---|---|
| 55 | 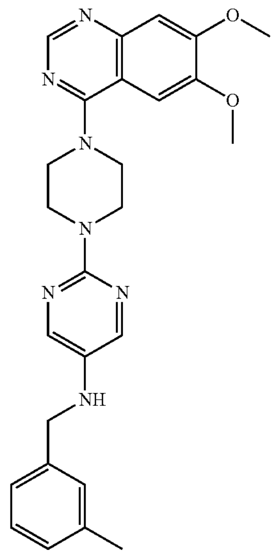 [SMILES: COc1cc2ncnc(N3CCN(c4ncc(NCc5cccc(C)c5)cn4)CC3)c2cc1OC] | C | D |
| 56 | 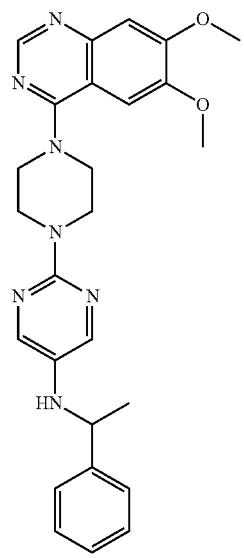 [SMILES: COc1cc2ncnc(N3CCN(c4ncc(NC(C)c5ccccc5)cn4)CC3)c2cc1OC] | C | D |
| 57 | 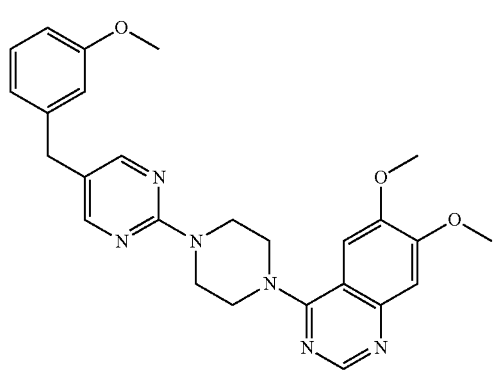 [SMILES: COc1cccc(Cc2cnc(N3CCN(c4ncnc5cc(OC)c(OC)cc45)CC3)nc2)c1] | A | B |

-continued
| Compound Id | Structure | INH-KITD816V ENZ-KM IC50 (nM) (Num) | INH-KITWT ENZ-KM IC50 (nM) (Num) |
|---|---|---|---|
| 58 | 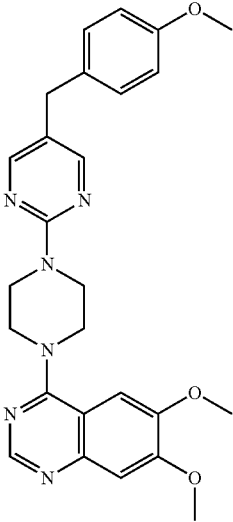 [SMILES: COc1ccc(Cc2cnc(N3CCN(c4ncnc5cc(OC)c(OC)cc45)CC3)nc2)cc1] | B | B |
| 59 | 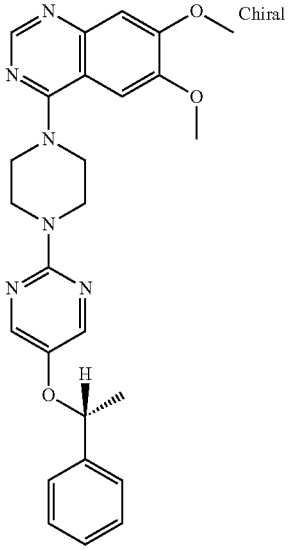 [SMILES: COc1cc2ncnc(N3CCN(c4ncc(O[C@H](C)c5ccccc5)cn4)CC3)c2cc1OC] | B | C |

-continued
| Compound Id | Structure | INH-KITD816V ENZ-KM IC50 (nM) (Num) | INH-KITWT ENZ-KM IC50 (nM) (Num) |
|---|---|---|---|
| 60 | 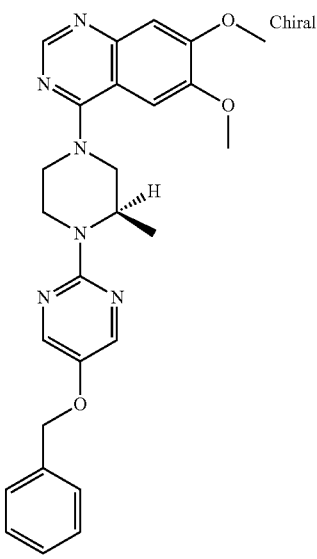 [SMILES: COc1cc2ncnc(N3CCN(c4ncc(OCc5ccccc5)cn4)[C@H](C)C3)c2cc1OC] | C | C |
| 61 | 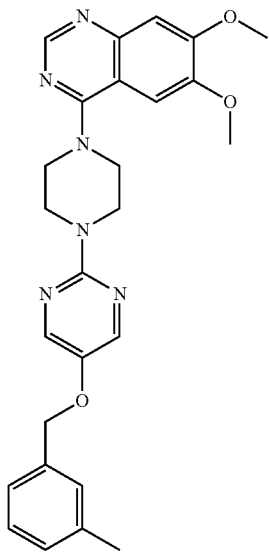 [SMILES: COc1cc2ncnc(N3CCN(c4ncc(OCc5cccc(C)c5)cn4)CC3)c2cc1OC] | C | C |

-continued
| Compound Id | Structure | INH-KITD816V ENZ-KM IC50 (nM) (Num) | INH-KITWT ENZ-KM IC50 (nM) (Num) |
|---|---|---|---|
| 62 | 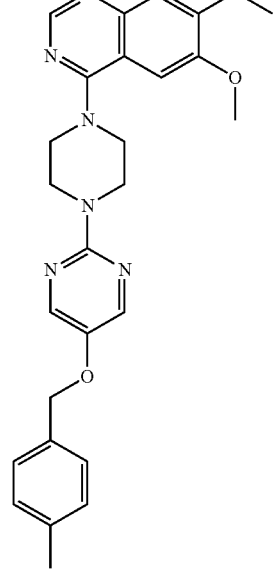 | C | D |
| 63 | 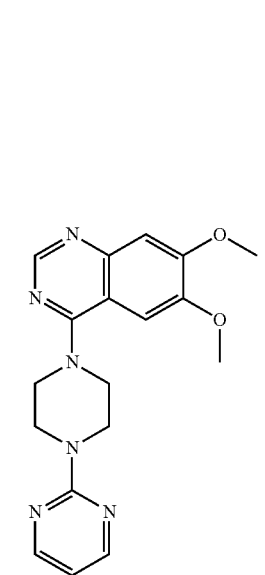 | C | C |

-continued
| Compound Id | Structure | INH-KITD816V ENZ-KM IC50 (nM) (Num) | INH-KITWT ENZ-KM IC50 (nM) (Num) |
|---|---|---|---|
| 64 | 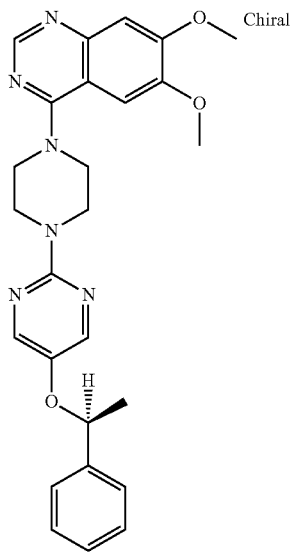 [SMILES: COc1cc2ncnc(N3CCN(c4ncc(O[C@@H](C)c5ccccc5)cn4)CC3)c2cc1OC] | C | D |
| 65 | 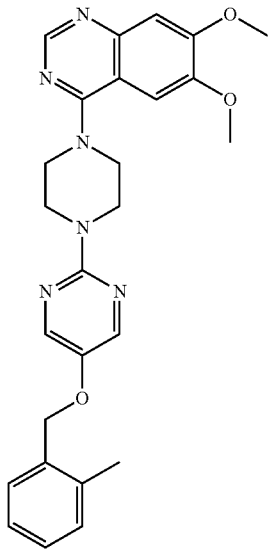 [SMILES: COc1cc2ncnc(N3CCN(c4ncc(OCc5ccccc5C)cn4)CC3)c2cc1OC] | C | D |

| Compound Id | Structure | INH-KITD816V ENZ-KM IC50 (nM) (Num) | INH-KITWT ENZ-KM IC50 (nM) (Num) |
| --- | --- | --- | --- |
| 66 | 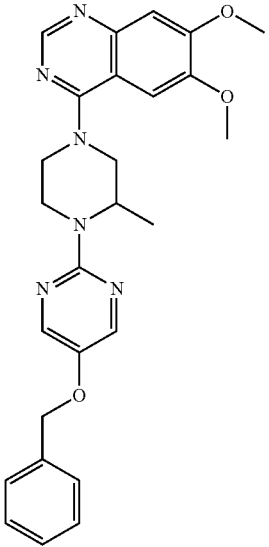 [SMILES: COc1cc2ncnc(N3CCN(c4ncc(OCc5ccccc5)cn4)C(C)C3)c2cc1OC] | C | D |
| 67 | 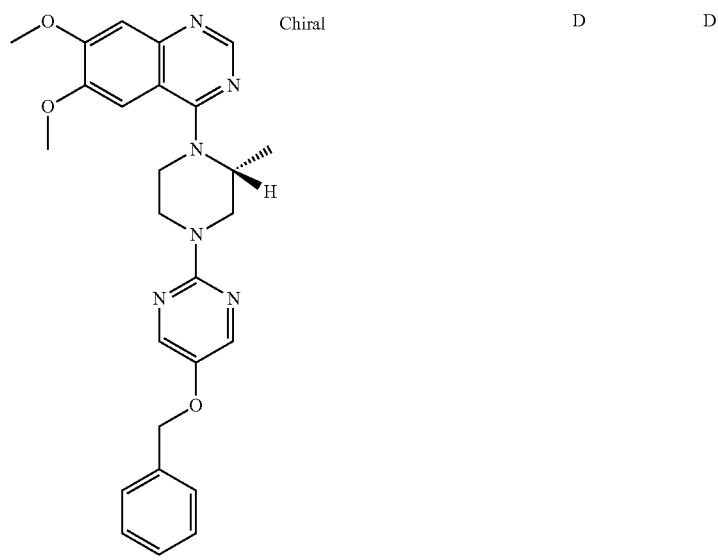 Chiral | D | D |

| Compound Id | Structure | INH-KITD816V ENZ-KM IC50 (nM) (Num) | INH-KITWT ENZ-KM IC50 (nM) (Num) |
|---|---|---|---|
| 68 | 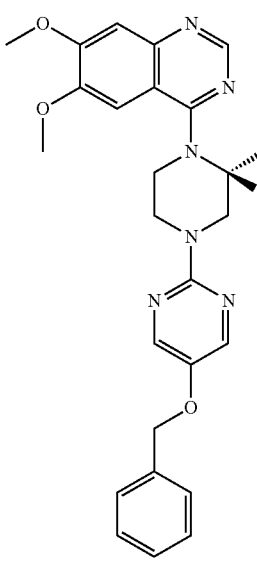 Chiral | D | D |
| 69 | 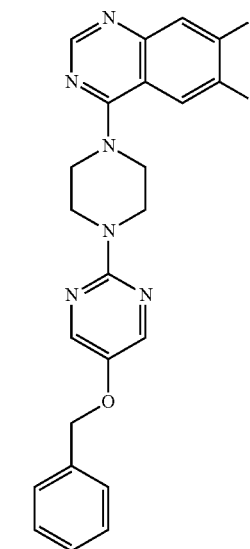 | C | C |

| Compound Id | Structure | INH-KITD816V ENZ-KM IC50 (nM) (Num) | INH-KITWT ENZ-KM IC50 (nM) (Num) |
|---|---|---|---|
| 70 | 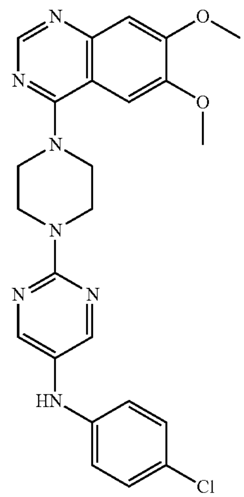 [SMILES: COc1cc2ncnc(N3CCN(c4ncc(Nc5ccc(Cl)cc5)cn4)CC3)c2cc1OC] | B | C |
| 71 | 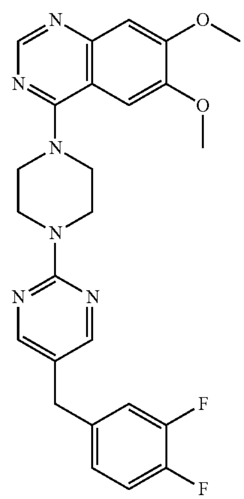 [SMILES: COc1cc2ncnc(N3CCN(c4ncc(Cc5ccc(F)c(F)c5)cn4)CC3)c2cc1OC] | B | C |
| 72 | 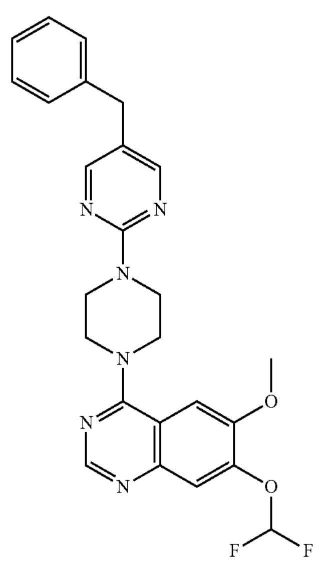 [SMILES: COc1cc2c(N3CCN(c4ncc(Cc5ccccc5)cn4)CC3)ncnc2cc1OC(F)F] | C | |

-continued

| Compound Id | Structure | INH-KITD816V ENZ-KM IC50 (nM) (Num) | INH-KITWT ENZ-KM IC50 (nM) (Num) |
|---|---|---|---|
| 73 | 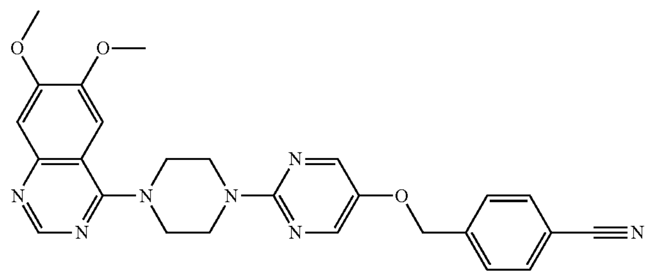 [SMILES: COc1cc2ncnc(N3CCN(c4ncc(OCc5ccc(C#N)cc5)cn4)CC3)c2cc1OC] | D | D |
| 74 | 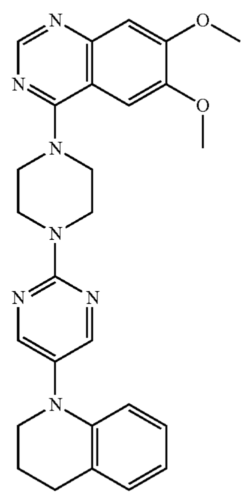 [SMILES: COc1cc2ncnc(N3CCN(c4ncc(N5CCCc6ccccc65)cn4)CC3)c2cc1OC] | C | C |
| 75 | 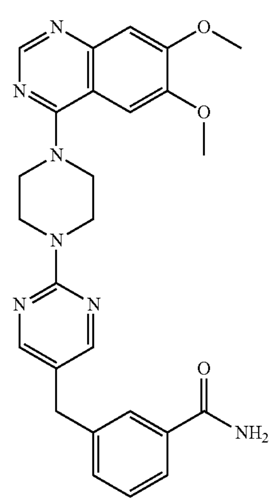 [SMILES: COc1cc2ncnc(N3CCN(c4ncc(Cc5cccc(C(N)=O)c5)cn4)CC3)c2cc1OC] | B | C |

-continued

| Compound Id | Structure | INH-KITD816V ENZ-KM IC50 (nM) (Num) | INH-KITWT ENZ-KM IC50 (nM) (Num) |
|---|---|---|---|
| 76 | 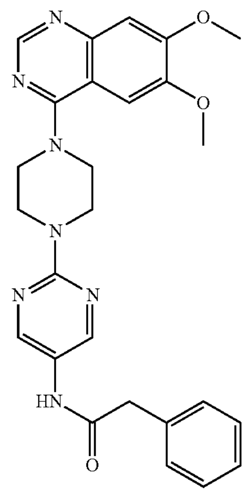 [SMILES: COc1cc2ncnc(N3CCN(c4ncc(NC(=O)Cc5ccccc5)cn4)CC3)c2cc1OC] | C | C |
| 77 | 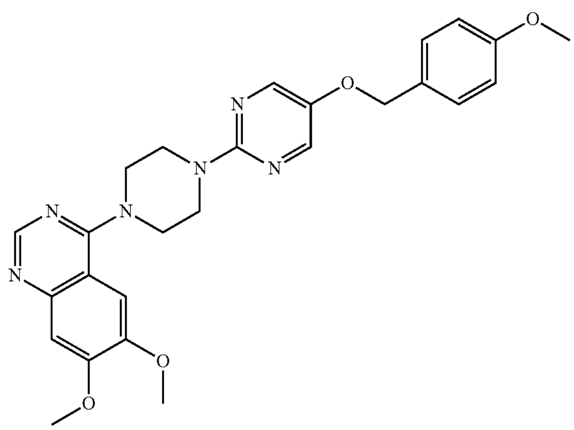 [SMILES: COc1ccc(COc2cnc(N3CCN(c4ncnc5cc(OC)c(OC)cc45)CC3)nc2)cc1] | C | D |
| 78 | 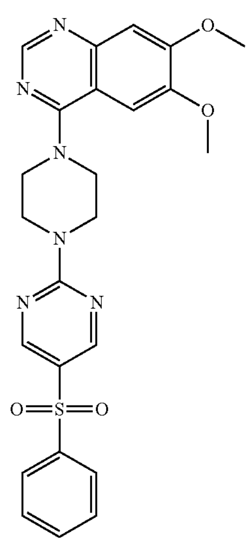 [SMILES: COc1cc2ncnc(N3CCN(c4ncc(S(=O)(=O)c5ccccc5)cn4)CC3)c2cc1OC] | C | D |

-continued
| Compound Id | Structure | INH-KITD816V ENZ-KM IC50 (nM) (Num) | INH-KITWT ENZ-KM IC50 (nM) (Num) |
|---|---|---|---|
| 79 | 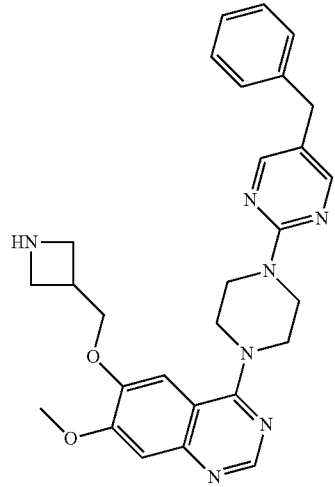 [SMILES: COc1cc2ncnc(N3CCN(c4ncc(Cc5ccccc5)cn4)CC3)c2cc1OCC1CNC1] | B | B |
| 80 | 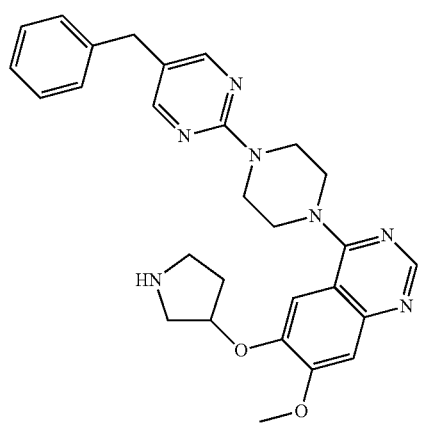 [SMILES: COc1cc2ncnc(N3CCN(c4ncc(Cc5ccccc5)cn4)CC3)c2cc1OC1CCNC1] | B | B |
| 81 | 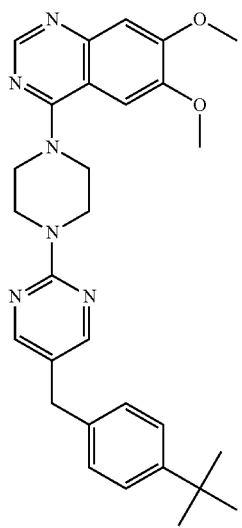 [SMILES: COc1cc2ncnc(N3CCN(c4ncc(Cc5ccc(C(C)(C)C)cc5)cn4)CC3)c2cc1OC] | C | D |

| Compound Id | Structure | INH-KITD816V ENZ-KM IC50 (nM) (Num) | INH-KITWT ENZ-KM IC50 (nM) (Num) |
|---|---|---|---|
| 82 | 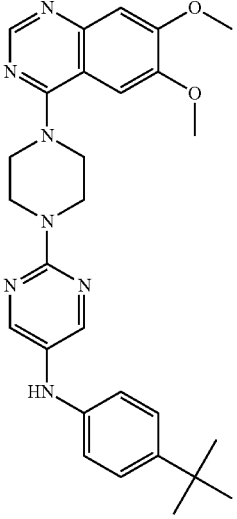 [SMILES: COc1cc2ncnc(N3CCN(c4ncc(Nc5ccc(C(C)(C)C)cc5)cn4)CC3)c2cc1OC] | D | D |
| 83 | 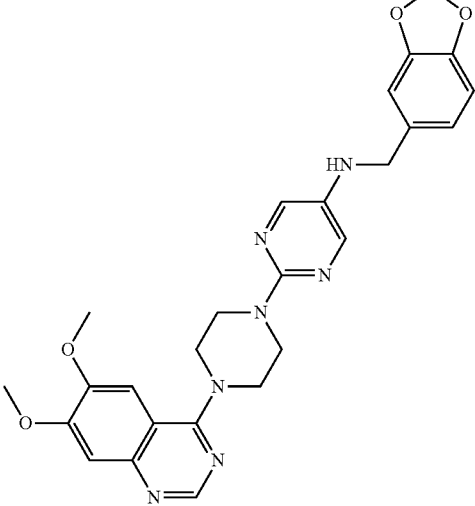 | D | |
| 84 | 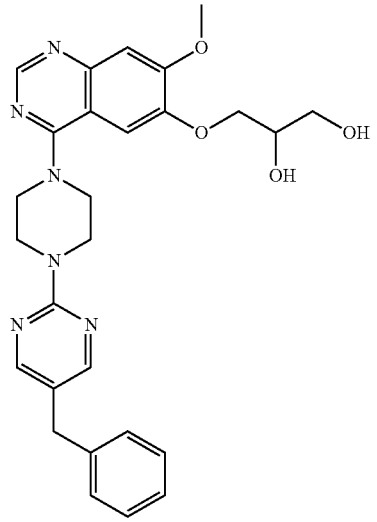 [SMILES: COc1cc2ncnc(N3CCN(c4ncc(Cc5ccccc5)cn4)CC3)c2cc1OCC(O)CO] | B | B |

-continued
| Compound Id | Structure | INH-KITD816V ENZ-KM IC50 (nM) (Num) | INH-KITWT ENZ-KM IC50 (nM) (Num) |
|---|---|---|---|
| 85 | 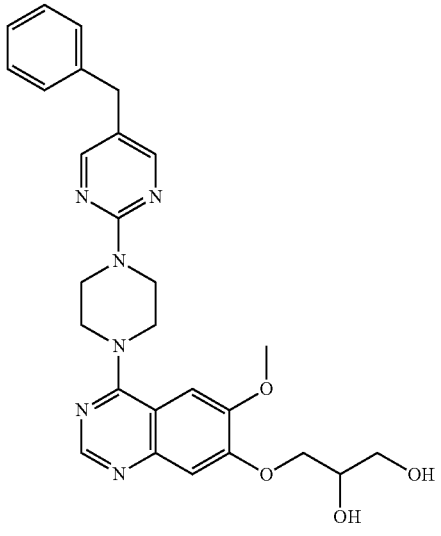 [SMILES: COc1cc2c(N3CCN(c4ncc(Cc5ccccc5)cn4)CC3)ncnc2cc1OCC(O)CO] | B | B |
| 86 | 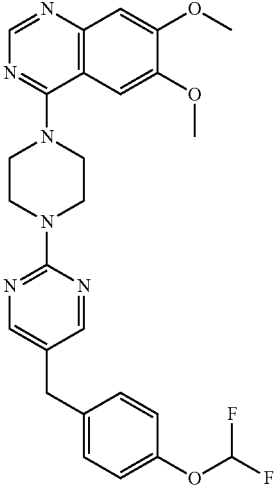 [SMILES: COc1cc2ncnc(N3CCN(c4ncc(Cc5ccc(OC(F)F)cc5)cn4)CC3)c2cc1OC] | B | C |
| 87 | 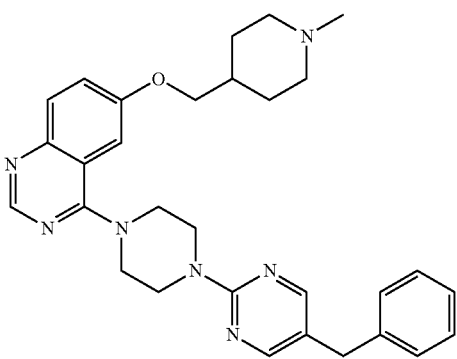 [SMILES: CN1CCC(COc2ccc3ncnc(N4CCN(c5ncc(Cc6ccccc6)cn5)CC4)c3c2)CC1] | B | C |

-continued

| Compound Id | Structure | INH-KITD816V ENZ-KM IC50 (nM) (Num) | INH-KITWT ENZ-KM IC50 (nM) (Num) |
|---|---|---|---|
| 88 | 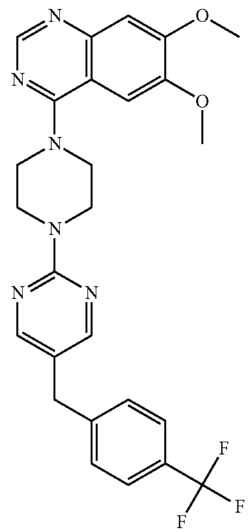 [SMILES: COc1cc2ncnc(N3CCN(c4ncc(Cc5ccc(C(F)(F)F)cc5)cn4)CC3)c2cc1OC] | C | C |
| 89 | 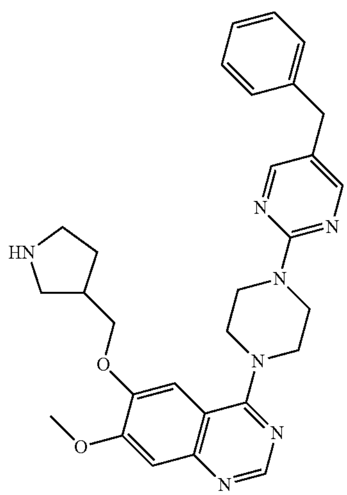 [SMILES: COc1cc2ncnc(N3CCN(c4ncc(Cc5ccccc5)cn4)CC3)c2cc1OCC1CCNC1] | A | B |
| 90 | 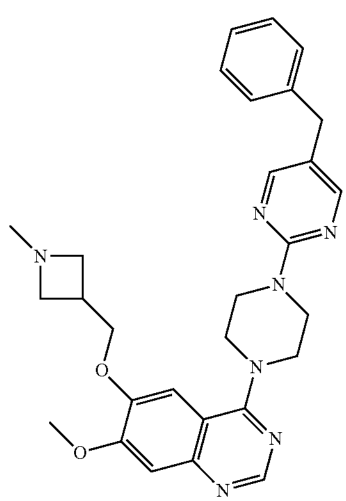 [SMILES: COc1cc2ncnc(N3CCN(c4ncc(Cc5ccccc5)cn4)CC3)c2cc1OCC1CN(C)C1] | A | B |

-continued

| Compound Id | Structure | INH-KITD816V ENZ-KM IC50 (nM) (Num) | INH-KITWT ENZ-KM IC50 (nM) (Num) |
|---|---|---|---|
| 91 | 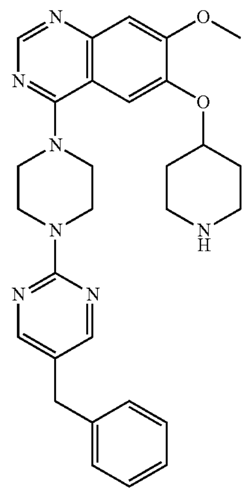 [SMILES: COc1cc2ncnc(N3CCN(c4ncc(Cc5ccccc5)cn4)CC3)c2cc1OC1CCNCC1] | B | B |
| 92 | 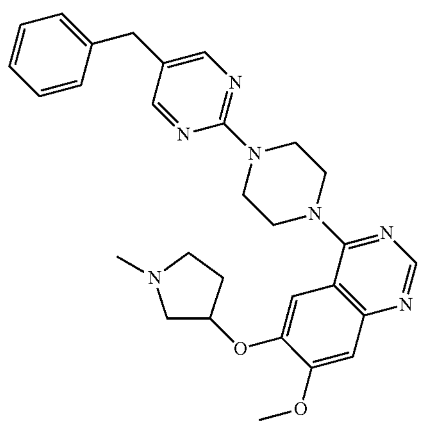 [SMILES: COc1cc2ncnc(N3CCN(c4ncc(Cc5ccccc5)cn4)CC3)c2cc1OC1CCN(C)C1] | B | C |
| 93 | 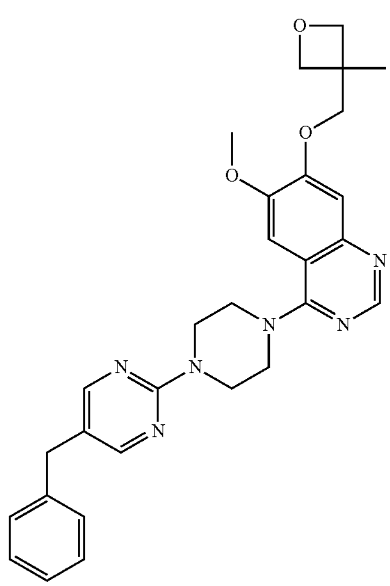 [SMILES: COc1cc2c(N3CCN(c4ncc(Cc5ccccc5)cn4)CC3)ncnc2cc1OCC1(C)COC1] | B | B |

-continued
| Compound Id | Structure | INH-KITD816V ENZ-KM IC50 (nM) (Num) | INH-KITWT ENZ-KM IC50 (nM) (Num) |
|---|---|---|---|
| 94 | 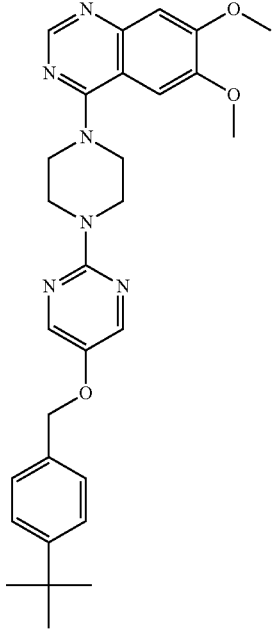 [SMILES: COc1cc2ncnc(N3CCN(c4ncc(OCc5ccc(C(C)(C)C)cc5)cn4)CC3)c2cc1OC] | D | D |
| 95 | 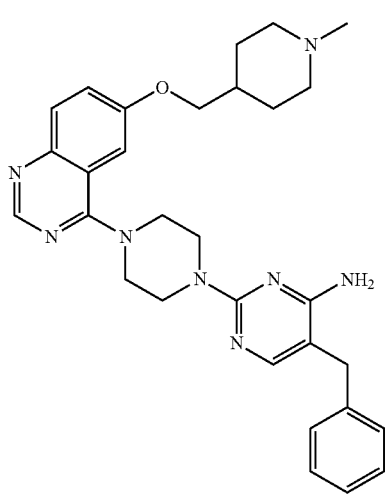 [SMILES: CN1CCC(COc2ccc3ncnc(N4CCN(c5ncc(Cc6ccccc6)c(N)n5)CC4)c3c2)CC1] | B | B |

-continued
| Compound Id | Structure | INH-KITD816V ENZ-KM IC50 (nM) (Num) | INH-KITWT ENZ-KM IC50 (nM) (Num) |
|---|---|---|---|
| 96 | 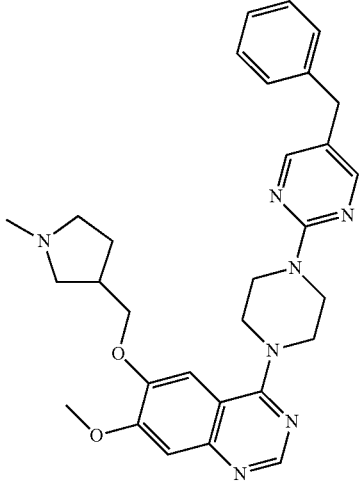 [SMILES: COc1cc2ncnc(N3CCN(c4ncc(Cc5ccccc5)cn4)CC3)c2cc1OCC1CCN(C)C1] | A | B |
| 97 | 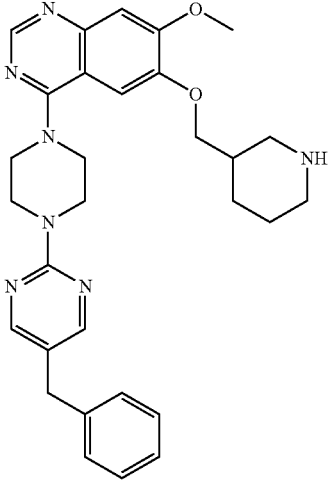 [SMILES: COc1cc2ncnc(N3CCN(c4ncc(Cc5ccccc5)cn4)CC3)c2cc1OCC1CCCNC1] | A | B |
| 98 | 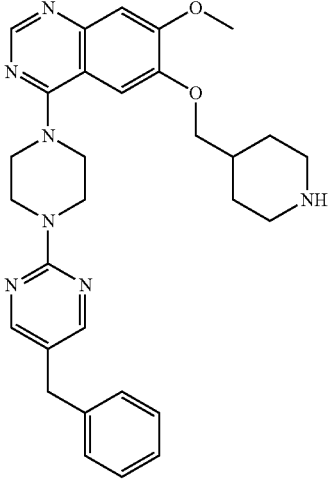 [SMILES: COc1cc2ncnc(N3CCN(c4ncc(Cc5ccccc5)cn4)CC3)c2cc1OCC1CCNCC1] | A | B |

-continued

| Compound Id | Structure | INH-KITD816V ENZ-KM IC50 (nM) (Num) | INH-KITWT ENZ-KM IC50 (nM) (Num) |
|---|---|---|---|
| 99 | 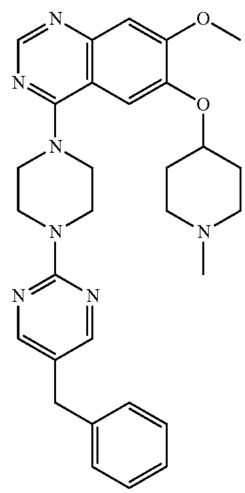 [SMILES: COc1cc2ncnc(N3CCN(c4ncc(Cc5ccccc5)cn4)CC3)c2cc1OC1CCN(C)CC1] | B | B |
| 100 | 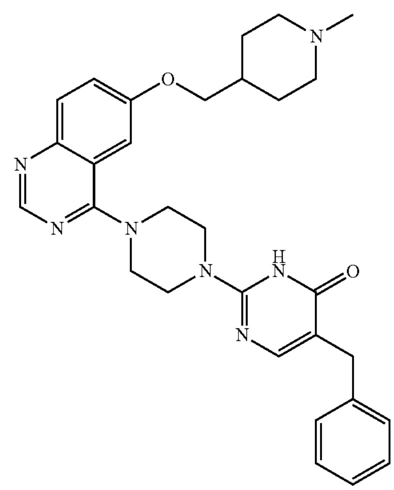 [SMILES: CN1CCC(COc2ccc3ncnc(N4CCN(c5ncc(Cc6ccccc6)c(=O)[nH]5)CC4)c3c2)CC1] | B | C |
| 101 | 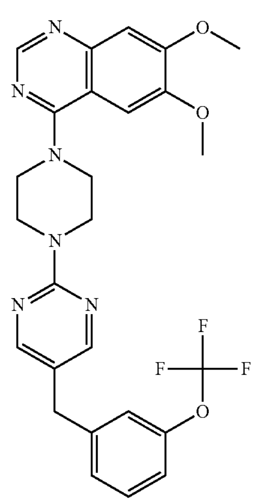 [SMILES: COc1cc2ncnc(N3CCN(c4ncc(Cc5cccc(OC(F)(F)F)c5)cn4)CC3)c2cc1OC] | C | C |

-continued
| Compound Id | Structure | INH-KITD816V ENZ-KM IC50 (nM) (Num) | INH-KITWT ENZ-KM IC50 (nM) (Num) |
|---|---|---|---|
| 102 | 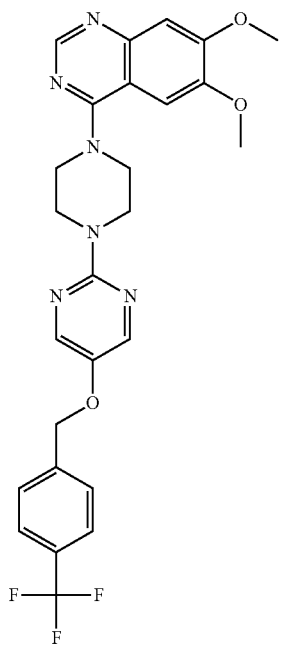 [SMILES: COc1cc2ncnc(N3CCN(c4ncc(OCc5ccc(C(F)(F)F)cc5)cn4)CC3)c2cc1OC] | D | D |
| 103 | 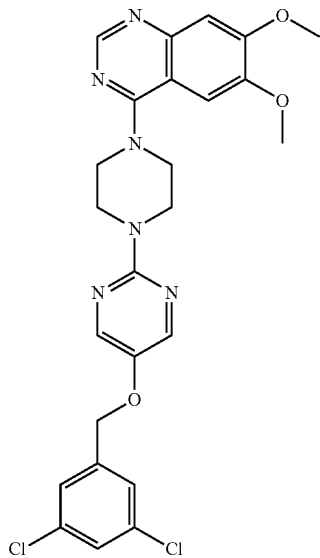 [SMILES: COc1cc2ncnc(N3CCN(c4ncc(OCc5cc(Cl)cc(Cl)c5)cn4)CC3)c2cc1OC] | D | D |

-continued
| Compound Id | Structure | INH-KITD816V ENZ-KM IC50 (nM) (Num) | INH-KITWT ENZ-KM IC50 (nM) (Num) |
| --- | --- | --- | --- |
| 104 | 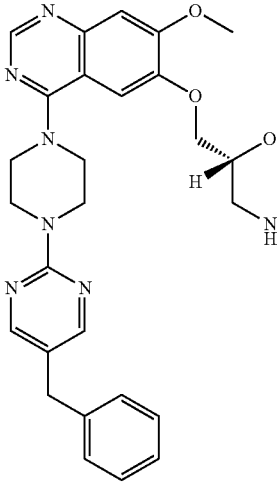 Chiral | A | B |
| 105 | 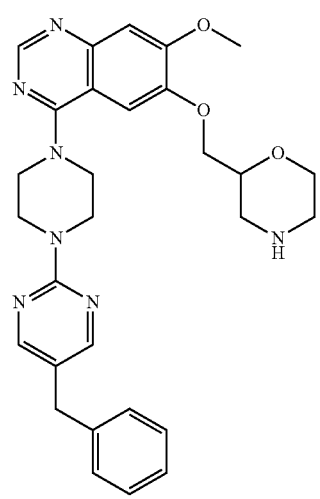 [SMILES: COc1cc2ncnc(N3CCN(c4ncc(Cc5ccccc5)cn4)CC3)c2cc1OCC1CNCCO1] | A | B |
| 106 | 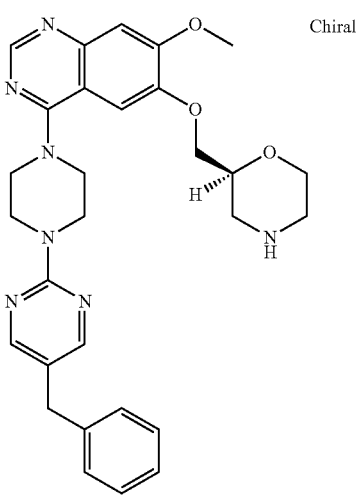 [SMILES: COc1cc2ncnc(N3CCN(c4ncc(Cc5ccccc5)cn4)CC3)c2cc1OC[C@@H]1CNCCO1] Chiral | B | B |

| Compound Id | Structure | INH-KITD816V ENZ-KM IC50 (nM) (Num) | INH-KITWT ENZ-KM IC50 (nM) (Num) |
|---|---|---|---|
| 107 | 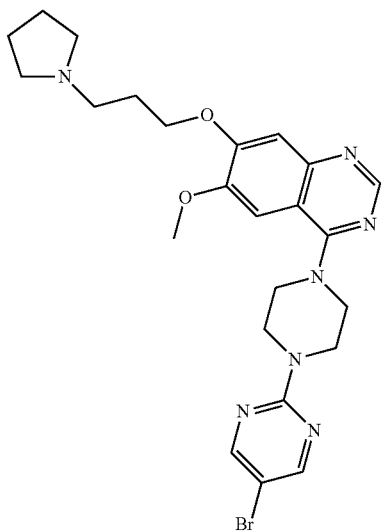 [SMILES: COc1cc2c(N3CCN(c4ncc(Br)cn4)CC3)ncnc2cc1OCCCN1CCCC1] | C | C |
| 108 | 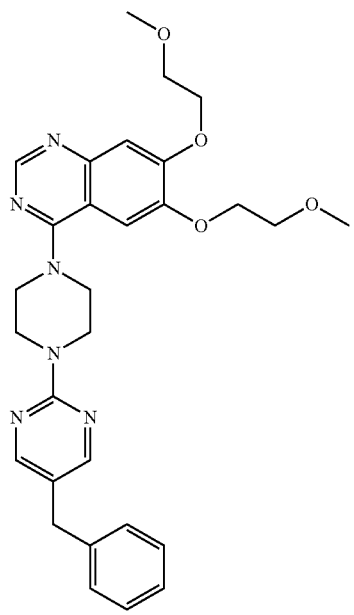 [SMILES: COCCOc1cc2ncnc(N3CCN(c4ncc(Cc5ccccc5)cn4)CC3)c2cc1OCCOC] | A | A |

-continued
| Compound Id | Structure | INH-KITD816V ENZ-KM IC50 (nM) (Num) | INH-KITWT ENZ-KM IC50 (nM) (Num) |
|---|---|---|---|
| 109 | 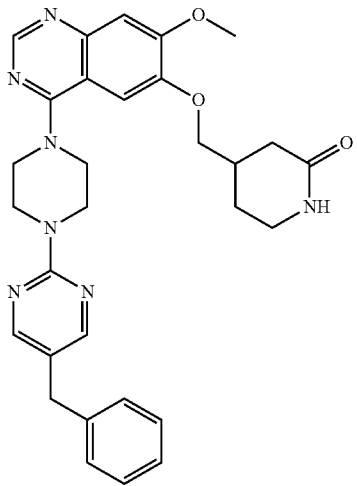 [SMILES: COc1cc2ncnc(N3CCN(c4ncc(Cc5ccccc5)cn4)CC3)c2cc1OCC1CCNC(=O)C1] | A | B |
| 110 | 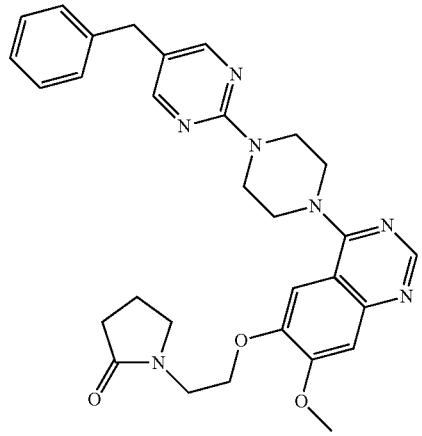 [SMILES: COc1cc2ncnc(N3CCN(c4ncc(Cc5ccccc5)cn4)CC3)c2cc1OCCN1CCCC1=O] | A | B |
| 111 | 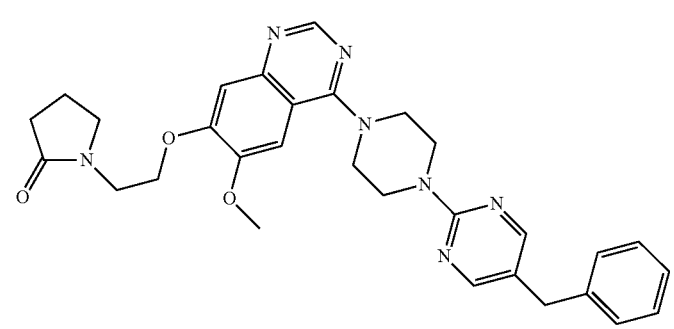 [SMILES: COc1cc2c(N3CCN(c4ncc(Cc5ccccc5)cn4)CC3)ncnc2cc1OCCN1CCCC1=O] | A | B |

-continued
| Compound Id | Structure | | INH-KITD816V ENZ-KM IC50 (nM) (Num) | INH-KITWT ENZ-KM IC50 (nM) (Num) |
|---|---|---|---|---|
| 112 | 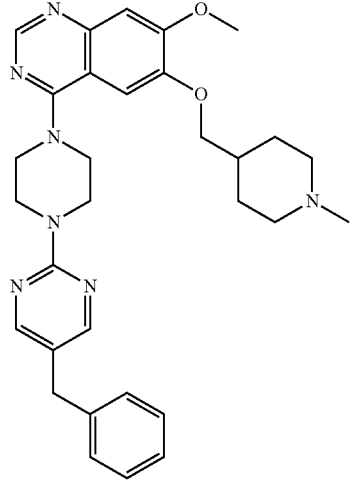 [SMILES: COc1cc2ncnc(N3CCN(c4ncc(Cc5ccccc5)cn4)CC3)c2cc1OCC1CCN(C)CC1] | | A | B |
| 113 | 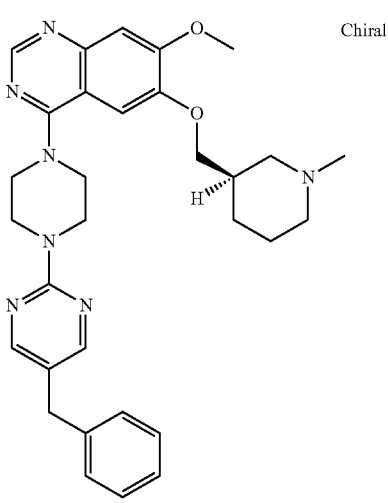 [SMILES: COc1cc2ncnc(N3CCN(c4ncc(Cc5ccccc5)cn4)CC3)c2cc1OC[C@@H]1CCCN(C)C1] | Chiral | A | B |
| 114 | 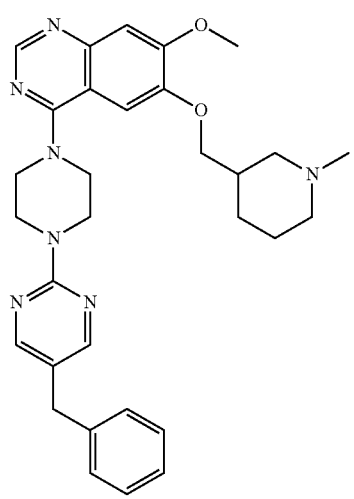 [SMILES: COc1cc2ncnc(N3CCN(c4ncc(Cc5ccccc5)cn4)CC3)c2cc1OCC1CCCN(C)C1] | | A | B |

-continued
| Compound Id | Structure | | INH-KITD816V ENZ-KM IC50 (nM) (Num) | INH-KITWT ENZ-KM IC50 (nM) (Num) |
|---|---|---|---|---|
| 115 | 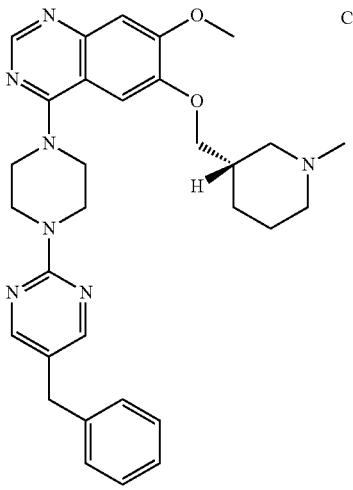 | Chiral | B | B |
| 116 | 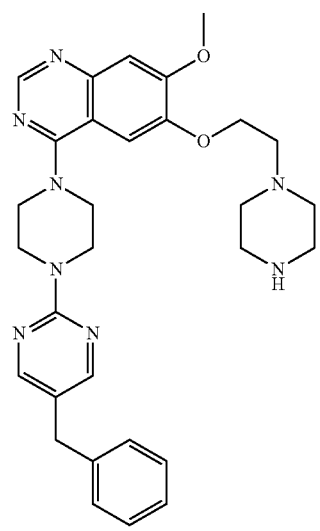 [SMILES: COc1cc2ncnc(N3CCN(c4ncc(Cc5ccccc5)cn4)CC3)c2cc1OCCN1CCNCC1] | | B | B |
| 117 | 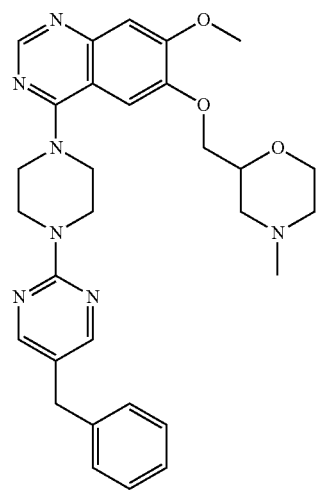 [SMILES: COc1cc2ncnc(N3CCN(c4ncc(Cc5ccccc5)cn4)CC3)c2cc1OCC1CN(C)CCO1] | | A | B |

-continued
| Compound Id | Structure | INH-KITD816V ENZ-KM IC50 (nM) (Num) | INH-KITWT ENZ-KM IC50 (nM) (Num) |
|---|---|---|---|
| 118 | 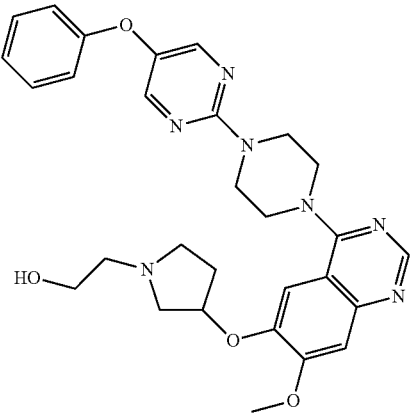 [SMILES: COc1cc2ncnc(N3CCN(c4ncc(Oc5ccccc5)cn4)CC3)c2cc1OC1CCN(CCO)C1] | B | B |
| 119 | 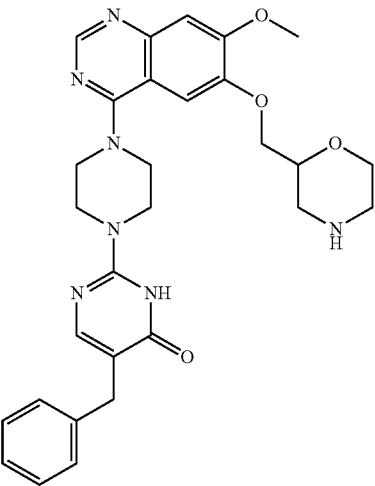 [SMILES: COc1cc2ncnc(N3CCN(c4ncc(Cc5ccccc5)c(=O)[nH]4)CC3)c2cc1OCC1CNCCO1] | A | A |
| 120 | 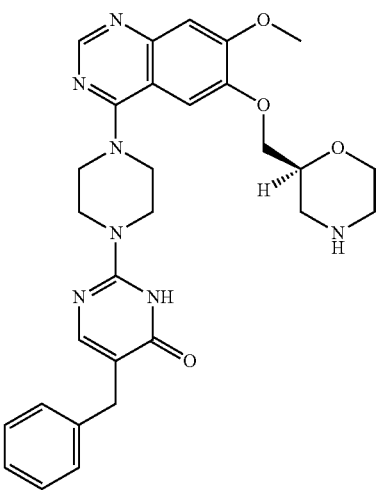 Chiral | A | A |

-continued
| Compound Id | Structure | INH-KITD816V ENZ-KM IC50 (nM) (Num) | INH-KITWT ENZ-KM IC50 (nM) (Num) |
|---|---|---|---|
| 121 | 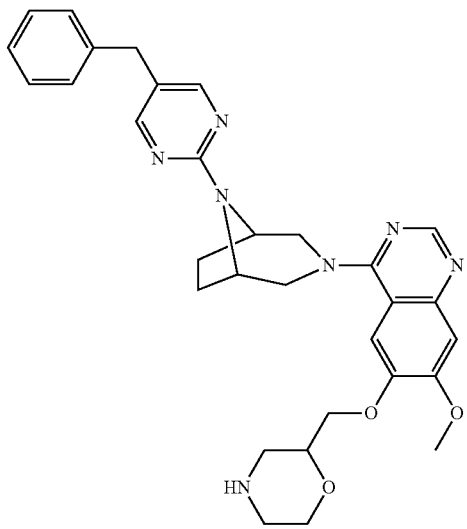 [SMILES: COc1cc2ncnc(N3CC4CCC(C3)N4c3ncc(Cc4ccccc4)cn3)c2cc1OCC1CNCCO1] | A | B |
| 122 | 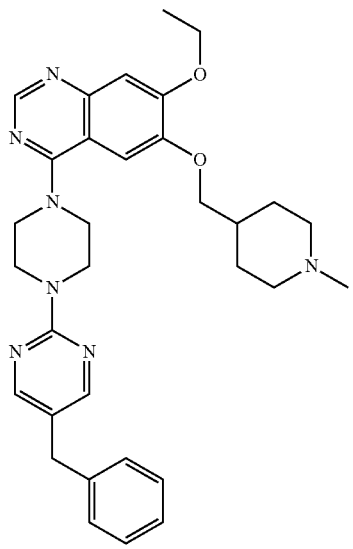 [SMILES: CCOc1cc2ncnc(N3CCN(c4ncc(Cc5ccccc5)cn4)CC3)c2cc1OCC1CCN(C)CC1] | A | A |

-continued
| Compound Id | Structure | INH-KITD816V ENZ-KM IC50 (nM) (Num) | INH-KITWT ENZ-KM IC50 (nM) (Num) |
|---|---|---|---|
| 123 | 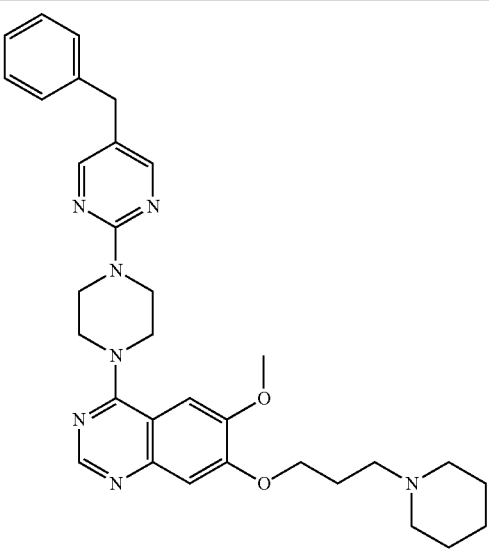 [SMILES: COc1cc2c(N3CCN(c4ncc(Cc5ccccc5)cn4)CC3)ncnc2cc1OCCCN1CCCCC1] | C | C |
| 124 | 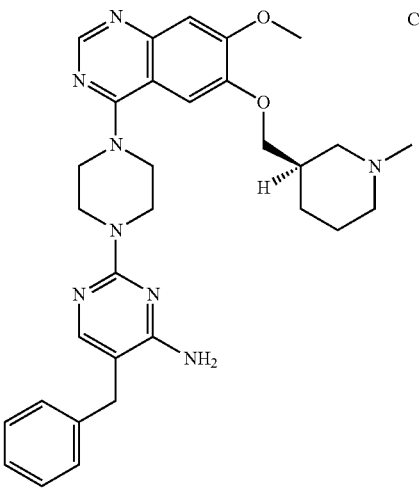 Chiral | A | A |
| 125 | 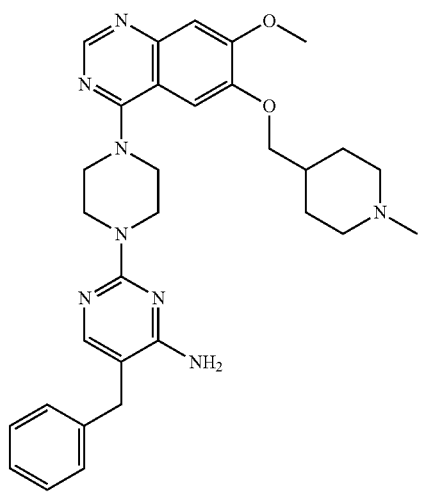 [SMILES: COc1cc2ncnc(N3CCN(c4ncc(Cc5ccccc5)c(N)n4)CC3)c2cc1OCC1CCN(C)CC1] | A | A |

-continued
| Compound Id | Structure | INH-KITD816V ENZ-KM IC50 (nM) (Num) | INH-KITWT ENZ-KM IC50 (nM) (Num) |
|---|---|---|---|
| 126 | 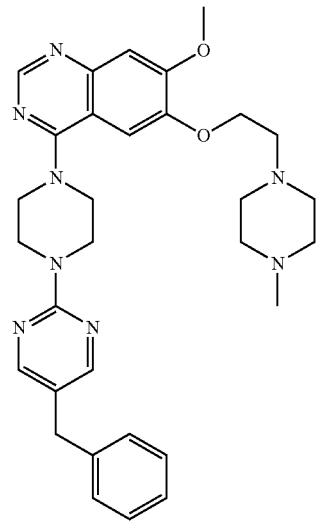 [SMILES: COc1cc2ncnc(N3CCN(c4ncc(Cc5ccccc5)cn4)CC3)c2cc1OCCN1CCN(C)CC1] | B | B |
| 127 | 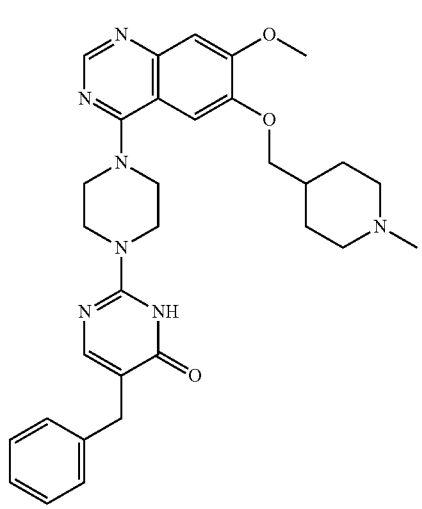 [SMILES: COc1cc2ncnc(N3CCN(c4ncc(Cc5ccccc5)c(=O)[nH]4)CC3)c2cc1OCC1CCN(C)CC1] | A | A |
| 128 | 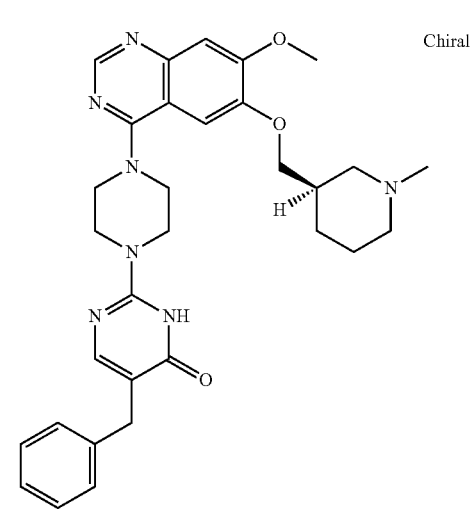 [SMILES: COc1cc2ncnc(N3CCN(c4ncc(Cc5ccccc5)c(=O)[nH]4)CC3)c2cc1OC[C@@H]1CCCN(C)C1] Chiral | B | B |

-continued
| Compound Id | Structure | INH-KITD816V ENZ-KM IC50 (nM) (Num) | INH-KITWT ENZ-KM IC50 (nM) (Num) |
| --- | --- | --- | --- |
| 129 | 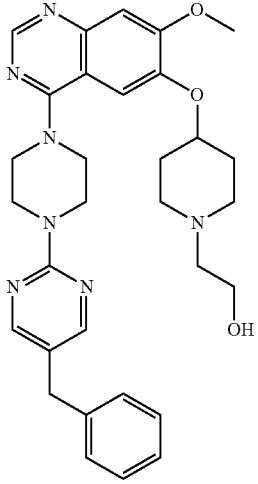 [SMILES: COc1cc2ncnc(N3CCN(c4ncc(Cc5ccccc5)cn4)CC3)c2cc1OC1CCN(CCO)CC1] | B | B |
| 130 | 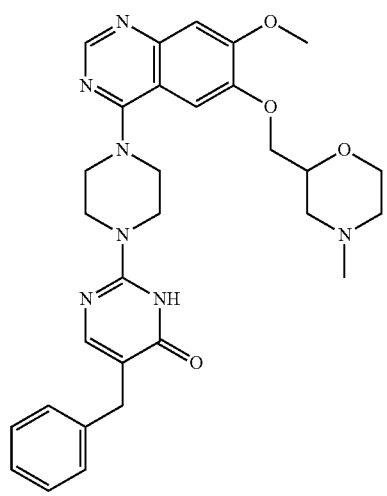 [SMILES: COc1cc2ncnc(N3CCN(c4ncc(Cc5ccccc5)c(=O)[nH]4)CC3)c2cc1OCC1CN(C)CCO1] | B | A |
| 131 | 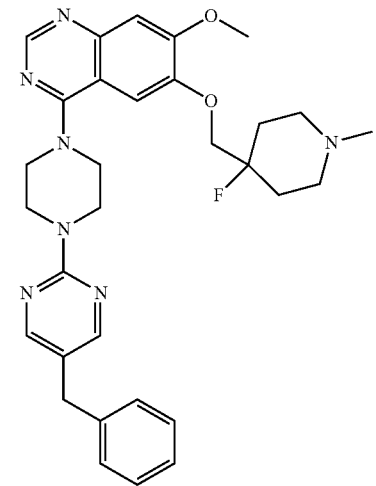 [SMILES: COc1cc2ncnc(N3CCN(c4ncc(Cc5ccccc5)cn4)CC3)c2cc1OCC1(F)CCN(C)CC1] | A | A |

| Compound Id | Structure | INH-KITD816V ENZ-KM IC50 (nM) (Num) | INH-KITWT ENZ-KM IC50 (nM) (Num) |
|---|---|---|---|
| 132 | 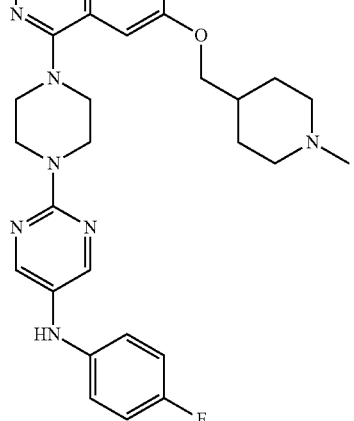 | B | B |
| 133 | 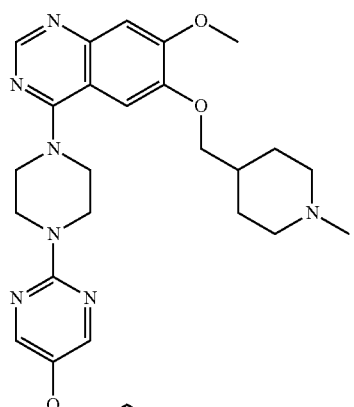 | B | B |
| 134 | 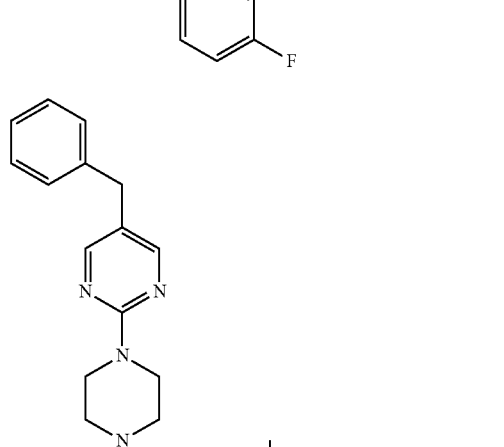 | A | A |

-continued
| Compound Id | Structure | INH-KITD816V ENZ-KM IC50 (nM) (Num) | INH-KITWT ENZ-KM IC50 (nM) (Num) |
|---|---|---|---|
| 135 | 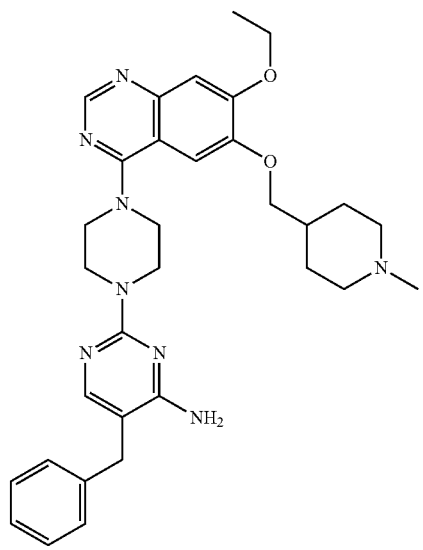 [SMILES: CCOc1cc2ncnc(N3CCN(c4ncc(Cc5ccccc5)c(N)n4)CC3)c2cc1OCC1CCN(C)CC1] | A | A |
| 136 | 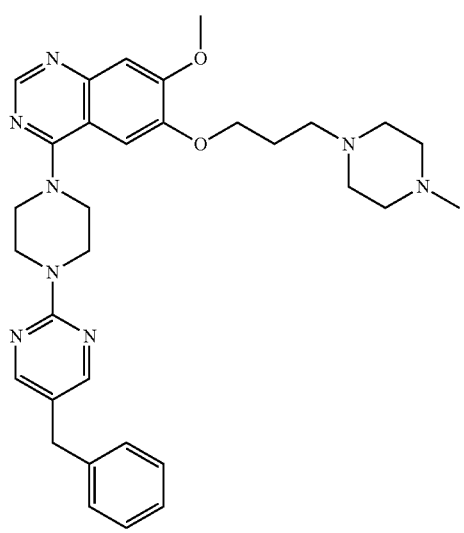 [SMILES: COc1cc2ncnc(N3CCN(c4ncc(Cc5ccccc5)cn4)CC3)c2cc1OCCCN1CCN(C)CC1] | A | B |

-continued
| Compound Id | Structure | INH-KITD816V ENZ-KM IC50 (nM) (Num) | INH-KITWT ENZ-KM IC50 (nM) (Num) |
| --- | --- | --- | --- |
| 137 | 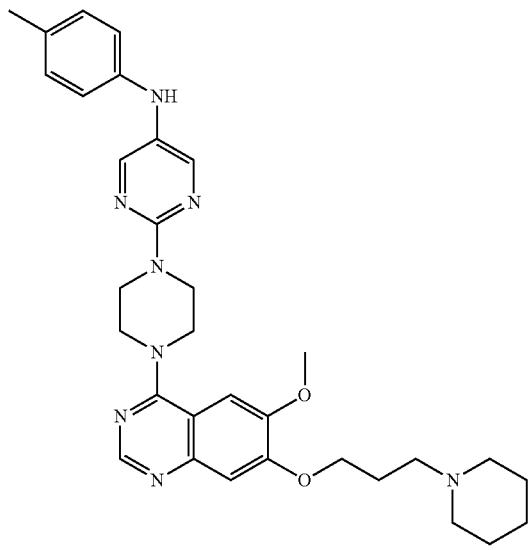 [SMILES: COc1cc2c(N3CCN(c4ncc(Nc5ccc(C)cc5)cn4)CC3)ncnc2cc1OCCCN1CCCCC1] | B | B |
| 138 | 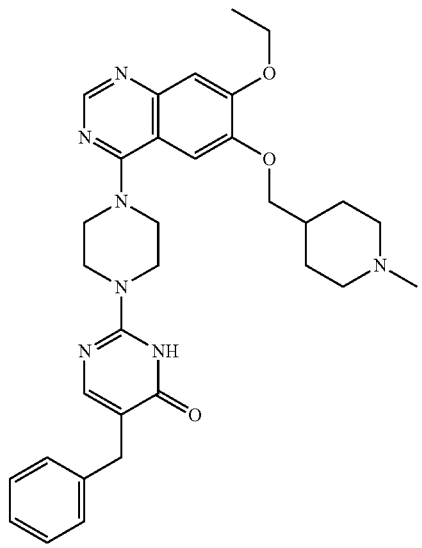 [SMILES: CCOc1cc2ncnc(N3CCN(c4ncc(Cc5ccccc5)c(=O)[nH]4)CC3)c2cc1OCC1CCN(C)CC1] | A | A |

| Compound Id | Structure | INH-KITD816V ENZ-KM IC50 (nM) (Num) | INH-KITWT ENZ-KM IC50 (nM) (Num) |
|---|---|---|---|
| 139 | 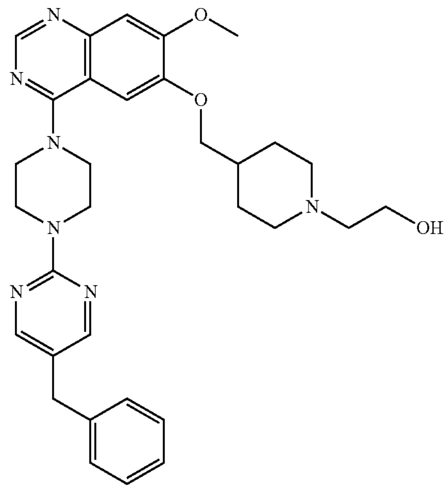 [SMILES: COc1cc2ncnc(N3CCN(c4ncc(Cc5ccccc5)cn4)CC3)c2cc1OCC1CCN(CCO)CC1] | B | B |
| 140 | 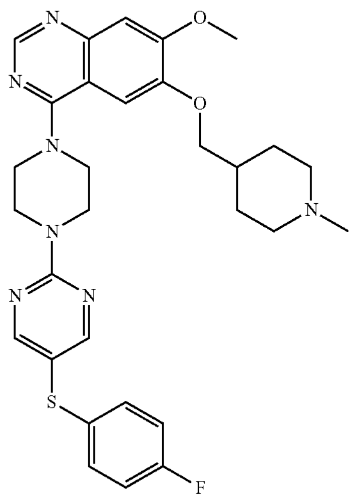 | B | B |

The following compounds were at least 100 times more potent against the D816V mutant than against the wild-type Kit: 1; 18; 20; 47; 57; 62; 73; and 77.

The following compounds were at least 50 times, but less than 100 times, more potent against the D816V mutant than against the wild-type Kit: 46; 75; 78; 89; 94; 96; 103; and 136.

The following compounds were at least 25 times, but less than 50 times, more potent against the D816V mutant than against the wild-type Kit: 4; 5; 6; 7; 8; 11; 16; 22; 24; 25; 33; 36; 37; 39; 40; 43; 45; 48; 58; 64; 66; 70; 71; 76; 79; 81; 86; 87; 90; 94; 95; 97; 99; 101; 106; 107; 108; 109; 110; 111; 112; 113; 114; 116; 118; 121; 126; and 139.

The following compounds were at least 10 times, but less than 25 times, more potent against the D816V mutant than against the wild-type Kit: 9; 10; 12; 13; 14; 15; 17; 26; 27; 29; 30; 31; 32; 35; 38; 42; 44; 49; 51; 52; 53; 54; 55; 56; 59; 60; 61; 63; 65; 69; 74; 80; 82; 84; 85; 88; 91; 98; 104; 105; 117; 120; 122; 123; 124; 131; 132; 133; 134; and 137.

The following compounds were at least 5 times, but less than 10 times, more potent against the D816V mutant than against the wild-type Kit: 3; 34; 100; 102; 119; 125; 127; 128; 130; and 135.

The following compounds were less than 5 times more potent against the D816V mutant than against the wild-type Kit: 19; 21; 23; 28; 41k; 50; 67; 68; 129; and 138.

Cellular Activity

HMC1.2 proliferation assay: 1000 HMC1.2 cells were incubated in 22 ul culture media (IMDM, 10% calf serum with Iron) in each well of a 384-well plate overnight in a tissue culture incubator (5% $CO_2$, 37° C.). A 10 point dose concentration series of compound (25 uM-1.5 nM) were then added to the cells as 3.1 ul compound solution to each well (0.25% DMSO final concentration). After 3 days incubation in tissue culture incubator, 25 ul CellTiter-Glo (Promega) solution was added to each well for ATP/cell viability measurement. Luminescence signal was obtained on Envision (Perkin Elmer) by US Lum 384 protocol. Data was normalized to 0% and 100% inhibition controls and the IC50 was calculated using Four Parameter Logistic IC50 curve fitting.

HMC1.2 autophosphorylation assay: 10,000 HMC1.2 cells were incubated in 22 ul culture media (phenol-red free IMDM, no serum) in each well of a 384-well plate and serum starved overnight in a tissue culture incubator (5% $CO_2$, 37° C.). A 10-point dose concentration series of compound (25 uM-95.4 pM) were then added to the cells in a volume of 3.1 ul to each well (0.25% DMSO final concentration). After 90 minutes, 6 ul of 5× AlphaLISA Lysis Buffer (Perkin Elmer) supplemented with a protease and phosphatase inhibitor cocktail (Cell Signaling Technologies) was added to each well and shaken at 450 rpm for 15 minutes at 4° C. 10 ul of phospho-Y719 c-Kit and total c-Kit antibodies (15 nM final concentration, Cell Signaling Technologies) and 50 ug/ml AlphaLISA rabbit acceptor beads (Perkin Elmer) were added to each well and shaken at 300 rpm at room temperature for 2 hours. 10 ul of 100 ug/ml streptavidin donor beads (Perkin Elmer) were added to each well, blocked from light with aluminum adhesive and shaken at 300 rpm at room temperature for 2 hours. Fluorescence signal was obtained on Envision (Perkin Elmer) by AlphaScreen 384 well HTS protocol. Data was normalized to 0% and 100% inhibition controls and the IC50 was calculated using Four Parameter Logistic IC50 curve fitting.

The Table below shows the activity of compounds in a Mast cell leukemia cell line, HMC 1.2. This cell line contains Kit mutated at positions V560G and D816V resulting in constitutive activation of the kinase. The following compounds were tested in an assay to measure direct inhibition Kit D816V kinase activity by assaying Kit autophosphorylation at tyrosine 719 on the Kit protein. In addition, these compounds were assayed for their ability to inhibit the dependence of these cells on Kit kinase activity by disrupting their growth and proliferation.

In the Table below, the following designations are used: <10 nM=A; 10.01-100 nM=B; 100.01-1000 nM=C; and 1000-10000 nM=D, >10000.01 nM=E.

| Compound | HMC1.2 Autophosphorylation IC50 | HMC1.2 Proliferation IC50 |
| --- | --- | --- |
| 1 | E | D |
| 5 | | D |
| 7 | | D |
| 13 | C | D |
| 22 | | D |
| 23 | C | D |
| 30 | | D |
| 1 | E | D |
| 35 | C | C |
| 36 | C | D |
| 42 | | D |
| 79 | B | D |
| 84 | C | D |
| 85 | C | D |
| 88 | | E |
| 98 | B | D |
| 99 | C | D |
| 105 | B | C |
| 107 | | D |
| 108 | B | C |
| 109 | B | D |
| 111 | C | D |
| 112 | B | D |
| 105 | B | C |
| 119 | D | E |
| 123 | D | D |
| 125 | A | C |
| 134 | B | C |
| 136 | C | D |
| 137 | C | D |

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound having structural formula I:

[Structure I]

or a pharmaceutically acceptable salt or a tautomer thereof, wherein:
- each $R^4$ is independently selected from —C(O)N($R^2$)($R^2$), —CN, —(C$_0$-C$_4$ alkylene)-N($R^2$)($R^2$), —O—(C$_1$-C$_4$ alkylene)-O—(C$_1$-C$_3$ alkyl), —(C$_1$-C$_4$ alkylene)-O —(C$_1$-C$_3$ alkyl), and —O—(C$_0$-C$_4$ alkylene)-($R^1$), wherein $R^1$ is selected from —C$_1$-C$_4$ alkyl and heterocyclyl;
- each $R^2$ is independently selected from hydrogen and unsubstituted C$_1$-C$_4$ alkyl
- each $R^6$ is independently selected from —C$_1$-C$_4$ alkyl or two $R^6$ bound to the same carbon atom are taken together to form oxo, or two $R^6$ bound to different carbon atoms are taken together to form methylene, ethane-1,2-diyl, or propane-1,2-diyl forming a ring that is bridged to the piperazine-1,4-diyl portion of the compound;
- each $R^8$ is independently selected from halo, —OH, —N($R^2$)($R^2$), C$_1$-C$_4$ alkyl, and —O—(C$_1$-C$_4$ alkyl);
- L is selected from a bond, —(C$_1$-C$_4$ alkylene)-, —O—, —S—, —SO$_2$—, —N($R^2$)—, —O—(C$_1$-C$_4$ alkylene)-, —(C$_1$-C$_4$ alkylene)-O—, —(C$_1$-C$_4$ alkylene)-N($R^2$)—, —N($R^2$)—(C$_1$-C$_4$ alkylene)-, —N($R^2$)—CO—(C$_1$-C$_4$ alkylene)-, and —CO—N($R^2$)—(C$_1$-C$_4$ alkylene)-;
- n is 1, 2, or 3;
- m is 0, 1, 2, 3, or 4;
- p is 0, 1, or 2;
- q is 0, 1, 2, or 3;
- ring A is monocyclic or bicyclic aryl, heteroaryl, carbocyclyl or heterocyclyl;
- each $R^{10}$ is independently selected from halo, —OH, —CN, —C(O)N($R^2$)($R^2$), C$_1$-C$_4$ alkyl, —O—(C$_1$-C$_4$ alkyl), and heterocyclyl, or two $R^{10}$ bound to adjacent ring carbon atoms are taken together to form methylenedioxy;
- wherein unless otherwise specified any alkyl, or alkylene portion of the compound is optionally substituted.

2. The compound of claim 1, wherein
any alkyl, or alkylene portion of the compound is optionally and independently substituted with one or more substituents independently selected from halo, —OH, C$_1$-C$_4$ alkyl, C$_1$-C$_4$ haloalkyl, —O—(C$_1$-C$_4$ alkyl), and =O; and
any heterocyclyl portion of the compound is optionally and independently substituted with one or more substituents independently selected from halo, —OH, C$_1$-C$_4$ alkyl, C$_1$-C$_4$ haloalkyl, —O—(C$_1$-C$_4$ alkyl), and =O.

3. The compound of claim 1, wherein:
each $R^4$ is independently selected from —C(O)N($R^2$)($R^2$), —O—(C$_1$-C$_4$ alkylene)-O—(C$_1$-C$_3$ alkyl), and —O—(C$_0$-C$_4$ alkylene)-($R^1$), wherein:
- $R^1$ is selected from —C$_1$-C$_4$ alkyl, and a saturated heterocyclyl;
- each $R^2$ is independently selected from hydrogen and methyl;
- each alkyl or alkylene is optionally substituted with one or more substituents independently selected from halo, —OH and —O—(C$_1$-C$_3$ alkyl);
- the saturated heterocyclyl is optionally substituted on a substitutable ring nitrogen with methyl; and
- the saturated heterocyclyl is optionally substituted on a substitutable ring carbon with one or more substituents independently selected from methyl, halo, —OH.

4. The compound of claim 3, wherein each $R^4$ is independently selected from C(O)NH$_2$, —OCF$_2$, —OCH$_2$CH$_3$, —OCH$_3$, 1-methyl-4-fluoropiperidin-4-ylmethoxy, 1-(2-hydroxyethyl)-piperidin-4-ylmethoxy, 1-(2-hydroxyethyl)-piperidin-4-yloxy, 1-(2-hydroxyethyl)-pyrrolidin-3-yloxy, 1-methylazetidin-3-ylmethoxy, 1-methylpiperidin-3-ylethoxy, 1-methylpiperidin-3-ylmethoxy, 1-methylpiperidin-4-ylmethoxy, 1-methylpiperidin-4-yloxy, 1-methylpyrrolidin-3-ylmethoxy, 1-methylpyrrolidin-3-yloxy, 2,3-dihydroxypropoxy, 2-oxopiperidin-4-ylmethoxy, 2-oxopyrrolidin-1-ylethoxy, 3-methyloxetan-3-ylmethoxy, 4-methylmorpholin-2-ylmethoxy, 4-methylpiperazin-1-ylethoxy, 4-methylpiperazin-1-ylpropoxy, azetidin-3-ylmethoxy, methoxyethoxy, morpholin-2-ylmethoxy, piperidin-1-ylpropoxy, piperidin-3-ylmethoxy, piperidin-4-ylmethoxy, piperidin-4-yloxy, pyrrolidin-1-ylpropoxy, pyrrolidin-3-ylmethoxy, and pyrrolidin-3-yloxy.

5. The compound of claim 4, wherein each $R^4$ is independently selected from OCH$_2$CH$_3$, OCH$_3$, 1-(2-hydroxyethyl)-piperidin-4-ylmethoxy, 1-(2-hydroxyethyl)-piperidin-4-yloxy, 1-(2-hydroxyethyl)-pyrrolidin-3-yloxy, 1-methyl-4-fluoropiperidin-4-ylmethoxy, 1-methylazetidin-3-ylmethoxy, 1-methylpiperidin-3-ylethoxy, 1-methylpiperidin-3-ylmethoxy, 1-methylpiperidin-4-ylmethoxy, 1-methylpiperidin-4-yloxy, 1-methylpyrrolidin-3-ylmethoxy, 1-methylpyrrolidin-3-yloxy, 2,3-dihydroxypropoxy, 2-oxopiperidin-4-ylmethoxy, 2-oxopyrrolidin-1-yleithoxy, 3-methyloxetan-3-ylmethoxy, 4-methylmorpholin-2-ylmethoxy, 4-methylpiperazin-1-ylethoxy, 4-methylpiperazin-1-ylpropoxy, azetidin-3-ylmethoxy, methoxyethoxy, morpholin-2-ylmethoxy, piperidin-1-ylpropoxy, piperidin-3-ylmethoxy, piperidin-4-ylmethoxy, piperidin-4-yloxy, pyrrolidin-3-ylmethoxy, and pyrrolidin-3-yloxy.

6. The compound of claim 1, wherein each $R^6$ is independently selected from C$_1$-C$_4$ alkyl, or two $R^6$ bound to the same carbon atom are taken together to form oxo, or two $R^6$ on non-adjacent carbon ring atoms are taken together to form ethane-1,2-diyl, propane-1,3-diyl or butane-1,4-diyl thereby forming a ring that is bridged to the piperazine-1,4-diyl portion of the compound.

7. The compound of claim 6, wherein each $R^6$ is independently methyl or two $R^6$ bound to the same carbon atom are taken together to form oxo, or two $R^6$ non-adjacent carbon ring atoms are taken together to form an ethane-1,2-diyl thereby forming a ring that is bridged to the piperazine-1,4-diyl portion of the compound.

8. The compound of claim 1, wherein each $R^8$ is independently selected from —OH and —NH$_2$.

9. The compound of claim 1, wherein each $R^{10}$ is independently selected from —OH, —OCH$_3$, —F, —CH$_3$, —CN, —C(O)NH₂, —OCF₂, —Cl, CF₃, —OCF₃, and t-butyl, or two R¹⁰ are taken together to form methylenedioxy.

10. The compound of claim 9, wherein each R¹⁰ is independently selected from OH, —OCH₃, —F, —CH₃, —CN, —C(O)NH₂, —OCF₂, and —Cl.

11. The compound of claim 1, wherein L is selected from a bond, —CH₂—, —CH₂CH₂—, —NH—, —O—, —S—, —CH₂O—*, —OCH₂—*, —OCH(CH₃)—*, —N(CH₃)CH₂—*, —NHCH₂—*, —NHC(O)CH₂—*, —C(O)NH—*, —NHCH(CH₃)—*, and —SO₂—, wherein "*" represents a portion of L bound to ring A.

12. The compound of claim 11, wherein L is selected from —CH₂—, —CH₂CH₂—, —NH—, —O—, —S—, —CH₂O—*,—N(CH₃)CH₂—*, —OCH(CH₃)—*, and —OCH(CH₃)—*.

13. The compound of claim 1, wherein ring A is selected from phenyl, thiophenyl, indolinyl, 1,2,3,4-tetrahydroquinoline, pyridinyl, thiophenyl, and C₃-C₆ cycloalkyl.

14. The compound of claim 13, wherein ring A is selected from phenyl, and thiophen-2-yl.

15. A compound having the structural formula II:

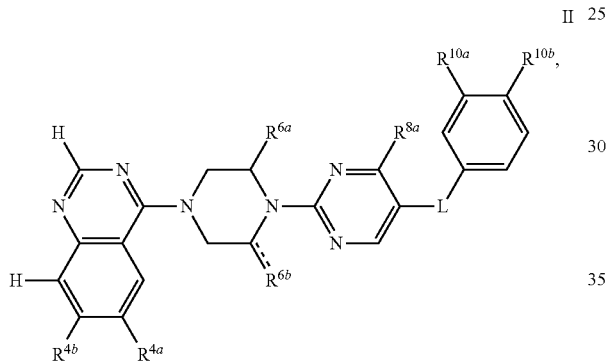

II or a pharmaceutically acceptable salt or tautomer thereof, wherein:
one of R⁴ᵃ or R⁴ᵇ is selected from, —O—CH₃, —O—CH₂CH₃ and —O—CH₂CH₂—O—CH₃;
the other of R⁴ᵃ or R⁴ᵇ is selected from —O—CH₃, —O—CH₂CH₃, —O—CH₂CH₂—O—CH₃ and —(C₀-C₄ alkylene)-(saturated heterocyclyl), wherein
the saturated heterocyclyl is optionally substituted on a substitutable ring nitrogen with methyl; and
the saturated heterocyclyl is optionally substituted on a substitutable ring carbon with one or more substituents independently selected from methyl, halo, and —OH;
R⁶ᵃ is hydrogen;
R⁶ᵇ is selected from hydrogen, and —CH₃ when ---- is a single bond, and R⁶ᵇ is =O, when ---- is a double bond; or
R⁶ᵃ and R⁶ᵇ are taken together with the carbon atoms to which they are bound to form ethane-1,2-diyl thereby forming a ring bridged to the piperazine-1,4-diyl portion of the compound;
R⁸ᵃ is selected from hydrogen, —NH₂ and —OH;

L is selected from —CH₂—, —CH₂CH₂—, —NH—, —O—, —S—, —CH₂O—*,—N(CH₃)CH₂—*, —OCH(CH₃)—*, and —OCH(CH₃)—*;
R¹⁰ᵃ is selected from hydrogen, —OCH₃, —C(O)NH₂ and halo; and
R¹⁰ᵇ is selected from hydrogen, —OCH₃, —OCF₂, halo, —CH₃, CN, and OH.

16. The compound of claim 15, wherein:
one of R⁴ᵃ or R⁴ᵇ is selected from hydrogen, —O—CH₃, —O—CH₂CH₃ and —O—CH₂CH₂—O—CH₃;
the other of R⁴ᵃ or R⁴ᵇ is selected from —O—CH₃, —O—CH₂CH₃, —O—CH₂CH₂—O—CH₃, 1-(2-hydroxyethyl)-piperidin-4-ylmethoxy, 1-(2-hydroxyethyl)-piperidin-4-yloxy, 1-(2-hydroxyethyl)-pyrrolidin-3-yloxy, 1-methyl-4-fluoropiperidin-4-ylmethoxy, 1-methylazetidin-3-ylmethoxy, 1-methylpiperidin-3-ylethoxy, 1-methylpiperidin-3-ylmethoxy, 1-methylpiperidin-4-ylmethoxy, 1-methylpiperidin-4-yloxy, 1-methylpyrrolidin-3-ylmethoxy, 1-methylpyrrolidin-3-yloxy, 2,3-dihydroxypropoxy, 2-oxopiperidin-4-ylmethoxy, 2-oxopyrrolidin-1-yleithoxy, 3-methyloxetan-3-ylmethoxy, 4-methylmorpholin-2-ylmethoxy, 4-methylpiperazin-l-ylethoxy, 4-methylpiperazin-1-ylpropoxy, azetidin-3-ylmethoxy, morpholin-2-ylmethoxy, piperidin-1-ylpropoxy, piperidin-3-ylmethoxy, piperidin-4-ylmethoxy, piperidin-4-yloxy, pyrrolidin-3-ylmethoxy, and pyrrolidin-3-yloxy;
R¹⁰ᵃ is selected from hydrogen, —OCH₃, and fluoro; and
R¹⁰ᵇ is selected from hydrogen, —OCH₃, —OCF₂, fluoro, chloro, —CH₃, CN, OH, and —C(O)NH₂.

17. The compound of claim 1, wherein m is 1.

18. A pharmaceutical composition comprising a compound of claim 1 and a pharmaceutically acceptable carrier.

19. A method of treating mastocytosis associated with a mutant Kit that is constitutively active, the method comprising administering to a patient a therapeutically effective amount of a compound of claim 1 or a pharmaceutical composition of claim 18.

20. A method of treating gastrointestinal stromal tumor associated with a mutant Kit that is constitutively active, the method comprising administering to a patient a therapeutically effective amount of a compound of claim 1 or a pharmaceutical composition of claim 18.

21. The method of claim 19, wherein said mutant Kit is mutated at residue D816.

22. The method of claim 20, wherein said mutant Kit is mutated at residue D816.

23. The method of claim 21, wherein said mutant Kit is D816V.

24. The method of claim 22, wherein said mutant Kit is D816V.

25. A method of inhibiting mutant Kit in a subject in need thereof, the method comprising administering to a patient a therapeutically effective amount of a compound of claim 1 or a pharmaceutical composition of claim 18.

26. The method of claim 25, wherein said mutant Kit is mutated at residue D816.

27. The method of claim 26, wherein said mutant Kit is D816V.

* * * * *